US008507274B2

(12) United States Patent
Melton et al.

(10) Patent No.: US 8,507,274 B2
(45) Date of Patent: Aug. 13, 2013

(54) COMPOSITIONS AND METHODS FOR PROMOTING THE GENERATION OF DEFINITIVE ENDODERM

(75) Inventors: Douglas A. Melton, Lexington, MA (US); Malgorzata Borowiak, Somerville, MA (US); Rene Maehr, Somerville, MA (US); Shuibing Chen, Arlington, MA (US); Weiping Tang, Madison, WI (US); Julia L. Fox, Arlington, MA (US); Stuart L. Schreiber, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/679,406

(22) PCT Filed: Feb. 5, 2010

(86) PCT No.: PCT/US2010/023303
§ 371 (c)(1),
(2), (4) Date: Aug. 12, 2010

(87) PCT Pub. No.: WO2010/091241
PCT Pub. Date: Aug. 12, 2010

(65) Prior Publication Data
US 2012/0088300 A1 Apr. 12, 2012

Related U.S. Application Data

(60) Provisional application No. 61/150,509, filed on Feb. 6, 2009.

(51) Int. Cl.
*C12N 5/00* (2006.01)
*C12N 5/02* (2006.01)
*C07C 61/06* (2006.01)
*C07C 61/16* (2006.01)
*C07C 405/00* (2006.01)

(52) U.S. Cl.
USPC ............................ 435/377; 435/366; 560/503

(58) Field of Classification Search
None
See application file for complete search history.

(56) References Cited

U.S. PATENT DOCUMENTS

| | | | |
|---|---|---|---|
| 7,326,572 | B2 | 2/2008 | Fisk |
| 7,510,876 | B2 | 3/2009 | D'Amour |
| 2002/0019046 | A1 | 2/2002 | Carpenter |
| 2005/0037493 | A1 | 2/2005 | Mandalam |
| 2005/0158853 | A1 | 7/2005 | D'Amour |
| 2005/0260749 | A1 | 11/2005 | Odorico |
| 2005/0266554 | A1 | 12/2005 | D'Amour |
| 2006/0003313 | A1 | 1/2006 | D'Amour |
| 2007/0281355 | A1 | 12/2007 | Dalton |
| 2008/0300205 | A1 | 12/2008 | Tsai |

FOREIGN PATENT DOCUMENTS
WO 01/51616 A2 7/2001

OTHER PUBLICATIONS

Borowiak Cell Stem Cell, 2009, 4:348-358.*
Verfaillie et al. Hematology, pp. 369-391, 2002.*
Hoffman et al. Nature Biotech., 23(6): 699-708, 2005.*
Chen et al. Self-renewal of embryonic stem cells by a small molecule. Proc Natl Acad Sci U S A 103, 17266-17271 (2006).
D'Amour, et al. Efficient differentiation of human embryonic stem cells to definitive endoderm. Nat Biotechnol 23, 1534-1541 (2005).
D'Amour, et al. Production of pancreatic hormone-expressing endocrine cells from human embryonic stem cells. Nat Biotechnol 24, 1392-1401 (2006).
Desbordes et al. High-throughput screening assay for the identification of compounds regulating self-renewal and differentiation in human embryonic stem cells. Cell Stem Cell 2, 602-612 (2008).
Ding et al. A role for chemistry in stem cell biology. Nat Biotechnol 22, 833-840 (2004).
Kubo et al. Development of definitive endoderm from embryonic stem cells in culture. Development 131, 1651-1662 (2004).
Lewis et al. Definitive endoderm of the mouse embryo: formation, cell fates, and morphogenetic function. Dev Dyn 235, 2315-2329 (2006).
McLean et al. Activin a efficiently specifies definitive endoderm from human embryonic stem cells only when phosphatidylinositol 3-kinase signaling is suppressed. Stem Cells 25, 29-38 (2007).
Micallef et al. Retinoic acid induces Pdx1-positive endoderm in differentiating mouse embryonic stem cells. Diabetes 54, 301-305 (2005).
Wells et al. Early mouse endoderm is patterned by soluble factors from adjacent germ layers. Development 127, 1563-1572 (2000).
Wu et al. Small molecules that induce cardiomyogenesis in embryonic stem cells. J Am Chem Soc 126, 1590-159 (2004).
Yasunaga et al. Induction and monitoring of definitive and visceral endoderm differentiation of mouse ES cells. Nat Biotechnol 23, 1542-1550 (2005).
International Search Report for PCT/US2010/023303 mailed Dec. 24, 2010.

\* cited by examiner

*Primary Examiner* — Valarie Bertoglio
(74) *Attorney, Agent, or Firm* — Morse, Barnes-Brown & Pendleton, P.C.; Lisa M. Treannie, Esq.

(57) ABSTRACT

Certain embodiments disclosed herein are directed to a method of producing endoderm cells, such as definitive endoderm cells by exposing stem cells such as embryonic stem cells or induced pluripotent stem (iPS) cells to an effective amount of at least one compound described herein to differentiate the stem cells into the endoderm cells such as definitive endoderm cells. Differentated endoderm cells produced by the methods disclosed herein can be differentiated into pancreatic epithelium, and other endoderm derivatives such as thymus, liver, stomach, intestine and lung. Another aspect of the present invention relates to a method of producing pancreatic progenitor cells, such as Pdx1-positive pancreatic progenitor cells by exposing endoderm cells, such as definitive endoderm cells to an effective amount of at least one compound described herein to differentiate the definitive endoderm cells into Pdx1-positive pancreatic progenitor cells. Kits and compositions comprising Pdx1-positive pancreatic progenitor produced using the methods are also described.

9 Claims, 7 Drawing Sheets

8A

8B

COMPOSITIONS AND METHODS FOR PROMOTING THE GENERATION OF DEFINITIVE ENDODERM

CROSS REFERENCE TO RELATED APPLICATIONS

This application is a 35 U.S.C. §371 National Stage Application of International Application No. PCT/US2010/023303 filed on Feb. 5, 2010, which designates the United States, and which claims the benefit under 35 U.S.C. §119(e) of U.S. Provisional Application Serial No: 61/150,509 filed Feb. 6, 2009, the contents of which are incorporated herein by reference in its entirety.

GOVERNMENT SUPPORT

This invention was made with government support under DK072473 awarded by the National Institutes of Health. The government has certain rights in the invention

FIELD OF THE INVENTION

Certain embodiments disclosed herein relate generally to stem cells. More particularly, certain examples disclosed herein relate to pancreatic cells and pancreatic cell precursors that are produced by exposure of pluripotent stem cells, (e.g. human embryonic stem cells) or iPS cells, or endoderm cells (e.g. definitive endoderm cells) derived therefrom, to one or more small molecule compounds.

BACKGROUND OF THE INVENTION

Type I diabetes results from the destruction of insulin producing pancreatic beta cells and therefore there are several approaches aimed at cell-based strategies to replace these cells and rejuvenate the pancreas. The spontaneous or undirected differentiation of ES cells produces very small numbers of insulin producing cells, barely enough for research study and far short of the numbers needed for therapeutic application.

SUMMARY OF THE INVENTION

An essential step for therapeutic and research applications of stem cells is the ability to efficiently and reproducibly differentiate them into specific differentiated cell types. Endodermal cell derivatives, including lung, liver and pancreas, are of interest for regenerative medicine. The present invention generally describes herein features a strategy to increase the efficiency of beta cell formation by exposing stem cells, e.g. embryonic stem cells and derivatives to factors they would normally encounter in vivo during embryonic development. The starting point for this strategy is differentiating stem cells, e.g. embryonic stem cells into definitive endoderm.

In particular, the present invention relates to methods and compositions for the efficient chemically mediated differentiation of pluripotent stem cells, such as embryonic stem cells and iPS cells, or variants thereof into endoderm cells, in particular definitive endoderm cells. In some embodiments, the method comprises contacting the pluripotent stem cells, such as embryonic stem cells and iPS cells with a compound of Formula (I) as disclosed herein, such as a compound of IDE1 or IDE2 to induce the differentiation of the pluripotent stem cells, such as embryonic stem cells and iPS cells to endoderm cells, in particular definitive endoderm cells. Such definitive endoderm cells are referred herein as chemically-induced definitive endoderm cells.

Another aspect relates to methods and compositions for the efficient differentiation of endoderm cells, such as definitive endoderm cells into pancreatic progenitor cells, which express Pdx1. In some embodiments, the method comprises contacting the definitive endoderm cells with a compound of Formula (II) as disclosed herein, such as a compound of Indolactam V (ILV) to induce the differentiation of the definitive endoderm cells to pancreatic progenitor cells. Such pancreatic progenitor cells are referred herein as chemically-induced pancreatic progenitor cells.

Accordingly, the present invention provides an entirely chemically mediated step-wise differentiation of preparing pancreatic progenitor cells from pluripotent stem cells, such as embryonic stem cells, iPS cells or intermediates thereof. In particular, the present invention provides a two-stage approach for generating pancreatic progenitors from pluripotent stem cells, such as embryonic stem cells or iPS cells or the like. In particular, Stage 1 contacting a population of pluripotent stem cells, such as embryonic stem cells or iPS cells with at least one compound of Formula (I), such as IDE1 or IDE2 to generate endoderm cells, such as definitive endoderm cells. In some embodiments, the endoderm cells, such as definitive endoderm cells from Stage 1 can be used in Stage 2. In some embodiments, Stage 2 comprises contacting a population of definitive endoderm cells with a compound of Formula (II), such as Indolactam V to generate Pdx1-positive pancreatic progenitor cells. In some embodiments, a further step (Step 3) can be performed if the user wants to obtain mature pancreatic islet cells or pancreatic β-cells, by methods commonly known in the art, such as nicotinamide as a terminal differentiating agent, or transcription factors can be activated by direct manipulation which causes progression from Pdx1 positive pancreatic precursors to mature islet cells.

The step-wise approach to generate Pdx1-positive pancreatic precursors from pluripotent stem cells is intended as a guide, and is not intended to limit the invention except were explicitly indicated.

There have been several previous reports for the generation of definitive endoderm cells, such as U.S. Pat. No. 7,510,876 which reports using growth factors of the TGFβ superfamily to differentiate human pluripotent stem cells into definitive endoderm cells. However, unlike the present invention, the '876 patent did not use chemical-mediated differentiation, nor did it report a compound of Formula (I), such as IDE1 or IDE2 to induce differentiation of pluripotent stem cells to endoderm cells. Furthermore, the '876 patent did not report a method to produce pancreatic precursors from pluripotent stem cells in a two-step process using only chemicals rather than growth factors, or genetic manipulation of introducing transcription factors.

Similarly, while the U.S. Pat. No. 7,326,572 reports a method to produce endoderm cells from human embryonic cells, it reports a first step using a combination of the growth factor Activin A with n-butyrate or the combination of retinoic acid (RA) and enriching agents (e.g. selenium and thyroid hormone, such as T3) to generate endoderm cells from pluripotent stem cells, and a second step of culturing the endoderm cells with a combination of TGF-(antagonists such as Nogin, and mitogens such as FGF family members such as EGF) to generate Pdx1-positive pancreatic precursors from the endoderm cells, which can subsequently be used in a third step to differentiate the Pdx1-positive precursors into mature islet cells by nicotinamide or transcription factors to direct the progression from Pdx1 positive pancreatic precursors to mature islet cells. However, unlike the '572 application, which requires a combination of multiple different factors at each of the steps, the present invention only requires a cell to be contacted with a compound of formula (I) (e.g. IDE1 or IDE2) in step 1 for chemically-inducing the differentiation of a pluripotent stem cell to an endoderm cell, such as definitive endoderm cell, and a compound of Formula (II) for step 2 to chemically-induce the differentiation of a definitive endoderm cell to a Pdx1-positive pancreatic precursor cell.

In addition, other methods for producing definitive endoderm cells are known in the art, including, for example the methods which are set forth in United States application publication US2006/0003446 to G. Keller, et al.; US2006/0003313 to K. D'Amour, et al., US2005/0158853 to K. D'Amour, et al., and US2005/0260749 of Jon Odorico, et al., relevant portions of which are incorporated by reference herein. However, these reports do not teach or disclose methods for chemically-inducing the differentiation of pluripotent stem cells into endoderm cells, e.g. definitive endoderm cells, nor the use of compounds of Formula (I) (e.g. IDE1 or IDE2) for the chemical-induced differentiation of human pluripotent stem cells into human endoderm cells, e.g. human definitive endoderm cells. In some embodiments, the chemical-induced differentiation of human pluripotent stem cells into human endoderm cells occurs by contacting the cells with a compound of Formula (I), e.g. IDE1 or IDE2 can include additional compounds, e.g. growth factors or differentiation factors. Accordingly, the term "chemically-induced" as used herein does not preclude the use of additional factors in combination with a compound as disclosed herein. In some embodiments, "chemically-induced" refers to the use of the compounds alone for the chemically-mediated induced differentiation of a cell (e.g. of a pluripotent stem cell into a definitive endoderm cell). In alternative embodiments, "chemically-induced" refers to the use of the compounds (e.g. compounds of Formula (I) and/or Formula (II)) in the presence of at least one additional agent (e.g. growth factors or other polypeptides or small molecules) for the chemically-mediated induced differentiation of a cell (e.g. of a pluripotent stem cell into a definitive endoderm cell)

In some embodiments, the definitive endoderm cells produced using the methods as described herein, e.g. by exposing pluripotent stem cells (e.g. embryonic stem cells or iPS cells) to at least one compound of Formula (I) (e.g. IDE1 and/or IDE2) can, in addition to being used to generate pancreatic epithelium (e.g. Pdx1-positive pancreatic progenitor cells), can also be used to generate other endoderm derivative cell such as, but not limited to thymus, liver, stomach, intestine and lung.

One aspect of the present invention provides method of producing a definitive endoderm cell from a pluripotent stem cell, where the methods comprises contacting a population of pluripotent stem cells with at least one compound of Formula (I) to induce the differentiation of at least one pluripotent stem cell into a definitive endoderm cell, wherein the definitive endoderm cell expresses Sox17, or HNF3B (FoxA2), or Sox17 and HNF3B (FoxA2) and wherein the compound of formula (I) is:

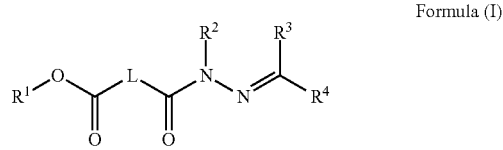

Formula (I)

wherein:
R$^1$ and R$^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);
R$^3$ and R$^4$ are independently H, halogen, alkyl, alkenyl, alkynyl, alkoxy, aryl, heteroaryl, cyclyl, or cyclyl, each of which can be optionally substituted, or R$^3$ and R$^4$ together with the carbon to which they are attached from an optionally substituted cyclyl of heterocycyl; and
L is C$_1$-C$_{10}$ alkylenyl, C$_2$-C$_{10}$ alkenylenyl, or C$_2$-C$_{10}$ alkynylenyl, each of which can be optionally substituted and/or can be interrupted in the backbone with one or more of O, N, S, S(O), and C(O).

In some embodiments, the pluripotent stem cell is an embryonic stem (ES) cell or an induced pluripotent stem (iPS) cell. In some embodiments, the stem cell is from a mammal, such as a human and the stem cell is a human stem cell.

In some embodiments, the method further comprises isolating a population of definitive endoderm cells, wherein at least 5%, 10%, 15%, 20%, 25%, 30%, 35%, 50%, 75% or greater of the total cells in the isolated population are definitive endoderm cells.

In some embodiments of this and all aspect of the invention, a compound of formula (I) is IDE1 having the structure:

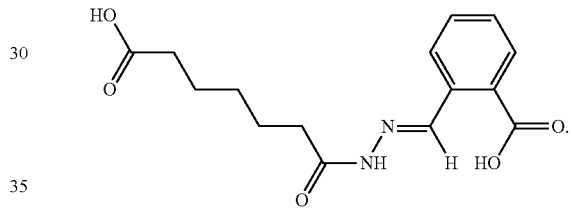

In some embodiments of this and all aspect of the invention, a compound of formula (I) is IDE2 having the structure:

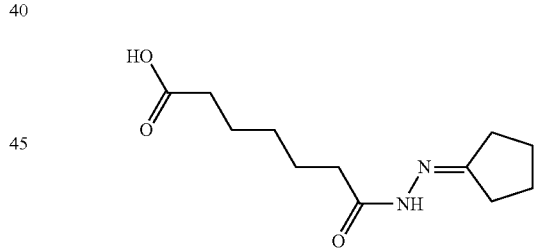

In some embodiments of this and all aspect of the invention, a compound of Formula (I) is an HDAC inhibitor.

In some embodiments of this and all aspect of the invention, a pluripotent stem cell is contacted with the compound of Formula (I) for at least 1 day, for example, at least about 2 days, or at least about 3 days, or at least about 3 days, or at least about 5 days, or at least about 6 days or more than 6 days.

In some embodiments, a pluripotent stem cell is contacted with a compound of Formula (I) at a concentration of between 25 nM-10 µM, for example, in some embodiments, a pluripotent stem cell is contacted with a compound of Formula (I) which is IDE1 at a concentration of between 50 nM-5 µM, or at a concentration of at least 50 nM, or at least 100 nM. In some embodiments, a pluripotent stem cell is contacted with a compound of Formula (I) which is IDE2 at a concentration of between 50 nM-5 µM, e.g. at a concentration of at least 100 nM or at least 200 nM.

In some embodiments, the at least 20% of the pluripotent stem cells in the population of pluripotent stem cells are induced to differentiate a definitive endoderm cell, and in some embodiments, at least 40% or at least between 80-90% of the pluripotent stem cells in the population of pluripotent stem cells are induced to differentiate a definitive endoderm cell.

In some embodiments, the method for producing a definitive endoderm cell from a pluripotent stem cell comprising contacting a population of pluripotent stem cells with at least one compound of Formula (I) to induce the differentiation of at least one pluripotent stem cell into a definitive endoderm cell, further comprising exposing the stem cells to at least one additional agent, e.g. an agent selected from the group consisting of: Nodal, Activin A or Wnt3a.

In some embodiments, a definitive endoderm cell produced by the methods as disclosed herein expresses at least one marker selected from the group consisting of: Nodal, Tmprss2, Tmem30b, St14, Spink3, Sh3gl2, Ripk4, Rab15, Npnt, Clic6, Cldn8, Cacna1b, Bnipl, Anxa4, Emb, FoxA1, Sox17, and Rbm35a, wherein the expression of at least one marker is upregulated to by a statistically significant amount in the definitive endoderm cell relative to the pluripotent stem cell from which it was derived. In some embodiments, a definitive endoderm cell produced by the methods as disclosed herein does not express by a statistically significant amount at least one marker selected the group consisting of: Gata4, SPARC, AFP and Dab2 relative to the pluripotent stem cell from which it was derived. In some embodiments, a definitive endoderm cell produced by the methods as disclosed herein does not express by a statistically significant amount at least one marker selected the group consisting of: Zic1, Pax6, Flk1 and CD31 relative to the pluripotent stem cell from which it was derived.

In some embodiments, a definitive endoderm cell produced by the methods as disclosed herein has a higher level of phosphorylation of Smad2 by a statistically significant amount relative to the pluripotent stem cell from which it was derived. In some embodiments, a definitive endoderm cell produced by the methods as disclosed herein has the capacity to form gut tube in vivo. In some embodiments, a definitive endoderm cell produced by the methods as disclosed herein can differentiate into a cell with morphology characteristic of a gut cell, and wherein a cell with morphology characteristic of a gut cell expresses FoxA2 and/or Claudin6. In some embodiments, a definitive endoderm cell produced by the methods as disclosed herein can be further differentiated into a cell of endoderm origin.

In some embodiments, the method for producing a definitive endoderm cell from a pluripotent stem cell comprising contacting a population of pluripotent stem cells with at least one compound of Formula (I) to induce the differentiation of at least one pluripotent stem cell into a definitive endoderm cell, further comprises differentiating the definitive endoderm cell into a Pdx1-positive pancreatic progenitor cell, wherein the Pdx1-positive pancreatic progenitor cell expresses Pdx1. In some embodiments, the Pdx1-positive pancreatic progenitor cell also expresses HNF6.

In some embodiments, the method for producing a definitive endoderm cell from a pluripotent stem cell comprising contacting a population of pluripotent stem cells with at least one compound of Formula (I) to induce the differentiation of at least one pluripotent stem cell into a definitive endoderm cell, further comprises contacting a population of definitive endoderm cells with at least one compound of Formula (II) to induce the differentiation of at least one definitive endoderm cell into a Pdx1-positive pancreatic progenitor cell, wherein the compound of formula (II) is:

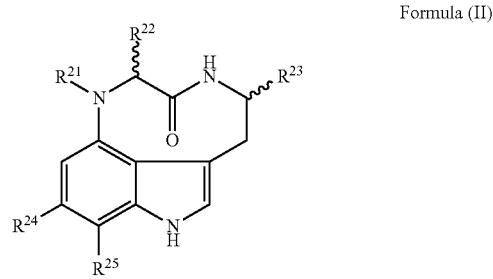

Formula (II)

wherein: $R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they are attached form an optionally substituted cyclyl.

In all aspects and embodiments of the invention, a compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

In some embodiments, the methods for producing a population of Pdx1-positive pancreatic progenitor cells from definitive endoderm cell, where the definitive endoderm cells is chemically induced from a pluripotent stem cell by contacting a population of pluripotent stem cells with at least one compound of Formula (I), which induces the differentiation of at least one pluripotent stem cell into a definitive endoderm cell, and then the definitive endoderm cell further comprises contacting a population of definitive endoderm cells with at least one compound of Formula (II), the method can further comprise isolating the population of Pdx1-positive pancreatic progenitor cells. In some embodiments, the method also further comprises differentiating the population of Pdx1-positive pancreatic progenitor cells into a population of insulin producing cells, for example into a population of cells having at least one characteristic of endogenous pancreatic β-cells, or a cell with at least one characteristic of an endogenous pancreatic β-cell is secretion of insulin in response to glucose.

In some embodiments, the methods as disclosed herein for producing Pdx1-positive pancreatic progenitors further comprises implanting a population of Pdx1-positive pancreatic progenitor cells or their differentiated progeny of insulin producing cells or cells having at least one characteristic of endogenous pancreatic β-cells into a subject in need thereof. In some embodiments, the subject in need thereof has diabetes, or is at risk of developing diabetes. In some embodiments, where a definitive endoderm cell or a Pdx1-positive pancreatic progenitor differentiated from said definitive endoderm cell is derived from a pluripotent stem cell which is an iPS cell, the induced pluripotent stem (iPS) cell can be obtained from a subject with diabetes or at risk of developing diabetes.

Another aspect of the present invention relates to an isolated population of definitive endoderm cells obtained from a population of pluripotent stem cells by a process comprising contacting the population of pluripotent stem cells with at least one compound of Formula (I), wherein the compound of Formula (I) is:

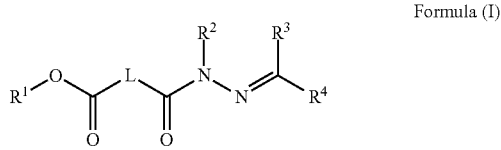

Formula (I)

wherein:
R$^1$ and R$^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);
R$^3$ and R$^4$ are independently H, halogen, alkyl, alkenyl, alkynyl, alkoxy, aryl, heteroaryl, cyclyl, or cyclyl, each of which can be optionally substituted, or R$^3$ and R$^4$ together with the carbon to which they are attached from an optionally substituted cyclyl of heterocycyl; and
L is C$_1$-C$_{10}$ alkylenyl, C$_2$-C$_{10}$ alkenylenyl, or C$_2$-C$_{10}$ alkynylenyl, each of which can be optionally substituted and/or can be interrupted in the backbone with one or more of O, N, S, S(O), and C(O).

In some embodiments, an isolated population of definitive endoderm cells obtained from a population of pluripotent stem cells by a process comprising contacting the population of pluripotent stem cells with at least one compound of IDE1 or IDE2, wherein the compound of IDE1 having the structure:

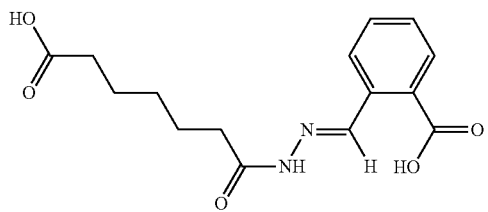

and the compound of IDE2 having the structure:

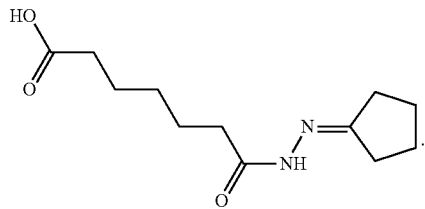 [SMILES: O=C(O)CCCCCC(=O)NN=C1CCCC1]

Another aspect of the present invention provides to an isolated population of Pdx1-positive pancreatic progenitors obtained from a population of pluripotent stem cells by a process comprising, (i) contacting the population of pluripotent stem cells with at least one compound of Formula (I), (e.g. but not limited to IDE1 and/or IDE2) to induce the differentiation of at least one pluripotent stem cell into definitive endoderm cell, and; (ii) contacting at least one definitive endoderm cell with at least one compound of Formula (II) (e.g. but not limited to indolatam V) to induce the differentiation of at least one definitive endoderm cell into a Pdx1-positive progenitor cell.

In some embodiments, an isolated population of Pdx1-positive pancreatic progenitors obtained from pluripotent stem cells is obtained by contacting a population of pluripotent stem cells with a compound of wherein the compound of Formula (I) to produce definitive endoderm cells, where compound of Formula (I) is:

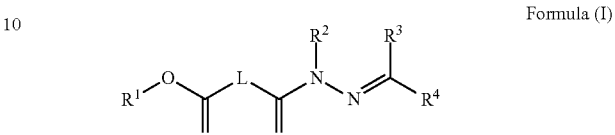

Formula (I)

wherein:
R$^1$ and R$^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);
R$^3$ and R$^4$ are independently H, halogen, alkyl, alkenyl, alkynyl, alkoxy, aryl, heteroaryl, cyclyl, or cyclyl, each of which can be optionally substituted, or R$^3$ and R$^4$ together with the carbon to which they are attached from an optionally substituted cyclyl of heterocycyl; and
L is C$_1$-C$_{10}$ alkylenyl, C$_2$-C$_{10}$ alkenylenyl, or C$_2$-C$_{10}$ alkynylenyl, each of which can be optionally substituted and/or can be interrupted in the backbone with one or more of O, N, S, S(O), and C(O).

In some embodiments and all aspects described herein, a compound of Formula (I) used in the production of an isolated population of Pdx1-positive pancreatic progenitors selected from IDE1 or IDE2, wherein the compound of IDE1 having the structure:

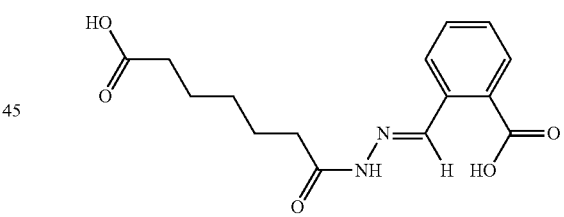

and the compound of IDE2 having the structure:

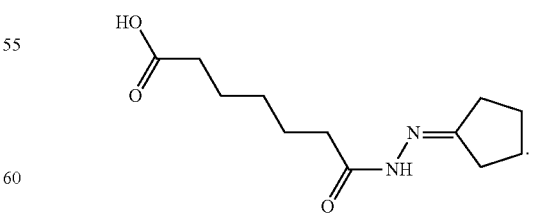

In some embodiments and all aspects described herein, a compound of Formula (II) used in the production of an isolated population of Pdx1-positive pancreatic progenitors has the structure of:

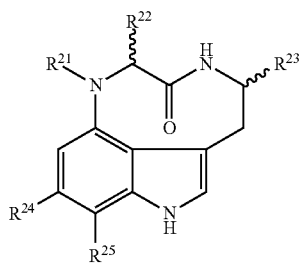

Formula (II)

wherein: $R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they arre attached form an optionally substituted cyclyl.

In some embodiments and all aspects described herein, a compound of Formula (II) used in the production of an isolated population of Pdx1-positive pancreatic progenitors is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

Another aspect of the present invention provides a composition comprising a population of definitive endoderm cells produced according to the any of the methods as disclosed herein, e.g. contacting a population of pluripotent stem cells with at least one compound of Formula (I) (e.g. but not limited to IDE1 and/or IDE2) to induce the differentiation of at least one pluripotent stem cell into a definitive endoderm cell Another aspect of the present invention provides a composition comprising a population of Pdx1-positive pancreatic progenitor cells produced according to any of the methods as disclosed herein, e.g. contacting a population of definitive endoderm cells with at least one compound of Formula (II) (e.g. indotactam V), to induce the differentiation of the definitive endoderm cells into a Pdx1-positive pancreatic progenitor, or e.g. contacting a pluripotent stem cells with at least one compound of Formula (I) (e.g. but not limited to IDE1 and/or IDE2) to induce the differentiation of at least one pluripotent stem cell into a definitive endoderm cell, and the subsequently contacting a definitive endoderm cell with at least one compound of Formula (II) (e.g. indotactam V), to induce the differentiation of the definitive endoderm cell into a Pdx1-positive pancreatic progenitor cell.

Another aspect of the present invention provides a method for the treatment of a subject with diabetes, the method comprising administering to a subject a composition comprising an isolated population of Pdx1-positive pancreatic progenitor cells produced by the methods as disclosed herein or a differentiated progeny of a Pdx1-positive pancreatic progenitor cells produced by the method as disclosed herein. In some embodiments, the Pdx1-positive pancreatic progenitor cells are produced from a population of pluripotent stem cells obtained from the same subject as the Pdx1-positive pancreatic progenitor cells are administered to. In some embodiments, a Pdx1-positive pancreatic progenitor cells are produced from an population of iPS cell, wherein the iPS cell is derived from a cell obtained from the same subject as the Pdx1-positive pancreatic progenitor cells are administered to.

In some embodiments, a subject administered a composition comprising an isolated population of Pdx1-positive pancreatic progenitor cells has, or has an increased risk of developing diabetes, such as, for example, Type I diabetes, Type II diabetes, Type 1.5 diabetes and pre-diabetes. In some embodiments, the subject has, or has increased risk of developing a metabolic disorder.

Another aspect of the present invention provides the use of an isolated population of definitive endoderm cells produced by the methods as disclosed herein for differentiating into Pdx1-positive pancreatic progenitors.

Another aspect of the present invention provides the use of an isolated population of definitive endoderm cells produced by the methods as disclosed herein for differentiating into a cell of endoderm origin, for example into a cell such as a liver cell, a epithelial cell, a pancreatic cell, a pancreatic endoderm (PE) cell, a thymus cell, an intestine cell, a stomach cell, a thyroid cell and a lung cell.

Another aspect of the present invention provides the use of an isolated population of Pdx1-positive progenitors produced by the methods as disclosed herein for administering to a subject in need thereof, such as, for example, a subject who has, or who has an increased risk of developing diabetes, such as Type I diabetes, Type II diabetes, Type 1.5 and pre-diabetes. In some embodiments, the subject has, or has increased risk of developing a metabolic disorder.

Another aspect of the present invention provides a kit comprising at least one compound of Formula (I) as disclosed herein. In some embodiments, the kit comprises a compound of Formula (I) which is selected from IDE1 or IDE2, wherein the compound of IDE1 having the structure:

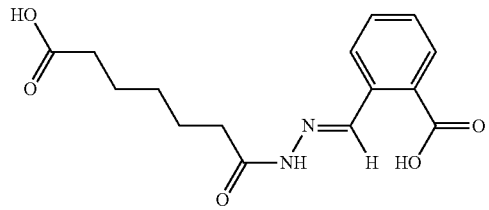

and the compound of IDE2 having the structure:

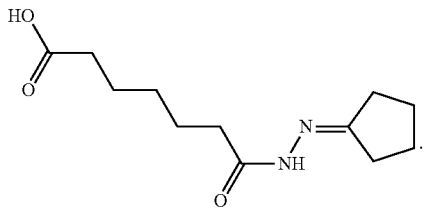 [SMILES: O=C(O)CCCCCC(=O)NN=C1CCCC1]

In some embodiments, the kit further comprises at least one compound of Formula (II) as disclosed herein. In some embodiments, a compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

In some embodiments, the kit further comprises an isolated population of pluripotent stem cells, for example as a control population of pluripotent stem cells. In some embodiments, the kit further comprises a control cell population selected from the group of; an endoderm cell population, a definitive endoderm cell population, a pluripotent cell population, a Pdx1-positive pancreatic progenitor cell population. In some embodiments, the kit further comprises at least one agent for the detection of a marker for a definitive endoderm cell, wherein the marker can be selected from any of the group consisting of; Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Sox17, and Rbm35a. In some embodiments, the kit further comprises at least one agent for the detection of a marker for a Pdx1-positive pancreatic progenitor, wherein the marker can be selected from any of the group consisting of; Pdxl and HNF6.

Another aspect of the present invention provides a reaction admixture comprising a definitive endoderm cell and at least one compound of Formula (I), as disclosed herein. In some embodiments, the admixture comprises a definitive endoderm cell and a compound of Formula (I) which is selected from IDE1 or IDE2, wherein the compound of IDE1 having the structure:

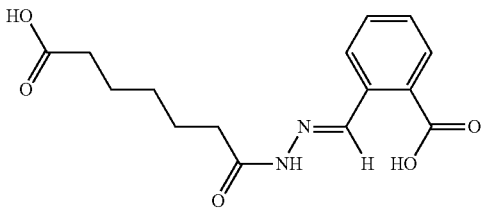 [SMILES: O=C(O)CCCCCC(=O)N/N=C/c1ccccc1C(=O)O]

and the compound of IDE2 having the structure:

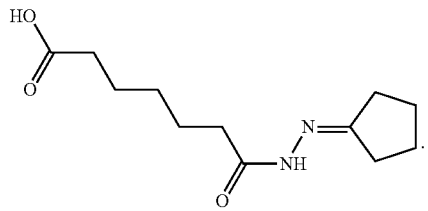 [SMILES: O=C(O)CCCCCC(=O)NN=C1CCCC1]

Another aspect of the present invention provides a reaction admixture comprising a pluripotent stem cell, e.g. iPS cell or embryonic stem cell and at least one compound of Formula (I), as disclosed herein. In some embodiments, the admixture comprises a pluripotent stem cell and a compound of Formula (I) which is selected from IDE1 or IDE2, herein the compound of IDE1 having the structure:

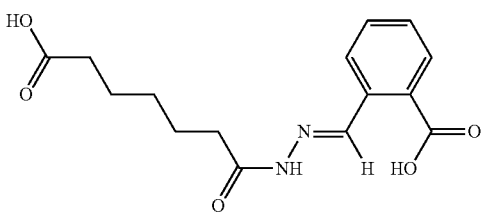 [SMILES: O=C(O)CCCCCC(=O)N/N=C/c1ccccc1C(=O)O]

and the compound of IDE2 having the structure:

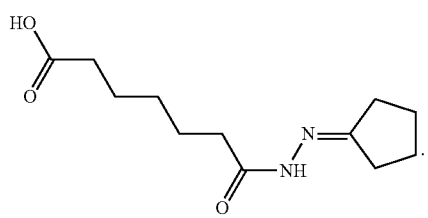 [SMILES: O=C(O)CCCCCC(=O)NN=C1CCCC1]

In some embodiments, the reaction admixture comprises a definitive endoderm cell which is a human definitive endoderm cell. In some embodiments, the reaction admixture comprises a pluripotent stem cell which is a human pluripotent stem cell.

Another aspect of the present invention provides a reaction admixture comprising a Pdx1-positive progenitor cell and at least one compound of Formula (II) as disclosed herein. In some embodiments, the reaction admixture comprises a Pdx1-positive progenitor cell and compound of Formula (II) which is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

Another aspect of the present invention provides a reaction admixture comprising a definitive endoderm cell and at least one compound of Formula (II) as disclosed herein. In some embodiments, the reaction admixture comprises a definitive endoderm cell and a compound of Formula (II) which is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

In some embodiments, the reaction admixture comprises a definitive endoderm cell which is a human definitive endoderm cell. In some embodiments, the reaction admixture comprises a Pdx1-positive progenitor cell is a human Pdx1-positive progenitor cell. In some embodiments, admixtures comprising a Pdx1-positive progenitor cell comprise a Pdx1-progenitor cell which has been differentiated from a definitive endoderm cell, wherein the definitive endoderm cell has differentiated from a pluripotent stem cell by contacting the pluripotent stem cell with a compound of Formula (I), as disclosed herein.

In some embodiments, a reaction admixture comprising a Pdx1-positive progenitor cell can further comprises at least one compound of Formula (I) as disclosed herein. In some embodiments, a reaction admixture comprising a Pdx1-positive progenitor cell can further comprises at least one compound of Formula (I) which is selected from IDE1 or IDE2, wherein the compound of IDE1 having the structure.

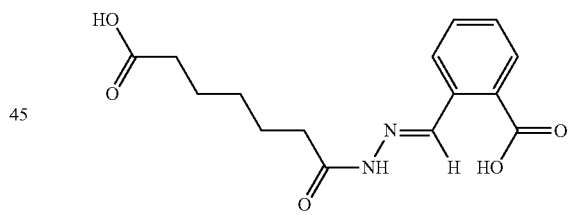

and the compound of IDE2 having the structure:

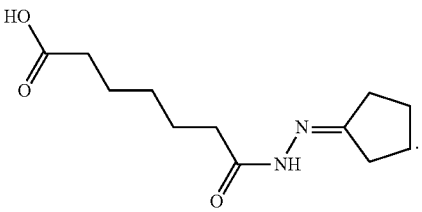 [SMILES: O=C(O)CCCCCC(=O)NN=C1CCCC1]

BRIEF DESCRIPTION OF THE DRAWINGS

Certain illustrative embodiments are described in more detail below with reference to the accompanying figures.

FIG. 1A shows a scheme of differentiation into endoderm and evaluation of an endoderm reporter line. Treatment with either Activin A or Nodal induces endoderm in mouse ES cell cultures and at day 6 of treatment 45% of total cells are Sox17/dsRed double positive (data not shown). Every dsRed+ cell stains positively for Sox17 antibody (data not shown). FIG. 1B shows an overview of the identification of endoderm inducers from small molecule collection. Out of >4000 screened compounds, 27 primary hits were selected and further evaluated for specificity and toxicity. Markers for definitive endoderm (DE) and extra-embryonic endoderm (EE) were tested by Q-RT-PCR and immunohistochemistry and 2 compounds that induced high levels of DE were identified. ≧3 s.d=more than 3 standard deviations.

FIG. 2A shows the chemical structure of IDE1 and IDE2 that induce endoderm cells from mouse ES cells. FIG. 2B shows dose response curves of Sox17 expression (based on immunofluorescence) following treatment with compound for 6 days. The $EC_{50}$ values and curve fitting were performed with Graph Prism software. Data presented as mean±s.d. n=4

FIGS. 3A and 3B show the effect of IDE1 and IDE2, respectively, on the number of Sox17+ and total cells during 14 days of treatment is shown. Endoderm induction by IDE1 and IDE2 peaks at about day 6 and as little as 12 hrs treatment with either compound is sufficient to induce Sox17 expression in ~40% of the cells. FIG. 3C shows the effect of Activin A treatment on the number of Sox17+ and total cells during 14 days of treatment. Activin A induces significant but lower % of Sox17+ cells compared to IDE1 or IDE2 at all tested time points. Cells were analysed at day 6 (for earlier time points) or 14 of culture. FIG. 3D shows the combined effect of compounds and growth factors on Sox17 expression. Co-treatment of mouse ES cells with IDE1 or IDE2 compounds, alone or combined (IDE1+IDE2), or in the presence of Wnt3a or Nodal growth factors (IDE1+Wnt3a, IDE1+Nodal, IDE2+Wnt3a, IDE2+Nodal). Nodal enables shortening of the treatment time and leads to the induction of Sox17 with a slightly high efficiency (55.6%) expression at day 4. No synergy was detected between IDE1 and IDE2 (IDE1+IDE2) or the combination of either compound IDE1 or IDE2 with Wnt3a. All quantifications were based on the percentage of cells stained by Sox17 antibody out of total cell. Data presented as mean±s.d. n=4 experiments.

FIG. 4A shows expression of definitive endodermal markers in Sox17+ cells induced by compound treatment or isolated form E7.5-8.0 embryos. Sox17/dsRed+ cells were sorted by FACS and expression of endoderm genes was analysed by Illumina microarray. Expression of "endoderm signature" genes normalized to the DMSO treated mouse ES cells is shown. Out of 17 genes, only 2, Spink3 and Tmprss2 (marked by *) were expressed at significantly higher levels (>2 fold change) in Sox17+ cells isolated from E7.75 embryos (endoderm). Each bar represents an average of 3 biological replicates and mean±s.d. is shown FIG. 4B. FIG. 4B shows scatter plots comparing the global gene expression in Sox17/dsRed+ populations sorted out from Sox17/dsRed E7.75 embryos and derived either in vitro by treatment with IDE2 (day 6 of treatment) (left panel) or with non-treated mouse ES cell cultures (right panel). The centre diagonal line in the middle visualizes the equivalent levels in gene expression; the two lines either side of the centre diagonal line show two-fold change in gene expression levels between both samples.

FIG. 5A shows analysis of phosphorylation of Smad2 in lysates of ES cells treated with IDE1, IDE2, DMSO, Activin A or Nodal or in the presence of the ALK4/5/7 inhibitor, SB431542. Treatment with IDE1 or IDE2 leads to activation of the TGF-β pathway after 24 hrs, similar to either Nodal or Activin A treatment. Phosphorylation of Smad2 by either of the two compounds is significantly attenuated in the presence of SB431542. FIG. 5B shows an increase in Nodal expression after treatment with small molecules IDE2 or IDE1 or Nodal. Relative expression over DMSO treatment is shown as a mean of triplicate experiments±s.d.

FIG. 6A shows a schematic of in vivo assay to assess the functional potential of compound induced endoderm. Mouse ES cells treated with chemical inducers incorporate into the developing host gut tube. Cultures of mouse ES cell reporter lines expressing constitutive YFP were differentiated into endoderm with IDE1 or IDE2, producing 60-70% Sox17+ cells, then trypsinized and injected into the nascent gut lumen of E8.75 mouse embryos. Dashed line shows an approximate plane of section. FIG. 6B shows that after 24-30 hours ex vivo culture, mouse embryos were fixed, transversally sectioned and stained with antibodies against FoxA2 and Cldn6 to detect gut epithelial cells and anti-YFP antibodies to visualize injected cells. IDE1 and IDE2 induced endodermal cells incorporate into gut tube and show expression of gut tube markers. In contrast, DMSO treated cells remain clustered in the gut tube lumen 30 hrs after injection and do not incorporate into the gut epithelia nor express gut tube markers.

FIG. 8A shows a schematic of the gene targeting strategy used to target the dsRed variant (Shaner et al., 2004) dTomato to the mouse Sox17 locus. Indicated are the targeting vector with exons as grey boxes, the wild type locus and the targeted locus after homologous recombination. EcoRV and HindIII digest were used for Southern blot analysis with an external probe and an internal probe to identify properly targeted ES cell clones. FIG. 8B shows Southern blot analysis with an external 5' probe (upper panel) and a probe against the neomycin selection cassette (lower panel) to confirm that positive clones, parental untargeted cell line, AV3, and targeted Sox17 dsRed clones. The wild type allele migrates at 10.1 kb and the targeted allele at 6.1 kb as identified with the external southern probe. A neomycin cassette can be identified at 6.1 kb with a neo probe.

DETAILED DESCRIPTION OF THE INVENTION

Figure 1:
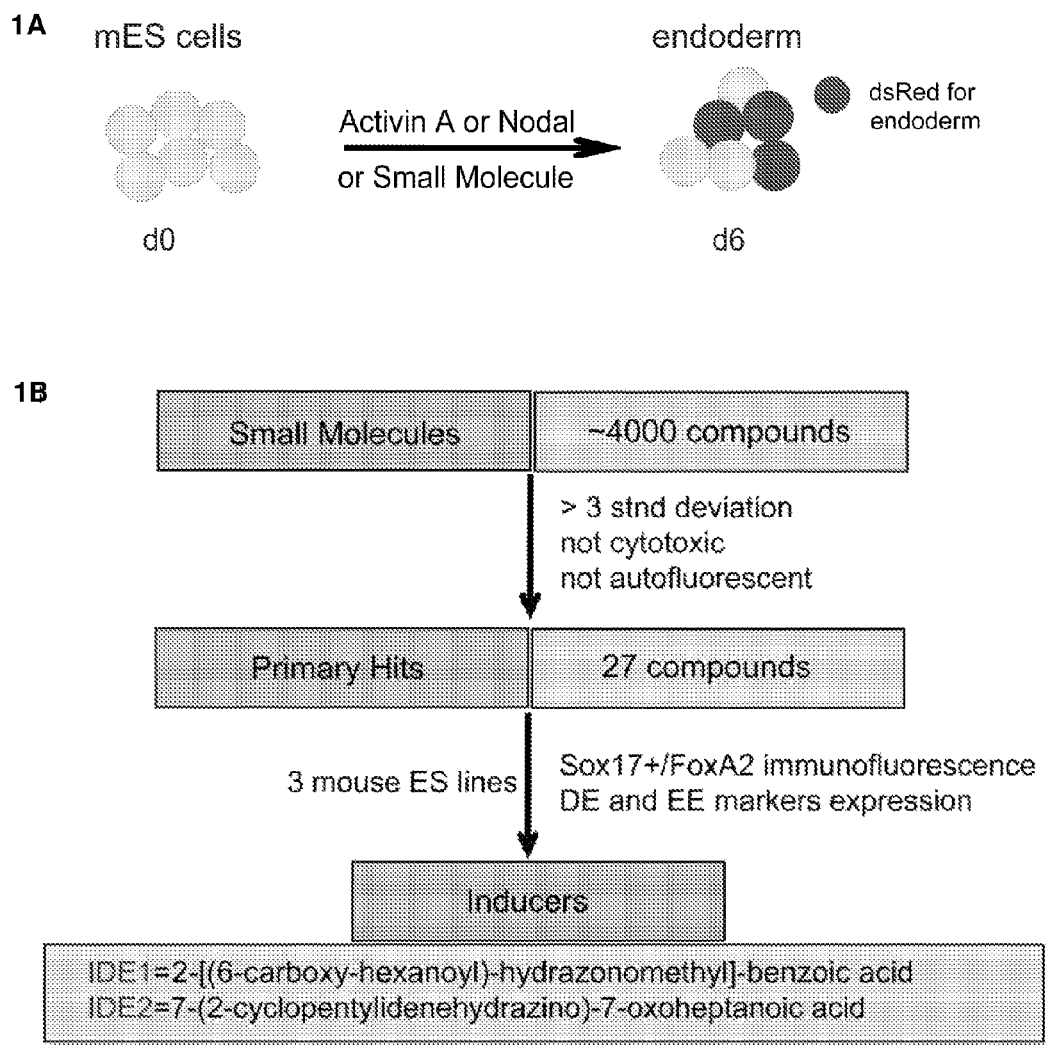
FIG. 1A-1B shows a high throughput screening.

Described herein are methods for the generation of endoderm, e.g., definitive endoderm, by exposing a stem cell to one or more compounds described such as, for example, small molecule compounds. The methods described herein include producing an endoderm (i.e., an endodermal cell) by exposing a stem cell (e.g., an embryonic stem (ES) cell or iPS cell) to a compound described herein e.g., a compound of formula (I), such as IDE1 or IDE2, or an HDAC inhibitor (e.g., a class I/II HDAC inhibitor). In some embodiments the endoderm is further differentiated to a second cell type.

Also described herein are compositions comprising isolated populations of definitive endoderm cells and compositions comprising isolated populations of pancreatic progenitor cells (e.g., cells produced by the methods described herein). Compositions and kits comprising the compounds and/or cells described herein (e.g., made by method described herein) are also include in the description.

In particular, the present invention relates to methods and compositions for chemically-induced differentiation of pluripotent stem cells, such as embryonic stem cells and iPS cells, or variants thereof, into endoderm cells, in particular definitive endoderm cells. The definitive endoderm cells can be differentiated into any cell of endoderm origin, or alternatively in other embodiments, the definitive endoderm cells can be differentiated into Pdx1-positive pancreatic progenitors. In some embodiments, the method comprises contacting the pluripotent stem cells, such as embryonic stem cells and iPS cells with a compound of Formula (I) as disclosed herein, such as a compound of IDE1 or IDE2 to induce the differentiation of the pluripotent stem cells, such as embryonic stem cells and iPS cells to endoderm cells, in particular definitive endoderm cells. Such definitive endoderm cells are referred herein as chemically-induced definitive endoderm cells. In some embodiments, the definitive endoderm cells produced by the chemically-induced differentiation of pluripotent stem cells have the positive expression for at least one or more of the following markers; Sox17+, and FoxA2+ (HNF3β), and have negative or a low level of expression of at least one of the markers selected from the group of Gata4, SPARC, APF, and Dab.

Another aspect relates to methods and compositions for the efficient differentiation of endoderm cells, such as definitive endoderm cells into pancreatic progenitor cells, which express Pdx1. In some embodiments, the method comprises contacting the definitive endoderm cells with a compound of Formula (II) as disclosed herein, such as a compound of Indolactam V to induce the differentiation of the definitive endoderm cells to pancreatic progenitor cells. Such pancreatic progenitor cells are referred herein as chemically-induced pancreatic progenitor cells. In some embodiments, the Pdx1-positive pancreatic progenitors produced by chemically-induced differentiation of endoderm cells, such as definitive endoderm cells are positive for the expression of Pdx1 and HFN6.

Accordingly, the present invention provides an entirely chemically-induced two-step differentiation method for obtaining an isolated population of pancreatic progenitor cells from a population of pluripotent stem cells, such as embryonic stem cells, iPS cells or intermediates thereof. In particular, the present invention provides a two-stage approach for generating pancreatic progenitors from pluripotent stem cells, such as embryonic stem cells or iPS cells or the like. In particular, Stage 1 contacting a population of pluripotent stem cells, such as embryonic stem cells or iPS cells with at least one compound of Formula (I), such as IDE1 or IDE2 to generate endoderm cells, such as definitive endoderm cells. In some embodiments, the endoderm cells, such as definitive endoderm cells from Stage 1 can be used in Stage 2. In some embodiments, Stage 2 comprises contacting a population of definitive endoderm cells with a compound of Formula (II), such as Indolactam V to generate Pdx1-positive pancreatic progenitor cells. In some embodiments, a further step (Step 3) can be performed if the user wants to obtain mature pancreatic islets or pancreatic β-cells, by methods commonly known in the art, such as nicotinamide as a terminal differentiating agent, or transcription factors can be activated by direct manipulation which causes progression from Pdx1 positive pancreatic precursors to mature islet cells.

The methods and compositions as disclosed herein have a greater or similar efficiency as using TGF-β family members such as Activin A and Nodal for producing pancreatic progenitors from stem cells, yet the present invention has numerous advantages including decreased cost of materials, temporal control of the differentiation and reduced risk of infection and contamination of the cell population with growth factors. The step-wise approach to generate Pdx1-positive pancreatic precursors from pluripotent stem cells is intended as a guide, and is not intended to limit the invention except were explicitly indicated.

There have been several previous reports for the generation of definitive endoderm cells, such as U.S. Pat. No. 7,510,876 which reports using growth factors of the TGFβ superfamily to differentiate human pluripotent stem cells into definitive endoderm cells. However, unlike the present invention, the '876 patent did not use chemical-mediated differentiation, nor did it report a compound of Formula (I), such as IDE1 or IDE2 to induce differentiation of pluripotent stem cells to endoderm cells. Furthermore, the '876 patent did not report a method to produce pancreatic precursors from pluripotent stem cells in a two-step process using only chemicals rather than growth factors, or genetic manipulation of introducing transcription factors.

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" refers to are any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein, the term "adult cell" refers to a cell found throughout the body after embryonic development.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of respiratory and digestive tracts (e.g. the intestine), the liver and the pancreas.

The term "a cell of endoderm origin" as used herein refers to any cell which has developed of differentiated from an endoderm cell. For example, a cell of endoderm origin includes cells of the liver, lung, pancrease, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein refers to a cell differentiated from an endoderm cell and which can be differentiated into a pancreatic β-cell. A definitive endoderm cell expresses the marker Sox17. Other markers of definitive endoderm cells include, but are not limited to MIXL2, GATA4, HNF3b, GSC, FGF17, VWF, CALCR, FOXQ1, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid.

The term "pancreatic progenitor" or "pancreatic precursor" are used interchangeably herein and refer to a stem cell which is capable of forming any of; pancreatic endocrine cells, or pancreatic exocrine cells or pancreatic duct cells.

The term "pdx1-positive pancreatic progenitor" as used herein refers to a cell which is a pancreatic endoderm (PE) cell which has the capacity to differentiate into insulin producing cells, such as pancreatic β-cells. A Pdx1-positive pancreatic progenitor expresses the marker Pdx1. Other markers include, but are not limited to Cdcp1, or Ptf1a, or HNF6 or NRx2.2.

The term "pancreatic endoderm" refers to a cell of endoderm origin which is capable of differentiating into multiple pancreatic lineages, including pancreatic beta cells, but no longer has the capacity to differentiate into non-pancreatic lineages.

The term "exocrine cell" as used herein refers to a cell of an exocrine gland, i.e. a gland that discharges its secretion via a duct. In particular embodiments, an exocrine cells refers to a pancreatic exocrine cell, which is a pancreatic cell that produces enzymes that are secreted into the small intestine. These enzymes help digest food as it passes through the gastrointestinal tract. Pancreatic exocrine cells are also known as islets of Langerhans, that secrete two hormones, insulin and glucagon. A pancreatic exocrine cell can be one of several cell types: alpha-2 cells (which produce the hormone glucagon); or β-cells (which manufacture the hormone insulin); and alpha-1 cells (which produce the regulatory agent somatostatin). Non-insulin producing exocrine cells as used herein refers to alpha-2 cells or alpha-1 cells. Note, the term pancreatic exocrine cells encompasses "pancreatic endocrine cells" which refer to a pancreatic cell that produces hormones (e.g., insulin (produced from β-cells) and glucagon (produced by alpha-2 cells) that are secreted into the bloodstream.

As used herein, the term "insulin producing cell" refers to a cell differentiated from a pancreatic progenitor which secretes insulin. An insulin producing cell includes pancreatic β-cells as that term is described herein, as well as pancreatic β-like cells that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. A population of insulin producing cells e.g. produced by differentiating definitive endoderm cells to pancreatic progenitors and then subsequent differentiation into insulin producing cells according to the methods of the present invention can be pancreatic β-cells or β-like cells (e.g., cells that have at least two characteristics of an endogenous β-cell). The novelty of the present composition and methods is not negated by the presence of cells in the population that produce insulin naturally (e.g., beta cells). It is also contemplated that the population of insulin producing cells, e.g. produced by the methods as disclosed herein can comprise pancreatic β-cells or pancreatic β-like cells, and can also contain non-insulin producing cells (i.e. cells of β-cell like phenotype with the exception they do not produce or secrete insulin).

As used herein, the term "endogenous β-cell" or endogenous "pancreatic β-cell" refers to an insulin producing cell of the pancreas or a cell of a pancreatic β-cell (beta cell) phenotype. The phenotype of a pancreatic β-cell is well known by persons of ordinary skill in the art, and include, for example, secretion of insulin in response to an increase in glucose level, expression of markers such as c-peptide, PDX-1 polypeptide and Glut 2, as well as distinct morphological characteristics such as organized in islets in pancreas in vivo, and typically have small spindle like cells of about 9-15 μm diameter.

The term "pancreatic β-like cell" as used herein refers to as used herein refers to a cell produced by the methods as disclosed herein which expresses at least 15% of the amount of insulin expressed by an endogenous pancreatic beta-cell, or at least about 20% or at least about 30%, or at least about 40%, or at least about 50%, or at least about 60%, or at least about 70%, or at least about 80%, or at least about 90%, or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic bets-cell, or alternatively exhibits at least one, or at least two characteristics of an endogenous pancreatic beta-cell, for example, but not limited to, secretion of insulin in response to glucose, and expression of beta-cell markers, such as for example, c-peptide, Pdx1 and glut-2. In one embodiment, the pancreatic β-like cell is not an immortalized cell (e.g. proliferate indefinitely in culture). In one embodiment, the pancreatic β-like cell is not a transformed cell, e.g., a cell that exhibits a transformation property, such as growth in soft agar, or absence of contact inhibition.

The term "β-cell marker" refers to, without limitation, proteins, peptides, nucleic acids, polymorphism of proteins and nucleic acids, splice variants, fragments of proteins or nucleic acids, elements, and other analytes which are specifically expressed or present in pancreatic β-cells. Exemplary β-cell markers include, but are not limited to, pancreatic and duodenal homeobox 1 (PDX-1) polypeptide, insulin, c-peptide, amylin, E-cadherin, Hnf3β, PCI/3, Beta2, Nkx2.2, Nkx6.1, GLUT2, PC2, ZnT-8, and those described in Zhang et al., Diabetes. 50(10):2231-6 (2001). In some embodiment, the β-cell marker is a nuclear 3-cell marker. In some embodiments, the β-cell marker is PDX-1 or PH3.

The term "non-insulin producing cell" as used herein is meant any cell of endoderm origin that does not naturally synthesize, express, or secrete insulin constitutively or by induction. Thus, the term "non-insulin producing cells" as used herein excludes pancreatic beta cells. Examples of non-insulin producing cells that can be used in the methods of the present invention include pancreatic non-beta cells, such as amylase producing cells, acinar cells, cells of ductal adenocarcinoma cell lines (e.g., CD18, CD11, and Capan-I cells (see Busik et al., 1997; Schaffert et al. 1997). Non-pancreatic cells of endoderm origin could also be used, for example, non-pancreatic stem cells and cells of other endocrine or exocrine organs, including, for example, liver cells, tymus cells, thyroid cells, intestine cells, lung cells and pituitary cells. In some embodiments, the non-insulin producing endodermal cells can be mammalian cells or, even more specifically, human cells. Examples of the present method using mammalian pancreatic non-islet, pancreatic amylase producing cells, pancreatic acinar cells are provided herein.

The term "phenotype" refers to one or a number of total biological characteristics that define the cell or organism under a particular set of environmental conditions and factors, regardless of the actual genotype.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

The term "pancreas" refers to a glandular organ that secretes digestive enzymes and hormones. In humans, the pancreas is a yellowish organ about 7 in. (17.8 cm) long and 1.5 in. (3.8 cm) wide. It lies beneath the stomach and is connected to the small intestine, muscular hoselike portion of the gastrointestinal tract extending from the lower end of the stomach (pylorus) to the anal opening. Most of the pancreatic tissue consists of grapelike clusters of cells that produce a clear fluid (pancreatic juice) that flows into the duodenum through a common duct along with bile from the liver. Pancreatic juice contains three digestive enzymes: tryptase, amylase, and lipase, that, along with intestinal enzymes, complete the digestion of proteins, carbohydrates, and fats, respectively. Scattered among the enzyme-producing cells of the pancreas are small groups of endocrine cells, called the islets of Langerhans, that secrete two hormones, insulin and glucagon. The pancreatic islets contain several types of cells: alpha-2 cells, which produce the hormone glucagon; beta cells (also referred to herein as "pancreatic β-cells"), which manufacture the hormone insulin; and alpha-1 cells, which produce the regulatory agent somatostatin. These hormones are secreted directly into the bloodstream, and together, they regulate the level of glucose in the blood. Insulin lowers the blood sugar level and increases the amount of glycogen (stored carbohydrate) in the liver; glucagon has the opposite action. Failure of the insulin-secreting cells to function properly results in diabetes or diabetes mellitus.

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. Reprogramming as used herein also encompasses partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocycyll moieties including macrolides, leptomycins and related natural products or analogues thereof. Compounds can be known to have a desired activity and/or property, or can be selected from a library of diverse compounds.

As used herein, the term "contacting" (i.e., contacting a pluripotent stem cell or a definitive endoderm cell, with a compound) is intended to include incubating the compound and the cell together in vitro (e.g., adding the compound to cells in culture). In some embodiments, the term "contacting" is not intended to include the in vivo exposure of cells to the compounds as disclosed herein that may occur naturally in a subject (i.e., exposure that may occur as a result of a natural physiological process). The step of contacting a pluripotent stem cell with a compound of Formula (I) as in the embodiments related to the production of definitive endoderm cells can be conducted in any suitable manner. For example, the cells may be treated in adherent culture, or in suspension culture. It is understood that the cells contacted with a compound of Formula (I) or of Formula (II) can also be simultaneously or subsequently contacted with another agent, such as a growth factor or other differentiation agent or environments to stabilize the cells, or to differentiate the cells further. Similarly, a pluripotent stem cell can be contacted with a compound of Formula (I) and then with a compound of Formula (II). In some embodiments, the cell is contacted with a compound of Formula (I) and Formula (II) and the contact is temporal separated, and in some embodiments, a cell is contacted with a compound of Formula (I) and Formula (II) substantially simultaneously.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. ScL USA 90:5873-5877, 1993 is incorporated into the NBLAST and XBLAST programs of Altschul et al. (Altschul, et al., J. MoI. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm nih.gov" for these programs. In a specific embodiment, percent identity is calculated using BLAST2 with default parameters as provided by the NCBI.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of definitive endoderm cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not definitive endoderm cells or their progeny as defined by the terms herein. In some embodiments, the present invention encompasses methods to expand a population of definitive endoderm cells, wherein the expanded population of definitive endoderm cells is a substantially pure population of definitive endoderm cells. Similarly, with regard to a "substantially pure" or "essentially purified" population of Pdx1-positive pancreatic progenitors, refers to a population of cells that contain fewer than about 20%, more preferably fewer than about 15%, 10%, 8%, 7%, most preferably fewer than about 5%, 4%, 3%, 2%, 1%, or less than 1%, of cells that are not Pdx1-positive pancreatic progenitors or their progeny as defined by the terms herein. In some embodiments, the present invention encompasses methods to expand a population of Pdx1-positive pancreatic progenitors, wherein the expanded population of Pdx1-positive pancreatic progenitors is a substantially pure population of Pdx1-positive pancreatic progenitors.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. In the context of a cell that is of endoderm origin or is "endodermal linage" this means the cell was derived from an endoderm cell and can differentiate along the endoderm lineage restricted pathways, such as one or more developmental lineage pathways which give rise to definitive endoderm cells, which in turn can differentiate into liver cells, thymus, pancreas, lung and intestine.

As used herein, the term "xenogeneic" refers to cells that are derived from different species.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term a "variant" in referring to a polypeptide could be, e.g., a polypeptide at least 80%, 85%, 90%, 95%, 98%, or 99% identical to full length polypeptide. The variant could be a fragment of full length polypeptide The variant could be a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest, such as the ability to detect the presence of a definitive endoderm cell or Pdx1-positive pancreatic progenitor. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

The term "functional fragments" as used herein is a polypeptide having amino acid sequence which is smaller in size than, but substantially homologous to the polypeptide it is a fragment of, and where the functional fragment polypeptide sequence is about at least 50%, or 60% or 70% or at 80% or 90% or 100% or greater than 100%, for example 1.5-fold, 2-fold, 3-fold, 4-fold or greater than 4-fold effective biological action as the polypeptide from which it is a fragment of. Functional fragment polypeptides may have additional functions that can include decreased antigenicity, increased DNA binding (as in transcription factors), or altered RNA binding (as in regulating RNA stability or degradation).

The term "vector" refers to a carrier DNA molecule into which a DNA sequence can be inserted for introduction into a host cell. Preferred vectors are those capable of autonomous replication and/or expression of nucleic acids to which they are linked Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

The terms "regulatory sequence" and "promoter" are used interchangeably herein, and refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

As used herein, the term "transcription factor" refers to a protein that binds to specific parts of DNA using DNA binding domains and is part of the system that controls the transfer (or transcription) of genetic information from DNA to RNA. As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyl-transferase (PAC), hygromycin resistance gene (hyg), multi-drug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as *luciferase* (e.g., firefly or *Renilla luciferase*) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

A "reporter gene" as used herein encompasses any gene that is genetically introduced into a cell that adds to the phenotype of the stem cell. Reporter genes as disclosed in this invention are intended to encompass fluorescent, luminescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny. A reporter gene is generally operatively linked to sequences that regulate its expression in a manner dependent upon one or more conditions which are monitored by measuring expression of the reporter gene. In some cases, expression of the reporter gene may be determined in live cells. Where live cell reporter gene assays are used, reporter gene expression may be monitored at multiple timepoints, e.g., 2, 3, 4, 5, 6, 8, or 10 or more timepoints. In some cases, where a live cell reporter assay is used, reporter gene expression is monitored with a frequency of at least about 10 minutes to about 24 hours, e.g., 20 minutes, 1 hour, 2 hours, 3 hours, 4 hours, 5 hours, 6 hours, 7 hours, 8 hours, 9 hours, 10 hours, 12 hours, 18 hours, or another frequency from any integer between about 10 minutes to about 24 hours.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "diabetes" and "diabetes mellitus" are used interchangeably herein. The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level 11.1 mmol/L or higher (200 mg/dL or higher). Other values suggestive of or indicating high risk for Diabetes Mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males: waist to hip ratio higher than 0.90; females: waist to hip ratio higher than 0.85) and/or body mass index exceeding 30 kg/m$^2$; microalbuminuria, where the urinary albumin excretion rate 20 µg/min or higher, or albumin: creatinine ratio 30 mg/g or higher). The term diabetes encompasses all forms of diabetes, e.g. Type I, Type II and Type 1.5.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

As used herein, the terms "administering," "introducing" and "transplanting" are used interchangeably in the context of the placement of cells, e.g. definitive endoderm cells or pdx1-positive pancreatic cells, or their differentiated progeny (e.g. insulin-producing cells or pancreatic β-cells or pancreatic β-like cells) of the invention into a subject, by a method or route which results in at least partial localization of the introduced cells at a desired site. The cells e.g. definitive endoderm cells or pdx1-positive pancreatic cells, or their differentiated progeny (e.g. insulin-producing cells or pancreatic β-cells or pancreatic β-like cells) an be implanted directly to the pancreas, or alternatively be administered by any appropriate route which results in delivery to a desired location in the subject where at least a portion of the implanted cells or components of the cells remain viable. The period of viability of the cells after administration to a subject can be as short as a few hours, e.g. twenty-four hours, to a few days, to as long as several years. In some instances, the cells can also be administered at a non-pancreatic location, such as in the liver or subcutaneously, for example, in a capsule to maintain the implanted cells at the implant location and avoid migration of the implanted cells.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The term "tissue" refers to a group or layer of specialized cells which together perform certain special functions. The term "tissue-specific" refers to a source of cells from a specific tissue.

The term "halogen" refers to any radical of fluorine, chlorine, bromine or iodine.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, S, S(O), or C(O). For example, $C_1$-$C_6$ indicates that the group may have from 1 to 6 (inclusive) carbon atoms in it. Exemplary alkyl groups include, but are not limited to, methyl, ethyl, propyl, isopropyl, butyl, t-butyl, and the like.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkylenyl" refers to a divalent group derived from a straight or branched chain alkyl. Exemplary alkylenyls include, but are not limited to, —$CH^2$—, —$CH(CH_3)$—, —$C(CH_3)_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH(CH_3)CH_2$—.

The term "alkenylenyl" refers to an alkylenyl that comprises at least one double bond.

The term "alkynylenyl" refers to an alkylenyl that comprises at least one triple bond.

The term "alkoxy" refers to an —O-alkyl radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "cyclyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, phenyl, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocycyll" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocycyll groups include, but are not limited to piperazinyl, pyrrolidinyl, dioxanyl, morpholinyl, tetrahydrofuranyl, and the like.

The term "optionally substituted" means that the specified group or moiety, such as an aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocycyll, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased","increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Stem Cells

Stem cells are cells that retain the ability to renew themselves through mitotic cell division and can differentiate into a diverse range of specialized cell types. The two broad types of mammalian stem cells are: embryonic stem (ES) cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

While certain embodiments are described below in reference to the use of stem cells for producing endoderm, e.g., definitive endoderm, germ cells may be used in place of, or with, the stem cells to provide endoderm, e.g., definitive endoderm, using similar protocols as the illustrative protocols described herein. Suitable germ cells can be prepared, for example, from primordial germ cells present in human fetal material taken about 8-11 weeks after the last menstrual period. Illustrative germ cell preparation methods are described, for example, in Shamblott et al., Proc. Natl. Acad. Sci. USA 95:13726, 1998 and U.S. Pat. No. 6,090,622.

ES cells, e.g., human embryonic stem cells (hESCs) or mouse embryonic stem cells (mESCs), with a virtually endless replication capacity and the potential to differentiate into most cell types, present, in principle, an unlimited starting material to generate the differentiated cells for clinical therapy (http://stemcells.nih.gov/info/scireport/2006report.htm, 2006). One possible application of ES cells is to generate new pancreatic beta cells for the cell replacement therapy of type I diabetics, by first producing endoderm, e.g., definitive endoderm, from, e.g., hESCs.

hESC cells, are described, for example, by Cowan et al. (N Engl. J. Med. 350:1353, 2004) and Thomson et al. (Science 282:1145, 1998); embryonic stem cells from other primates, Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998) may also be used in the methods disclosed herein. mESCs, are described, for example, by Tremml et al. (Curr Protoc Stem Cell Biol. Chapter 1:Unit 1C.4, 2008). The stem cells may be, for example, unipotent, totipotent, multipotent, or pluripotent. In some examples, any cells of primate origin that are capable of producing progeny that are derivatives of at least one germinal layer, or all three germinal layers, may be used in the methods disclosed herein.

In certain examples, ES cells may be isolated, for example, as described in Cowan et al. (N Engl. J. Med. 350:1353, 2004) and U.S. Pat. No. 5,843,780 and Thomson et al., Proc. Natl. Acad. Sci. USA 92:7844, 1995. For example, hESCs cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hESCs include their pluripotent derivatives, such as primitive ectoderm-like (EPL) cells, as outlined, for example, in WO 01/51610 (Bresagen). hESCs can also be obtained from human pre-implantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses can be isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers. After 9 to 15 days, inner cell mass-derived outgrowths can be dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology can be individually selected by micropipette, mechanically dissociated into clumps, and replated. ES-like morphology is characterized as compact colonies with apparently high nucleus to cytoplasm ratio and prominent nucleoli. Resulting hESCs can then be routinely split every 1-2 weeks, for example, by brief trypsinization, exposure to Dulbecco's PBS (containing 2 mM EDTA), exposure to type IV collagenase (about 200 U/mL; Gibco) or by selection of individual colonies by micropipette. In some examples, clump sizes of about 50 to 100 cells are optimal. mESCs cells can be prepared from using the techniques described by e.g., Conner et al. (Curr. Prot. in Mol. Biol. Unit 23.4, 2003).

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen).

Alternatively, in some embodiments, hES cells can be obtained from human preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

In some embodiments, human Embryonic Germ (hEG) cells are pluripotent stem cells which can be used in the methods as disclosed herein to differentiate into primitive endoderm cells. hEG cells can be used be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622, which is incorporated herein in its entirety by reference.

Briefly, genital ridges processed to form disaggregated cells. EG growth medium is DMEM, 4500 mg/L D-glucose, 2200 mg/L mM $NaHCO_3$; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/mL human recombinant bFGF (Genzyme); and 10 µM forskolin (in 10% DMSO). Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation ~0.2 mL of primary germ cell (PGC) suspension is added to each of the wells. The first passage is done after 7-10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7-30 days or 1-4 passages In certain examples, the stem cells can be undifferentiated (e.g. a cell not committed to a specific linage) prior to exposure to the compounds of Formula (I) and subsequently Formula (II) according to the methods as disclosed herein, whereas in other examples it may be desirable to differentiate the stem cells to one or more intermediate cell types prior to exposure of the compound(s) described herein. For example, the stems cells may display morphological, biological or physical characteristics of undifferentiated cells that can be used to distinguish them from differentiated cells of embryo or adult origin. In some examples, undifferentiated cells may appear in the two dimensions of a microscopic view in colonies of cells with high nuclear/cytoplasmic ratios and prominent nucleoli. The stem cells may be themselves (for example, without substantially any undifferentiated cells being present) or may be used in the presence of differentiated cells. In certain examples, the stem cells may be cultured in the presence of suitable nutrients and optionally other cells such that the stem cells can grow and optionally differentiate. For example, embryonic fibroblasts or fibroblast-like cells may be present in the culture to assist in the growth of the stem cells. The fibroblast may be present during one stage of stem cell growth but not necessarily at all stages. For example, the fibroblast may be added to stem cell cultures in a first culturing stage and not added to the stem cell cultures in one or more subsequent culturing stages.

Stem cells used in all aspects of the present invention can be any cells derived from any kind of tissue (for example embryonic tissue such as fetal or pre-fetal tissue, or adult tissue), which stem cells have the characteristic of being capable under appropriate conditions of producing progeny of different cell types, e.g. derivatives of all of at least one of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (Miz-Medi Hospital-Seoul National University); HSF-1, HSF-6 (University of California at San Francisco); and H1, H7, H9, H13, H14 (Wisconsin Alumni Research Foundation (WiCell Research Institute)). In some embodiments, the source of human stem cells or pluripotent stem cells used for chemically-induced differentiation into definitive endoderm cells did not involve destroying a human embryo.

In another embodiment, the stem cells can be isolated from tissue including solid tissue. In some embodiments, the tissue is skin, fat tissue (e.g. adipose tissue), muscle tissue, heart or cardiac tissue. In other embodiments, the tissue is for example but not limited to, umbilical cord blood, placenta, bone marrow, or chondral Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol.

Reprod. 55:254); and human embryonic germ (hEG) cells (Shambloft et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc. In some embodiments, a human embryo was not destroyed for the source of pluripotent cell used on the methods and compositions as disclosed herein.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see U.S. application Ser. No. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid GbS, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

A mixture of cells from a suitable source of endothelial, muscle, and/or neural stem cells can be harvested from a mammalian donor by methods known in the art. A suitable source is the hematopoietic microenvironment. For example, circulating peripheral blood, preferably mobilized (i.e., recruited) as described below, may be removed from a subject. Alternatively, bone marrow may be obtained from a mammal, such as a human patient, undergoing an autologous transplant. In some embodiments, stem cells can be obtained from the subjects adipose tissue, for example using the CELUTION™ SYSTEM from Cytori, as disclosed in U.S. Pat. Nos. 7,390,484 and 7,429,488 which is incorporated herein in its entirety by reference.

In some embodiments, human umbilical cord blood cells (HUCBC) are useful in the methods as disclosed herein. Human UBC cells are recognized as a rich source of hematopoietic and mesenchymal progenitor cells (Broxmeyer et al., 1992 Proc. Natl. Acad. Sci. USA 89:4109-4113). Previously, umbilical cord and placental blood were considered a waste product normally discarded at the birth of an infant. Cord blood cells are used as a source of transplantable stem and progenitor cells and as a source of marrow repopulating cells for the treatment of malignant diseases (i.e. acute lymphoid leukemia, acute myeloid leukemia, chronic myeloid leukemia, myelodysplastic syndrome, and nueroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). A distinct advantage of HUCBC is the immature immunity of these cells that is very similar to fetal cells, which significantly reduces the risk for rejection by the host (Taylor & Bryson, 1985J. Immunol. 134:1493-1497). Human umbilical cord blood contains mesenchymal and hematopoietic progenitor cells, and endothelial cell precursors that can be expanded in tissue culture (Broxmeyer et al., 1992 Proc. Natl. Acad. Sci. USA 89:4109-4113; Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503; Taylor & Bryson, 1985J. Immunol. 134: 1493-1497 Broxmeyer, 1995 Transfusion 35:694-702; Chen et al., 2001 Stroke 32:2682-2688; Nieda et al., 1997 Br. J. Haematology 98:775-777; Erices et al., 2000 Br. J. Haematology 109:235-242). The total content of hematopoietic progenitor cells in umbilical cord blood equals or exceeds bone marrow, and in addition, the highly proliferative hematopoietic cells are eightfold higher in HUCBC than in bone marrow and express hematopoietic markers such as CD14, CD34, and CD45 (Sanchez-Ramos et al., 2001 Exp. Neur. 171:109-115; Bicknese et al., 2002 Cell Transplantation 11:261-264; Lu et al., 1993 J. Exp Med. 178:2089-2096).

In another embodiment, pluripotent cells are cells in the hematopoietic micro-environment, such as the circulating peripheral blood, preferably from the mononuclear fraction of peripheral blood, umbilical cord blood, bone marrow, fetal liver, or yolk sac of a mammal. The stem cells, especially neural stem cells, may also be derived from the central nervous system, including the meninges.

In another embodiment, pluripotent cells are present in embryoid bodies are formed by harvesting ES cells with brief protease digestion, and allowing small clumps of undifferentiated human ESCs to grow in suspension culture. Differentiation is induced by withdrawal of conditioned medium. The resulting embryoid bodies are plated onto semi-solid substrates. Formation of differentiated cells may be observed after around about 7 days to around about 4 weeks. Viable differentiating cells from in vitro cultures of stem cells are selected for by partially dissociating embryoid bodies or similar structures to provide cell aggregates. Aggregates comprising cells of interest are selected for phenotypic features using methods that substantially maintain the cell to cell contacts in the aggregate.

In an alternative embodiment, the stem cells can be reprogrammed stem cells, such as stem cells derived from somatic or differentiated cells. In such an embodiment, the de-differentiated stem cells can be for example, but not limited to, neoplastic cells, tumor cells and cancer cells or alternatively induced reprogrammed cells such as induced pluripotent stem cells or iPS cells.

Cloning and Cell Culture

Illustrative methods for molecular genetics and genetic engineering that may be used in the technology described herein may be found, for example, in current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found, for example, in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons.). Illustrative reagents, cloning vectors, and kits for genetic manipulation may be commercially obtained, for example, from BioRad, Stratagene, Invitrogen, ClonTech, and Sigma-Aldrich Co.

Suitable cell culture methods may be found, for example, in Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Suitable tissue culture supplies and reagents are commercially available, for example, from Gibco/BRL, Nalgene-Nunc International, Sigma Chemical Co., and ICN Biomedicals.

Pluripotent stem cells can be propagated by one of ordinary skill in the art and continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM .beta.-mercaptoethanol. Just before use, human bFGF is added to 4 ng/mL (WO 99/20741, Geron Corp.). Traditionally, ES cells are cultured on a layer of feeder cells, typically fibroblasts derived from embryonic or fetal tissue.

Scientists at Geron have discovered that pluripotent SCs can be maintained in an undifferentiated state even without feeder cells. The environment for feeder-free cultures includes a suitable culture substrate, particularly an extracellular matrix such as Matrigel® or laminin. Typically, enzymatic digestion is halted before cells become completely dispersed (say, .about.5 min with collagenase IV). Clumps of ~10 to 2,000 cells are then plated directly onto the substrate without further dispersal.

Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~5-6×10$^4$ cm$^{-2}$ in a serum free medium such as KO DMEM supplemented with 20% serum replacement and 4 ng/mL bFGF. Medium that has been conditioned for 1-2 days is supplemented with further bFGF, and used to support pluripotent SC culture for 1-2 days. Features of the feeder-free culture method are further discussed in International Patent Publication WO 01/51616; and Xu et al., Nat. Biotechnol. 19:971, 2001.

Under the microscope, ES cells appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present human embryonal carcinoma (hEC) cells. Differentiation of pluripotent SCs in vitro results in the loss of SSEA-4, Tra-1-60, and Tra-1-81 expression, and increased expression of SSEA-1, which is also found on undifferentiated hEG cells.

In accordance with certain examples, several approaches may combined with methods of the invention to differentiate the stem cells to endoderm cells. In one approach, the stem cells may be plated onto a new substrate or the medium may be exchanged to remove extracellular matrix or soluble factors that inhibit differentiation. This is sometimes referred to as the "direct differentiation method", and is described in general terms in International patent publication WO 01/51616, and U.S. Patent Publication 2002/0019046, which is incorporated herein in its entirety by reference. It is usually preferable in the direct differentiation method to begin with a feeder-free culture of stem cells, so as to avoid potential complications in the differentiation process caused by residual feeder cells. Another approach is to put undifferentiated stem cells in suspension culture, which will frequently cause them to form aggregates of differentiated and undifferentiated cells. For example, stem cells can be harvested by brief collagenase digestion, dissociated into clusters, and passaged in non-adherent cell culture plates. The aggregates can be fed every few days, and then harvested after a suitable period, typically 4-8 days. Depending on the conditions, aggregates generally start by forming a heterogeneous population of cell types, including a substantial frequency of endoderm cells. The aggregates can then be dispersed and replated for the next stage in the differentiation process, on substrates such as laminin or fibronectin; or passaged in suspension culture using, for example, non-adherent plates and a suitable medium. In some instances, differentiation can take place in the presence of one or more of the compounds of Formula (I) or Formula (II) as described herein, e.g., IDE1 and/or IDE2.

Direct differentiation or differentiation in aggregates can be monitored for the presence of endoderm cells using suitable markers such as those listed in U.S. Pat. No. 7,326,572. In some preferred embodiments, differentiation can be monitored for the presence of endoderm cells using markers such as Sox17. Once a sufficient proportion of endoderm is obtained, cells can be replated or otherwise manipulated to begin another stage of differentiation. In certain circumstances, differentiation or maintenance of cells may be enhanced if the cells are kept in micromass clusters (for example, 50 to 5,000 cells).

Compounds for Inducing the Differentiation of Pluripotent Stem Cells to Definitive Endoderm Cells One aspect of the present invention provides methods of producing an endoderm cell, e.g. a definitive endoderm cell by contacting (e.g., culturing) a pluripotent stem cell with a compound of Formula (I) as described herein. Accordingly, in some embodiments any compound with Formula (I) useful in the methods and compositions as disclosed herein are cell permeable small molecules, and can control cellular processes by modulating signal transduction pathways, gene expression or metabolism and have been effectively used in stem cell differentiation protocols. Small molecules can be synthesized in high quantity and purity as well as conveniently supplied or removed, giving them great potential to be useful for therapeutic applications. High throughput screens have been performed to identify novel small molecules that can support the self renewal of ES cells (Chen et al., 2006; Desbordes et al., 2008), cardiogenic specification of mouse ES cells (Wu et al., 2004) or neural progenitor cells (Diamandis et al., 2007) as well as inducing specific cell types, notably neuronal and muscle cells (reviewed by (Ding and Schultz, 2004).

In one embodiment, a pluripotent stem cell, such as a human pluripotent stem cell is contacted with at least one compound of Formula (I) to differentiate the pluripotent stem cell into endoderm, such as definitive endoderm.

In one aspect, the invention provides a method of producing a definitive endoderm cell from a pluripotent stem cell comprising contacting a population of pluripotent stem cells with at least one compound of Formula (I) to induce the differentiation of at least one pluripotent stem cell into a definitive endoderm cell, wherein the definitive endoderm cell expresses Sox17, or HNF3B (FoxA2), or Sox17 and HNF3B (FoxA2) and wherein the compound of formula (I) is:

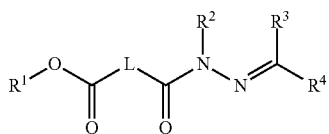

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

In some embodiments, $R^1$ is H or $C_1$-$C_6$ alkyl. Preferred alkyls for $R^1$ include methyl, ethyl, propyl, isopropyl or t-butyl. Preferably $R^1$ is H.

In some embodiments, $R^2$ is H or $C_1$-$C_6$ alkyl. Preferred alkyls for $R^2$ include methyl, ethyl, propyl, isopropyl or t-butyl.

In some embodiments, $R^3$ is H or an optionally substituted aryl or heteroaryl. A preferred aryl for $R^3$ is an optionally substituted phenyl. Preferably $R^3$ is a phenyl substituted with —C(O)OR$^5$, where $R^5$ is H, alkyl, alkenyl, alkynyl, aryl, heteroaryl, cyclyl, or cyclyl, each of which can be optionally substituted. Preferably, $R^5$ is H, methyl, ethyl, or t-butyl.

In one embodioment, $R^3$ is

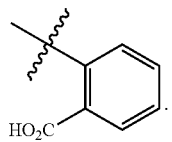

In some embodiments, $R^4$ is H or $C_1$-$C_6$ alkyl. Preferred alkyls for $R^4$ include methyl, ethyl or propyl.

In some embodiments, $R^3$ and $R^4$ together with the carbon to which they are attached form an optionally substituted cyclyl or heterocycyll. In one embodiment, $R^3$ and $R^4$ together with the carbon to which they are attached form a 5-8 membered cyclyl. Preferably cyclyl is a 5 membered.

In some embodiments, L is a $C_1$-$C_{10}$ alkylenyl. Preferably L is —$CH_2CH_2CH_2CH_2CH_2$—.

In a preferred compound of formula (I), $R^1$, $R^2$, and $R^4$ are H and $R^3$ is an optionally substituted aryl or heteroaryl.

In another preferred compound of formula (I), $R^1$ and $R^2$ are H and $R^3$ and $R^4$ together with the carbon they are attached to form an optionally substituted 5-8 membered cyclyl of heterocylyl.

One preferred compound of formula (I) is IDE1, wherein IDE1 has the following structure:

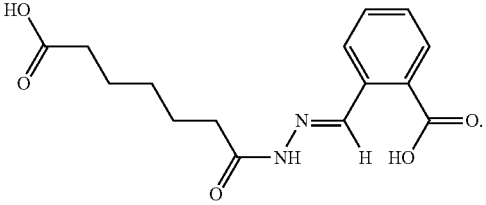 [SMILES: O=C(O)CCCCCC(=O)N/N=C/c1ccccc1C(=O)O]

Another preferred compound of formula (I) is IDE2, wherein IDE2 has the following structure:

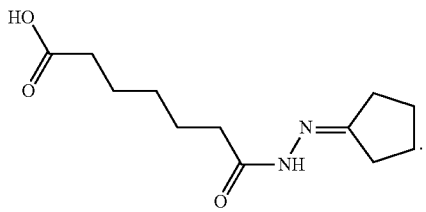 [SMILES: O=C(O)CCCCCC(=O)NN=C1CCCC1]

In alternative embodiments, a pluripotent stem cell, such as a human pluripotent stem cell is contacted with at least one histone deacetylase (HDAC) inhibitor (e.g., a class I/II HDAC inhibitor) to differentiate the pluripotent stem cell into endoderm, such as definitive endoderm. Histone deacetylase (HDAC) are a class of enzymes that remove acetyl groups from an ε-N-acetyl lysine amino acid on a histone. Exemplary HDACs include those Class I HDAC: HDAC1, HDAC2, HDAC3, HDAC8; and Class II HDACs: HDAC4, HDACS, HDAC6, HDAC7A, HDAC9, HDAC10. Type I mammalian HDACs include: HDAC1, HDAC2, HDAC3, HDAC8, and HDAC11. Type II mammalian HDACs include: HDAC4, HDACS, HDAC6, HDAC7, HDAC9, and HDAC1.

A number of structural classes of negative regulators of HDACs (e.g., HDAC inhibitors) have been developed, for example, small molecular weight carboxylates (e.g., less than about 250 amu), hydroxamic acids, benzamides, epoxyketones, cyclic peptides, and hybrid molecules. (See, for example, Drummond D C, Noble C O, Kirpotin D B, Guo Z, Scott G K, et al. (2005) Clinical development of histone deacetylase inhibitors as anticancer agents. Annu Rev Pharmacol Toxicol 45: 495-528, (including specific examples therein) which is hereby incorporated by reference in its entirety). Non-limiting examples of negative regulators of type I/II HDACs include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (i.e., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (i.e., 6-(3-chlorophenylureido)caproic hydroxamic acid), AOE (2-amino-8-oxo-9,10-epoxydecanoic acid), CHAP31, CHAP 50, IDE1 and IDE2. Other inhibitors include, for example, dominant negative forms of the HDACs (e.g., catalytically inactive forms) siRNA inhibitors of the HDACs, and antibodies that specifically bind to the HDACs. Inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich. In some embodiments, IDE1 or IDE2 is a preferred histone deacetylase inhibitor.

In some embodiments of this aspect of the present invention provides methods of producing a definitive endoderm cell by contacting (e.g., culturing) a pluripotent stem cell, e.g. an iPS cell or embryonic stem cell with a compound of Formula (I) as described herein, wherein the a pluripotent stem cell is contacted with a compound of Formula (I) at a concentration of about between 25 nM to 10 µM, or between about 25 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 5 µm, or about 5 µM to 10 µM.

In some embodiments, methods of producing a definitive endoderm cell by contacting (e.g., culturing) a pluripotent stem cell, e.g. an iPS cell or embryonic stem cell with a compound of Formula (I) at a concentration of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM. In some embodiments, a pluripotent stem cell is contacted (e.g. cultured) with a compound of Formula (I) at a concentration of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM.

In some embodiments, a pluripotent stem cell is contacted (e.g. cultured) with a compound of Formula (I) which is IDE1, such that the pluripotent stem cell is differentiated into a definitive endoderm cell by contacting (e.g. culturing) the pluripotent stem cell with IDE1 at a concentration of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-100 nM, or any integer between 50-150 nM, or any integer between 100 nM-200 nM or any integer between 200 nM-500 nM. In some embodiments, the pluripotent stem cell is contacted with a compound of IDE1 at a concentration of about 100 nM to differentiate the pluripotent stem cell into a definitive endoderm cell.

In some embodiments, a pluripotent stem cell is contacted (e.g. cultured) with a compound of Formula (I) which is IDE2, such that the pluripotent stem cell is differentiated into a definitive endoderm cell by contacting (e.g. culturing) the pluripotent stem cell with IDE2 at a concentration of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-200 nM, or any integer between 100-300 nM, or any integer between 100 nM-500 nM or any integer between about 200 nM-500 nM. In some embodiments, the pluripotent stem cell is contacted with a compound of IDE2 at a concentration of about 200 nM to differentiate the pluripotent stem cell into a definitive endoderm cell.

In some embodiments, a population of pluripotent stem cells can be contacted or exposed to one or more of the compounds of Formula (I), e.g. IDE1 or IDE2 as described herein alone, and in other embodiments, a population of pluripotent stem cells can be contacted with at least one additional agent, either concurrent with (e.g. in combination with), subsequent to or prior to the contact of the pluripotent cell with a compound of Formula (I). In some embodiments, the additional compound for use in combination with compounds of Formula (I) can include, but is not limited to agents of transforming growth factor-13 (TGF-β) family member (e.g., Nodal or Activin A), fibroblast growth factor (FGF) family member (e.g., FGF10), Wnt growth factor family member (e.g., Wnt3a), bone morphogenic proteins (BMPs) and/or members of the AKT/PI3K pathway. The definition and details of the TGF-β/BMP pathway are disclosed in the art e.g., Kawabata M. and Miyazono K., J. Biochem. (Tokyo), 125, 9-16 (1999); Wrana J. L., Miner. Electrolyte Metab., 24, 120-130 (1998); and Markowitz S. D., and Roberts A. B., Cytokine Growth Factor Rev., 7, 93-102 (1996). In some embodiments, a pluripotent stem cell can be exposed to a compound of Formula (I), e.g. IDE1 and/or IDE2 in combination with at least one additional compounds or factors including, but not limited to cyclopamine, TGF family members (TGF-alpha., Activin A, Activin B, TGF-beta-1, TGF-beta-3), exendin 4, nicotinamide, n-butyrate, DMSO, all-trans retinoic acid, GLP-I, bone morphogenic proteins (BMP-2, BMP-5, BMP-6, BMP-7), insulin-like growth factors (IGF-I, IGF-II), fibroblast growth factor (FGF7, FGF10, bFGF, FGF4), other growth factors (EGF, βcellulin, growth hormone, HGF), other hormones (prolactin, cholecytokinin, gastrin I, placental lactogen), TGF-β. family antagonists (Noggin, follistatin, chordin), IBMX, wortmannin, dexamethazone, Reg, INGAP, cAMP or cAMP activators (forskolin), and/or extracellular matrix components (laminin, fibronectin).

Endoderm Cells and Definitive Endoderm Cells

In certain examples, the agents such as compounds of Formula (I) can be used to induce the differentiation of pluripotent stem cells into endoderm cells, e.g., definitive endoderm cells by exposing or contacting a population of pluripotent stem cells with an effective amount of at least one compound of Formula (I) as described herein to differentiate the stem cells into an endoderm cell, e.g., a definitive endoderm cell. Accordingly, included herein are cells and compositions made by the methods described herein. The exact amount and type of compound of Formula (I) can vary depending on the number of pluripotent stem cells, the desired differentiation stage and the number of prior differentiation stages that have been performed.

In certain examples, a compound of Formula (I) is present in an effective amount. As used herein, "effective amount" refers to the amount of the compound that should be present for the differentiation of at least 10% or at least 20% or at least 30% of the cells in a population of pluripotent stem cell, e.g. an ES cells or iPS cells into endoderm cells, such as definitive endoderm cells. In additional examples, a compound of Formula (I) such as IDE1 or IDE2 can be present in the culture medium of the pluripotent stem cells e.g. the ES cells, or alternatively, the compounds of Formula (I) such as IDE1 or IDE2 may be added to the ES cells during some stage of growth. In some examples, a compound of Formula (I), e.g., IDE1 and/or IDE2 is used to produce the pancreatic cells or pancreatic cell precursors, and the HDAC inhibitor(s), e.g., IDE1 and/or IDE2 can be present in a concentration of about 10 µM/liter or less, for example about 1 µM/liter or less. In certain examples, a population of pluripotent stem cells can be exposed to at least one compound of Formula (I), e.g. IDE1 and/or IDE2 prior to any differentiation or during the first stage of differentiation.

Endoderm is one of the germ layers formed during animal embryogenesis. Cells generally migrate inward along the archenteron from the inner layer of the gastrula, which develops into the endoderm. Exemplary products produced by the endoderm include: gastrointestinal tract, respiratory tract, endocrine glands and organs (e.g., liver and pancreas). The endoderm generally consists at first of flattened cells, which subsequently become columnar. It can form the epithelial lining of the whole of the digestive tube except part of the mouth, pharynx and the terminal part of the rectum (which are lined by involutions of the ectoderm), the lining cells of all the glands which open into the digestive tube, including those of the liver and pancreas, the epithelium of the auditory tube and tympanic cavity, of the trachea, bronchi, and alveoli of the lungs, of the urinary bladder and part of the urethra, and that which lines the follicles of the thyroid gland and thymus.

Exemplary studies of the developmental pathways that control endoderm formation have been conducted in *Xenopous laevis*, zebrafish and mice (reviewed by Wells and Melton, 1999; Lewis and Tam, 2006). Collectively, these studies suggest a conserved mechanism for endoderm/mesoderm commitment utilizing the transforming growth factor-β (TGF-β) family member Activin A and Nodal, fibroblast growth factor (FGF) and Wnt growth factor families. Similarly, in vitro application of Activin A or Nodal to mouse or human ES cell cultures leads to endoderm induction (Kubo et al., 2004; Yasunaga et al., 2005; D'Amour et al., 2005). Other molecules that influence endoderm formation in vitro include WNTs (D'Amour et al., 2005), bone morphogenic proteins (BMPs), and members of the AKT/PI3K pathway (McLean et al., 2007).

In certain examples, a method of inducing the differentiation of pluripotent stem cells, e.g. embryonic stem cells to endoderm cells, e.g., definitive endoderm cells, is provided. In some examples, the method comprises providing a pluripotent stem cell, e.g. an embryonic stem cell and providing at least one compound of Formula (I) as described herein to differentiate the pluripotent stem cell, e.g. an embryonic stem cell, to provide the endoderm cell, e.g. a definitive endoderm cell, upon exposure of the pluripotent stem cell to the compound. In certain examples, the compound may be present in an effective amount in the culture medium or may be added to the culture medium at a desired stage. In some examples, the compound may be IDE1 and/or IDE2. In certain examples, a population of pluripotent stem cells may be exposed to a compound of Formula (I) prior to any differentiation or during the first stage of differentiation.

In certain embodiments, a method of producing an endoderm cell, e.g., a definitive endoderm cell from a pluripotent stem cells, e.g. an embryonic stem cells is disclosed. In one example, the method comprises culturing the pluripotent stem cell, e.g. an embryonic stem cells in a culture medium comprising an effective amount of at least one compound of Formula (I) as described herein, e.g. IDE1 and/or IDE2, to induce and cause the differentiation of at least one pluripotent stem cell into an endoderm cell, e.g., a definitive endoderm cell. In certain examples, the compound of Formula (I) is IDE1 and/or IDE2. In some embodiments, a population of pluripotent stem cells are cultured in the presence of the compound of Formula (I) prior to any differentiation or during the first stage of differentiation.

In certain examples, a method of producing endoderm, e.g., definitive endoderm, by culturing stem cells in the presence of an effective amount of at least one compound of Formula (I), such as IDE1 or IDE2 described herein is provided to thereby produce an endoderm cell, e.g., an definitive endoderm cell is provided. One can use any pluripotent stem cell, such as a human pluripotent stem cell, or a human iPS cell or any of pluripotent stem cell as discussed herein or other suitable pluripotent stem cells. In some embodiments, a compound of Formula (I) as described herein can be present in the culture medium of a population of pluripotent stem cells or may be added in bolus or periodically during growth (e.g. replication or propagation) of the population of pluripotent stem cells. In certain examples, a population of pluripotent stem cells can be exposed to at least one compound of Formula (I) prior to any differentiation. In other examples, a population of pluripotent stem cells may be exposed to at least one compound of Formula (I) e.g. IDE1 or IDE2 during the first stage of differentiation.

Confirmation of the Presence and the Identification of a Definitive Endoderm Cell One can use any means common to one of ordinary skill in the art to confirm the presence of an endoderm cell, e.g. a definitive endoderm cell produced the induction of the differentiation of a pluripotent stem cell by exposure to a compound of Formula (I), such as IDE1 and/or IDE2. In some embodiments, the presence of endoderm cells can be detected using suitable markers such as those listed in U.S. Pat. No. 7,326,572, which is incorporated herein by reference.

Figure 4:
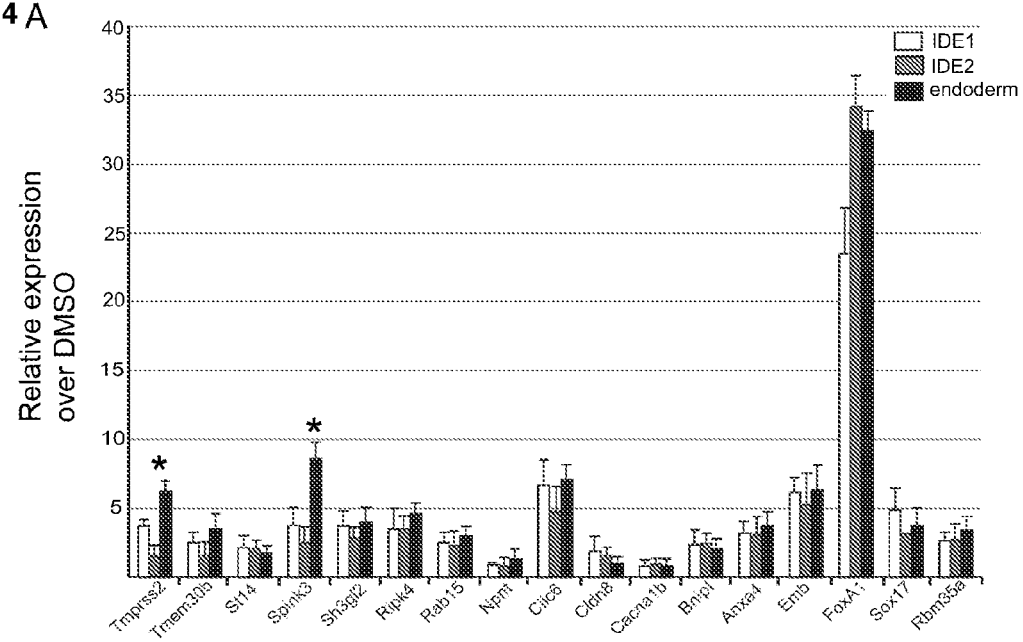
FIG. 4A-4B shows gene expression analysis of IDE1 or IDE2 chemically induced endoderm cells.
Figure 4:
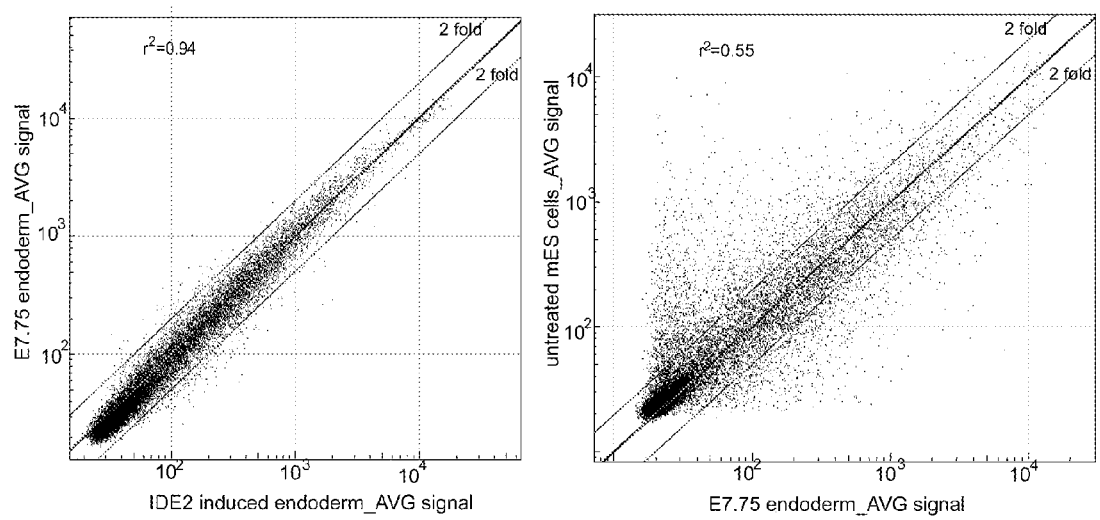

In some embodiments, the presence of definitive endoderm markers, e.g. chemically induced definitive endoderm cells, can be done by detecting the presence or absence of one or more markers indicative of an definitive endoderm cell. In some embodiments, the method can include detecting the positive expression (e.g. the presence) of a marker for definitive endoderm cells. In some embodiments, the marker can be detected using a reagent, e.g., a reagent for the detection of SOX17, HNF3β (Fox2A), MIXL2, GATA4, GSC, FGF17, VWF, CALCR, FOXQ1, CMKOR1, CRIP1. In particular, definitive endoderm cells herein express Sox17 and/or HNF3B, and do not express significant levels of extra-embryonic endoderm markers GATA4, SPARC, APF or DAB. Other positive markers for definitive endoderm cells also include, for example as shown in FIG. 4A, Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1 and Rbm35a. Negative markers (e.g. the absence of significant levels of expression) for definitive endoderm cells include extra-embryonic (EE) endoderm markers such as Gata4, SPARC, APF and DAB, as well as negative markers Zic, Pax6, Flk1 or CD31. Negative markers of definitive endoderm cells are useful for the purposes of negative selection of non-definitive endoderm cells (e.g. selection and discarding cells which express Gata4, SPARC, APF, DAB, Zic, Pax6, Flk1 or CD31) or for identification of cells which do not express these negative markers (e.g. definitive endoderm cells). A reagent for a marker can be, for example, an antibody against the marker or primers for a RT-PCR or PCR reaction, e.g., a semi-quantitative or quantitative RT-PCR or PCR reaction. Such markers can be used to evaluate whether a definitive endoderm cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of a pluripotent stem cell to a definitive endoderm can be monitored by determining the expression of markers characteristic of definitive endoderm cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of definitive endoderm cells as well as the lack of significant expression of markers characteristic of the pluripotent stem cell from which it was derived is determined.

As described in connection with monitoring the production of a definitive endoderm cell from a pluripotent stem cell, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. Additionally, it will be appreciated that at the polypeptide level, many of the markers of pancreatic islet hormone-expressing cells are secreted proteins. As such, techniques for measuring extracellular marker content, such as ELISA, may be utilized.

In other embodiments, the expression of Tmprss2, Tmem30b, St14, Spink3, Sh3gl2, Ripk4, Rab15, Npnt, Clic6, Cldn8, Cacna1b, Bnip1, Anxa4, Emb, FoxA1, Fox2A, Sox17 and Rbm35a in a definitive endoderm cell is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10.000-fold higher than the expression of Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Fox2A, Sox17 and Rbm35a in a pluripotent stem cell from which the definitive endoderm cell was derived.

The chemically induced reprogrammed cells as disclosed herein can express any number of pluripotent cell markers, including: Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1 and Rbm35a and other general markers for definitive endoderm cells, etc. Other markers can include the absence of expression of extra-embryonic endoderm cell markers, such as but not limited to Gata4, Sparc, AFP and Dab. Other markers include the absence or expression of Zic, Pax6, Flk1 or CD31. Definitive endoderm cells can also be characterized by the down-regulation of markers characteristic of the pluripotent stem from which the definitive endoderm cell is induced from. For example, definitive endoderm cells derived from pluripotent stem cell may be characterized by a statistically significant down-regulation of the pluripotent stem cell markers alkaline phosphatase (AP), NANOG, OCT-4, SOX-2, SSEA4, TRA-1-60 or TRA-1-81 in the definitive endoderm relative to the expression in the pluripotent stem cell from which it was derived. Other markers expressed by pluripotent cell markers, include but are not limited to alkaline phosphatase (AP); ABCG2; stage specific embryonic antigen-1 (SSEA-1); SSEA-3; SSEA-4; TRA-1-60; TRA-1-81; Tra-2-49/6E; ERas/ECATS, E-cadherin; .beta.III-tubulin; .alpha.-smooth muscle actin (.alpha.-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPAS/ECAT2; ECAT3; ECAT6; ECAT7; ECAT8; ECAT9; ECAT10; ECAT15-1; ECAT15-2; Fth117; Sa114; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; Dnmt3L; Sox15; Stat3; Grb2; SV40 Large T Antigen; HPV16 E6; HPV16 E7, β-catenin, and Bmi1 and other general markers for pluripotency, etc, and at least one or more of these are down regulated by a statistically significant amount in a definitive endoderm cell as compared to the pluripotent stem cell from which they were derived.

It is understood that the present invention is not limited to those markers listed as definitive endoderm markers herein, and the present invention also encompasses markers such as cell surface markers, antigens, and other gene products including ESTs, RNA (including microRNAs and antisense RNA), DNA (including genes and cDNAs), and portions thereof. Markers of definitive endoderm can be used, for example where a definitive endoderm cell expresses at least one marker from an endoderm cell. Markers of endoderm cells (which are distinct from definitive endoderm cells) include, Gata4, FoxA2, PDX1, Nodal, Sox7 and Sox17. By way of completeness, markers of mesoderm cells include, Brachycury, GSC, LEF1, Mox1 and Tie1. Markers of ectoderm cells include cripto1, EN1, GFAP, Islet 1, LIM1 and Nestin. Antibodies to markers of the three germ layers are commercially available, such as available from Abcam and other commercial antibody companies.

In some embodiments, a population of definitive endoderm cells can be replated or otherwise manipulated to begin another stage of differentiation. In certain circumstances, differentiation or maintenance of cells may be enhanced if the cells are kept in micromass clusters (for example, 50 to 5,000 cells), so that alpha, beta, and delta cells can interact directly.

Enrichment and Isolation and Purification of a Definitive Endoderm Cell

Another aspect of the present invention relates to the isolation of a population of definitive endoderm cells from a heterogeneous population of cells, such a mixed population of cells comprising definitive endoderm cells and pluripotent stem cells from which the definitive endoderm cells were derived. A population of definitive endoderm produced by any of the above-described processes can be enriched, isolated and/or purified by using any cell surface marker present on the definitive endoderm which is not present on the pluripotent stem cell from which it was derived. Such cell surface markers are also referred to as an affinity tag which is specific for a definitive endoderm cell. Examples of affinity tags specific for definitive endoderm cells are antibodies, ligands or other binding agents that are specific to a marker molecule, such as a polypeptide, that is present on the cell surface of a definitive endoderm cell but which is not substantially present on other cell types (e.g. on pluripotent stem cells). In some processes, an antibody which binds to a cell surface antigen on a definitive endoderm (e.g. a human definitive endoderm cell) is used as an affinity tag for the enrichment, isolation or purification of chemically induced (e.g. by contacting with a compound Formula I, e.g. IDE1 and/or IDE2) definitive endoderm cells produced by the methods described herein. Such antibodies are known and commercially available.

The skilled artisan will readily appreciate that the processes for making and using antibodies for the enrichment, isolation and/or purification of definitive endoderm cells are also readily adaptable for the enrichment, isolation and/or purification of definitive endoderm cells. For example, in some embodiments, the reagent, such as an antibody, is incubated with a cell population comprising definitive endoderm cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FITC-conjugated antibody that is capable of binding to the primary antibody. The definitive endoderm cells are then washed, centrifuged and resuspended in buffer. The definitive endoderm cell suspension is then analyzed and sorted using a fluorescence activated cell sorter (FACS). Antibody-bound, fluorescent reprogrammed cells are collected separately from non-bound, non-fluorescent cells (e.g. non-definitive endoderm cells), thereby resulting in the isolation of definitive endoderm cells from pluripotent stem cells or non-definitive endoderm cells (e.g. endoderm cells or differentiated cell types).

In another embodiments of the processes described herein, the isolated cell composition comprising definitive endoderm cells can be further purified by using an alternate affinity-based method or by additional rounds of sorting using the same or different markers that are specific for definitive endoderm cells. For example, in some embodiments, FACS sorting is used to first isolate a definitive endoderm cell which expresses at least one of: Sox17 or Fox2A (HNF3β), either alone or with a marker selected from the group of Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Fox2A, Sox17 and Rbm35a from cells that do not express one of those markers (e.g. negative cells) in the cell population. A second FAC sorting, e.g. sorting the positive cells again using FACS to isolate cells that are positive for a different marker than the first sort (e.g. selecting for cells which are positive for at least one of: Sox17 or Fox2A (HNF3β) or Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Fox2A, Sox17 and Rbm35a, where the selected marker is different to the first sort) enriches the cell population for reprogrammed cells.

In an alternative embodiment, FACS sorting is used to separate cells by negatively sorting for a marker that is present on most pluripotent stem cells, or a marker which not present on the definitive endoderm cells. For example, one can negatively select for cells which express at least one of Gata4, SPARC, APF or DAB, or Zic, Pax6, Flk1 or CD31 and discard these cells which express Gata4, SPARC, APF, DAB, Zic, Pax6, Flk1 or CD31 and collect the cells which have negative expression of at least one of Gata4, SPARC, APF, DAB, Zic, Pax6, Flk1 r CD31.

In some embodiments of the processes described herein, definitive endoderm cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above. For example, in some embodiments, at least one copy of a nucleic acid encoding GFP or a biologically active fragment thereof is introduced into a pluripotent stem cell which is to be chemically induced into a definitive endoderm cell, where a downstream of a promoter expressed in a definitive endoderm cell, such as the Sox17 promoter, such that the expression of the GFP gene product or biologically active fragment thereof is under control of the Sox17 promoter. In some embodiments, the entire coding region of the nucleic acid, which encodes Sox17 is replaced by a nucleic acid encoding GFP or a biologically active fragment thereof. In other embodiments, the nucleic acid encoding GFP or a biologically active fragment thereof is fused in frame with at least a portion of the nucleic acid encoding Sox17, thereby generating a fusion protein. In such embodiments, the fusion protein retains a fluorescent activity similar to GFP.

In addition to the procedures just described, chemically induced definitive endoderm cells may also be isolated by other techniques for cell isolation. Additionally, definitive endoderm cells may also be enriched or isolated by methods of serial subculture in growth conditions which promote the selective survival or selective expansion of the definitive endoderm cells. Such methods are known by persons of ordinary skill in the art.

Using the methods described herein, enriched, isolated and/or purified populations of definitive endoderm cells can be produced in vitro from pluripotent stem cells. Some preferred enrichment, isolation and/or purification methods relate to the in vitro production of human definitive endoderm cells from human pluripotent stem cells, or from human induced pluripotent stem (iPS) cells. In such an embodiment, where definitive endoderm cells are derived from iPS cells, the definitive endoderm cells can be autologous to the subject from whom the cells were obtained to generate the iPS cells.

Using the methods described herein, isolated cell populations of definitive endoderm cells are enriched in definitive endoderm content by at least about 2- to about 1000-fold as compared to a population of cells before the chemical induction of a pluripotent stem cell population. In some embodiments, definitive endoderm cells can be enriched by at least about 5- to about 500-fold as compared to a population before the chemical induction of a pluripotent stem cell population. In other embodiments, definitive endoderm cells can be enriched from at least about 10- to about 200-fold as compared to a population before the chemical induction of a pluripotent stem cell population. In still other embodiments, definitive endoderm cells can be enriched from at least about 20- to about 100-fold as compared to a population before the chemical induction of a pluripotent stem cell population. In yet other embodiments, definitive endoderm cells can be enriched from at least about 40- to about 80-fold as compared to a population before the chemical induction of a pluripotent stem cell population. In certain embodiments, definitive endoderm cells can be enriched from at least about 2- to about 20-fold as compared to a population before the chemical induction of a pluripotent stem cell population.

Compositions Comprising Definitive Endoderm Cells

Some embodiments of the present invention relate to cell compositions, such as cell cultures or cell populations, comprising definitive endoderm cells, wherein the definitive endoderm cells which have been derived from pluripotent stem cells e.g. human pluripotent stem cells. In accordance with certain embodiments, the chemically induced definitive endoderm cells are mammalian cells, and in a preferred embodiment, such definitive endoderm cells are human definitive endoderm cells.

Other embodiments of the present invention relate to compositions, such as an isolated cell population or cell culture, comprising definitive endoderm cells produced by the methods as disclosed herein. In some embodiments of the present invention relate to compositions, such as isolated cell populations or cell cultures, comprising chemically-induced definitive endoderm cells produced by the methods as disclosed herein. In such embodiments, the definitive endoderm cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the definitive endoderm cell population. In some embodiments, the composition comprises a population of definitive endoderm cells which make up more than about 90% of the total cells in the cell population, for example about at least 95%, or at least 96%, or at least 97%, or at least 98% or at least about 99%, or about at least 100% of the total cells in the cell population are definitive endoderm cells.

Certain other embodiments of the present invention relate to compositions, such as an isolated cell population or cell cultures, comprise a combination of definitive endoderm cells and the pluripotent stem cells from which the definitive endoderm cells were derived. In some embodiments, the pluripotent stem cells from which the definitive endoderm cells are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present invention relate to compositions, such as isolated cell populations or cell cultures, produced by the processes described herein and which comprise chemically induced definitive endoderm cells as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% definitive endoderm cells.

In another embodiment, isolated cell populations or compositions of cells (or cell cultures) comprise human definitive endoderm cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about IT %, at least about 10%, at least about 9%, at least about 8%, at least about 7%, at least about 6%, at least about 5%, at least about 4%, at least about 3%, at least about 2% or at least about 1% definitive endoderm cells. In preferred embodiments, isolated cell populations can comprise human definitive endoderm cells. In some embodiments, the percentage of definitive endoderm cells in the cell cultures or populations is calculated without regard to the feeder cells remaining in the culture.

Still other embodiments of the present invention relate to compositions, such as isolated cell populations or cell cultures, comprising mixtures of definitive endoderm cells and pluripotent stem cells. For example, cell cultures or cell populations comprising at least about 5 definitive endoderm cells for about every 95 pluripotent stem cell can be produced. In other embodiments, cell cultures or cell populations comprising at least about 95 definitive endoderm cells for about every 5 pluripotent stem cell can be produced. Additionally, cell cultures or cell populations comprising other ratios of definitive endoderm cells to pluripotent stem cells are contemplated. For example, compositions comprising at least about 1 definitive endoderm cell for about every 1,000,000, or at least 100,000 cells, or a least 10,000 cells, or at least 1000 cells or 500, or at least 250 or at least 100 or at least 10 pluripotent stem cell can be produced.

Further embodiments of the present invention relate to compositions, such as cell cultures or cell populations, comprising human cells, including human definitive endoderm cells which express Sox17 and at least two or at least 3 or more characteristics of a cell of a definitive endoderm cell, such as FoxA2 (HNF3β) or do not express Gata4, Sparc, Apf or Dab.

In preferred embodiments of the present invention, cell cultures and/or cell populations of definitive endoderm cells comprise human definitive endoderm cells, that are non-recombinant cells. In such embodiments, the cell cultures and/or cell populations are devoid of or substantially free of recombinant human definitive endoderm cells.

Use of the Definitive Endoderm Cells

Another aspect relates to the use of the definitive endoderm cells produced by the methods as disclosed herein for subsequent differentiating into a Pdx1-positive progenitor cell.

In some embodiments, an endoderm cell, e.g., a definitive endoderm cell produced by a method described herein, is differentiated to a cell of a second cell type (e.g., a differentiated cell). Included herein are cells and compositions made by the methods described herein. Exemplary second cell types include those cells which are derived from endoderm such as liver, lung, stomach, intestine, and thymus as well as the pancreas. For example, in some embodiments, definitive endoderm cells may be differentiated into liver endoderm cells by contacting the definitive endoderm cell with about 10 ng/ml-100 ng/ml (preferably, about 50 ng/ml) of FGF10.

In some embodiments, an endoderm cell, e.g., a definitive endoderm cell produced by a method described herein, is differentiated into a pancreatic cell, such as, for example, pancreatic endocrine cells (alpha cells, β-cells, delta cells, Pdx1-positive pancreatic progenitors (also referred to herein as "PP" cells) and the like) or a pancreatic exocrine cell.

In certain embodiments, the definitive endoderm cells produced by the methods as disclosed herein are produced from the human or mouse pluripotent stem cells, e.g. embryonic stem cells. Pancreatic cell precursors, e.g. Pdx1-positive progenitors can be differentiated further, either in a single step or in multiple steps, to a insulin-producing cells.

In accordance with certain examples, step-wise differentiation may be implemented to differentiate stem cells to a desired cell, such as a pancreatic cell. One method of step-wise differentiation is described in U.S. Pat. No. 7,326,572, which is incorporated herein in its entirety by reference. In brief, a pluripotent stem cell population is differentiated into a definitive endoderm cell using the methods as disclosed herein, and then further differentiated into a pdx1-positive pancreatic progenitor using the methods as disclosed herein, which can optionally be further differentiated into more mature cells that are more and more specialized towards the formation of certain types of pancreatic cells, such as towards insulin producing cells such as pancreatic β-cells. Using this step-wise differentiation, pluripotent stem cells, e.g. hESC or iPS cells can be differentiated toward a mature pancreatic cell type in several deliberate stages.

In certain embodiments, an immature endoderm cells, e.g. definitive endoderm cells may first be produced from undifferentiated stem cells. For examples, early in ontogeny, endoderm cells are capable of making epithelial cells of the GI tract and respiratory system, and the key digestive organs (liver and pancreas). Pancreatic cells can be generated, for example, using a two-stage approach. Stage 1 generally involves obtaining a population of common endoderm precursor cells. Stage 2 generally involves maturing the endoderm precursors into the pancreatic cells such as, for example, beta cells. In certain embodiments disclosed herein, the common endoderm precursor cells may be differentiated to provide pancreatic cell precursors such as, for example, Pdx1$^+$ pancreatic cell precursors.

Stem cells can also be differentiated along the endoderm differentiation pathway by culturing with the suitable agents such as, for examples, the hepatocyte differentiation agent n-butyrate. A further description of the hepatocyte differentiation paradigm may be found in International Patent Publication WO 01/81549 (Geron Corporation) which is incorporated herein by reference. Sonic Hedgehog is thought to be involved in liver specification, so including cyclopamine (an inhibitor of Sonic Hedgehog) in the culture medium is thought to help divert the cells toward the pancreatic lineage.

In some examples, differentiation of pdx1-positive progenitors may further be directed in a subsequent step, using, for example, the terminal differentiation factor nicotinamide (in the presence of cyclopamine and activin A). In other examples, one or more additional stages of differentiation may be implemented. For example, it may be desirable to further differentiate or mature of the pancreatic cells into a desired cell type.

In certain embodiments disclosed herein, the stem cells may be cultured or exposed to one or more compounds described herein during any one or more stages of the step-wise differentiation. For example, it may be desirable to expose undifferentiated hESCs to at least one compound described herein during the first stage of the step-wise differentiation, the second stage of step-wise differentiation and/or any additional stages of step-wise differentiation. In other examples, it may be desirable to expose the stem cells to at least one compound described herein only after the first stage of step-wise differentiation.

In certain examples, the desired number of stages for producing pancreatic cell types may be based, at least in part, on the intended use of the end-stage cell populations. For example, it may be desirable to produce beta cell precursors for therapy for treating metabolic disorders. In other examples, it may be desirable to further differentiate the pdx1-positive pancreatic progenitors into insulin-producing cells or pancreatic β-cells or pancreatic β-like cells for use in treating diabetes.

Another embodiments relate to the use of a definitive endoderm cells for transplanting into a subject in need thereof, where the definitive endoderm cell differentiates in vivo into a insulin-producing cell such as a pancreatic β-cell or pancreatic β-like cell.

Another aspect relates to the use of the Pdx1-positive pancreatic progenitor cells produced by the methods as disclosed herein for subsequent differentiating into insulin-producing cells, such as pancreatic β-cells or pancreatic β-like cells.

Another embodiments relate to the use of a Pdx1-positive pancreatic progenitor cells for transplanting into a subject in need thereof, where a Pdx1-positive pancreatic progenitor cell can spontaneously differentiate in vivo into a insulin-producing cell such as a pancreatic β-cell or pancreatic β-like cells.

Compounds for Inducing the Differentiation of Definitive Endoderm Cells into a Pdx1-Positive Progenitor One aspect of the present invention provides methods of producing a Pdx1-positive pancreatic progenitor cell, by contacting (e.g., culturing) an endoderm cell, e.g. a definitive endoderm cell with a compound of Formula (II) as described herein. Accordingly, in some embodiments any compound with Formula (II) useful in the methods and compositions as disclosed herein are cell permeable small molecules, and can control cellular processes by modulating signal transduction pathways, gene expression or metabolism and have been effectively used in stem cell differentiation protocols. As discussed previously, small molecules of Formula (I) or Formula (II) can be synthesized in high quantity and purity as well as conveniently supplied or removed, giving them great potential to be useful for therapeutic applications. High throughput screens have been performed to identify novel small molecules that can support the self renewal of ES cells (Chen et al., 2006; Desbordes et al., 2008), cardiogenic specification of mouse ES cells (Wu et al., 2004) or neural progenitor cells (Diamandis et al., 2007) as well as inducing specific cell types, notably neuronal and muscle cells (reviewed by (Ding and Schultz, 2004).

In one embodiment, an endoderm cell, e.g. a definitive endoderm cell, such as a human endoderm cell, or a human cell of endoderm origin is contacted with at least one compound of Formula (II) to differentiate the endoderm cell, e.g. a definitive endoderm cell into a Pdx1-positive progenitor cell.

In some embodiments, the method further comprises contacting a population of definitive endoderm cells with at least one compound of Formula (II) to induce differentiation of at least one definitive endoderm cell into a Pdx1-positive pancreatic progenitor cell, wherein the compound of Formula (II) is:

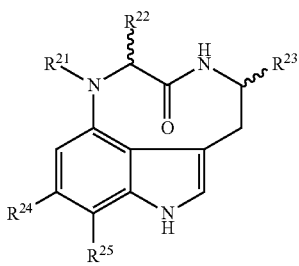

Formula (II)

$R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkyl, aryl, heteroaryl, cyclyl, or cyclyl, each of which can be optionally substituted, or $R^{24}$ and $R^{25}$ together with the carbons to which they arre attached form an optionally substituted cyclyl.

In some embodiments, the compound of formula (II) has the structure shown in formula (III):

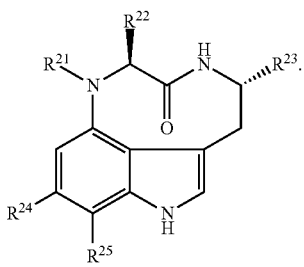

Formula (III)

In some other embodiments, the compound of formula (II) has the structure shown in formula (IV):

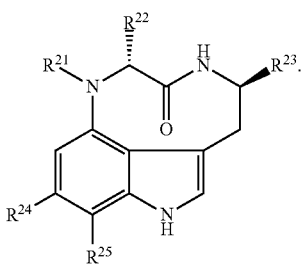

Formula (IV)

In some embodiments, $R^{21}$ is $C_1$-$C_6$ alkyl. Preferably $R^{21}$ is methyl or ethyl. Most preferably $R^{21}$ is methyl.

In some embodiments, $R^{22}$ is $C_1$-$C_6$ alkyl. Preferably $R^{22}$ is methyl, ethyl, propyl, or isopropyl. Most preferably, $R^{22}$ is isopropyl.

In some embodiments, $R^{23}$ is a substituted $C_1$-$C_6$ alkyl. Preferably $R^{22}$ is substituted with a hydroxyl group. In one preferred embodiment, $R^{23}$ is hydroxymethyl.

In some embodiments, $R^{24}$ is hydrogen, halogen, or optionally substituted linear or branched alkyl. Preferably $R^{24}$ is hydrogen.

In some embodiments, $R^{25}$ is an optionally substituted linear or branched alkyl, alkenyl or alkynyl. Generally, $R^{25}$ comprises one or more isoprenoid structure. Preferably $R^{25}$ comprises 6, 7, 8, 9, 10, 11, 12, 13, 14, 15, 16, 17, 18, 19, or 20 carbon atoms.

Preferred compounds of formula (II) include, but are not limited to, (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V), (2R,5R)-1,2,4,5,6,8-Hexahydro-5-(hydroxymethyl)-1-methyl-2-(1-methylethyl)-3H-pyrrolo[4,3,2-gh]-1,4-benzodiazonin-3-one ((+)-indolactam V), (−)-7-octylindolactam V, (+)-7-octylindolactam V, and teleocidins (e.g., teleocidin A1, teleocidin A2, telecidin B1, teleocidin B2, teleocidin B3, teleocidin B4 (Olivoretin D), and dihydrotelecidin B3).

In some embodiments of this aspect of the present invention provides methods of producing a Pdx1-positive pancreatic progenitor cell, by contacting (e.g., culturing) an endoderm cell, e.g. a definitive endoderm cell with a compound of Formula (II) as described herein, wherein the a cell of definitive endoderm is contacted with a compound of Formula (II) of about between 20 nM to 5 µM, or between about 20 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 4 µm, or about 2 µM to 5 µM.

In some embodiments of this aspect of the present invention provides methods of producing a Pdx1-positive pancreatic progenitor cell, by contacting (e.g., culturing) an endoderm cell, e.g. a definitive endoderm cell with a compound of Formula (II) as described herein, wherein the a cell of definitive endoderm is contacted with indolactam-V (ILV) at a concentration of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any interger between 200 nM-500 nM. In some embodiments, a definitive endoderm cell is contacted with indolatcam V at a concentration of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM. In some embodiments, a definitive endoderm cell is contacted with indolatcam V at a concentration of about 300 nM to differentiate the definitive endoderm cell into a Pdx1-positive pancreatic precursor cell.

Pdx1-Positive Pancreatic Progenitor Produced from Endoderm Cells

One can use any means common to one of ordinary skill in the art to confirm the presence of a Pdx1-positive pancreatic progenitor cell, e.g. a Pdx1-positive pancreatic progenitor cell produced the induction of the differentiation of a definitive endoderm cell by exposure to a compound of Formula (II), e.g. as indolatam V (ILV). In some embodiments, the presence of endoderm cells can be detected using suitable markers such as those listed in International Patent No. WO/2009/132083, which is incorporated herein in its entirety by reference.

In some embodiments, the presence of Pdx1-positive pancreatic progenitor markers, e.g. chemically induced Pdx1-positive pancreatic progenitor cells can be done by detecting the presence or absence of one or more markers indicative of an Pdx1-positive pancreatic progenitor. In some embodiments, the method can include detecting the positive expression (e.g. the presence) of a marker for Pdx1-positive pancreatic progenitor cells. In some embodiments, the marker can be detected using a reagent, e.g., a reagent for the detection of Pdx1. In particular, Pdx1-positive pancreatic progenitors herein express Pdx1 and HNF6. Other positive markers for Pdx1-positive pancreatic progenitor cells also include, for example as shown FIG. 4C of WO2009/132083, which include Pdx1, HNF6, PFT1A, Sox9, FoxA2, Ngn3, Nkx2.2 and Nkx6.1. Negative markers (e.g. the absence of significant levels of expression) for Pdx1-positive pancreatic progenitor cells include Sox7, Cdx2, Ces2, Fabp2, AFP, Albumlin, Barx1, Troponin and Sox2. Further, similar to definitive endoderm cells, Pdx1-positive pancreatic progenitor do not express extra-embryonic (EE) endoderm markers such as Gata4, SPARC, APF and DAB, or negative markers Zic, Pax6, Flk1 or CD31. Also encompassed is the negative expression of definitive endoderm markers, such as Sox17 and FoxA2 (HNF3β). Negative markers of Pdx1-positive pancreatic progenitor cells are useful for the purposes of negative selection of non-Pdx1-positive pancreatic progenitor cells (e.g. selection and discarding cells which express Gata4, SPARC, APF, DAB, Zic, Pax6, Flk1 or CD31) or for identification of cells which do not express these negative markers (e.g. Pdx1-positive pancreatic progenitor cells). A reagent for a marker can be, for example, an antibody against the marker or primers for a RT-PCR or PCR reaction, e.g., a semi-quantitative or quantitative RT-PCR or PCR reaction. Such markers can be used to evaluate whether a definitive endoderm cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of the differentiation of a definitive endoderm to a Pdx1-positive pancreatic progenitor can be monitored by determining the expression of markers characteristic of Pdx1-positive pancreatic progenitor cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of Pdx1-positive pancreatic progenitor cells as well as the lack of significant expression of markers characteristic of the definitive endoderm cells from which it was derived is determined.

As described in connection with monitoring the production of a Pdx1-positive pancreatic progenitor from a definitive endoderm cell, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. Additionally, it will be appreciated that at the polypeptide level, many of the markers of pancreatic islet hormone-expressing cells are secreted proteins. As such, techniques for measuring extracellular marker content, such as ELISA, may be utilized.

In other embodiments, the expression of Pdx1 or Cdcp1, or Ptf1a, or HNF6 or Nkx2.2 in a Pdx1-positive pancreatic progenitor cell is at least about 4-fold higher, at least about 6-fold higher, at least about 8-fold higher, at least about 10-fold higher, at least about 15-fold higher, at least about 20-fold higher, at least about 30-fold higher, at least about 40-fold higher, at least about 50-fold higher, at least about 60-fold higher, at least about 70-fold higher, at least about 80-fold higher, at least about 90-fold higher, at least about 100-fold higher or more than 100-fold higher than the expression of Pdx1 or Cdcp1, or Ptf1a, or HNF6 or Nkx2.2 in a definitive endoderm cell or pluripotent stem cell from which the Pdx1-positive pancreatic progenitor cell was derived.

The chemically induced reprogrammed cells as disclosed herein can express any number of Pdx1-positive pancreatic progenitor, including: Pdx1 or Cdcp1, or Ptf1a, or HNF6 or Nkx2.2 or Fox2A and other general markers for Pdx1-positive pancreatic progenitor cells, etc. Other markers can include the absence of expression of extra-embryonic endoderm cell markers, such as but not limited to Gata4, Sparc, AFP and Dab. Other markers include the absence or expression of Zic, Pax6, Flk1 or CD31. Definitive endoderm cells can also be characterized by the down-regulation of markers characteristic of non-pancreatic lineages, such as Sox7, Cdx2, Ces2, Fabp2, AFP, Albumlin, Barx1, Troponin and Sox2.

It is understood that the present invention is not limited to those markers listed as Pdx1-positive pancreatic progenitor markers herein, and the present invention also encompasses markers such as cell surface markers, antigens, and other gene products including ESTs, RNA (including microRNAs and antisense RNA), DNA (including genes and cDNAs), and portions thereof.

In some embodiments, a population of Pdx1-positive pancreatic progenitor can be replated or otherwise manipulated to begin another stage of differentiation. In certain circumstances, differentiation or maintenance of cells may be enhanced if the cells are kept in micromass clusters (for example, 50 to 5,000 cells), so that alpha, beta, and delta cells can interact directly.

Enrichment and Isolation and Purification of a Pdx1-Positive Pancreatic Progenitor Cell Another aspect of the present invention relates to the isolation of a population of Pdx1-positive pancreatic progenitor cells from a heterogeneous population of cells, such a mixed population of cells comprising Pdx1-positive pancreatic progenitor cells and definitive endoderm cells from which the Pdx1-positive pancreatic progenitor cells were derived. A population of Pdx1-positive pancreatic progenitor produced by any of the above-described processes can be enriched, isolated and/or purified by using any cell surface marker present on the Pdx1-positive pancreatic progenitor which is not present on the definitive endoderm cell from which it was derived. Such cell surface markers are also referred to as an affinity tag which is specific for a Pdx1-positive pancreatic progenitor cell. Examples of affinity tags specific for Pdx1-positive pancreatic progenitor cells are antibodies, ligands or other binding agents that are specific to a marker molecule, such as a polypeptide, that is present on the cell surface of a Pdx1-positive pancreatic progenitor cell but which is not substantially present on other cell types (e.g. on definitive endoderm cells). In some processes, an antibody which binds to a cell surface antigen on a Pdx1-positive pancreatic progenitor (e.g. a human Pdx1-positive pancreatic progenitor cell) is used as an affinity tag for the enrichment, isolation or purification of chemically induced (e.g. by contacting with a compound Formula II, e.g. indolactam V (ILV)) Pdx1-positive pancreatic progenitor cells produced by the methods described herein. Such antibodies are known and commercially available.

The skilled artisan will readily appreciate that the processes for using antibodies for the enrichment, isolation and/or purification of Pdx1-positive pancreatic progenitor cells. For example, in some embodiments, the reagent, such as an antibody, is incubated with a cell population comprising Pdx1-positive pancreatic progenitor cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FITC-conjugated antibody that is capable of binding to the primary antibody. The Pdx1-positive pancreatic progenitor cells are then washed, centrifuged and resuspended in buffer. The Pdx1-positive pancreatic progenitor suspension is then analyzed and sorted using a fluorescence activated cell sorter (FACS). Antibody-bound, fluorescent reprogrammed cells are collected separately from non-bound, non-fluorescent cells (e.g. non-Pdx1-positive pancreatic progenitors), thereby resulting in the isolation of Pdx1-positive pancreatic progenitors from other cells present in the cell suspension, e.g. definitive endoderm cells, pluripotent stem cells or non-Pdx1-positive pancreatic progenitors (e.g. other differentiated cell types).

In another embodiments of the processes described herein, the isolated cell composition comprising Pdx1-positive pancreatic progenitor cells can be further purified by using an alternate affinity-based method or by additional rounds of sorting using the same or different markers that are specific for Pdx1-positive pancreatic progenitors. For example, in some embodiments, FACS sorting is used to first isolate a Pdx1-positive pancreatic progenitor which expresses Pdx1, either alone or with the expression of HNF6, or alternatively with a marker selected from the group of Cdcp1, Ptf1a, Fox2A, Pdx1, Sox9, FoxA2, Ngn3, Nkx2.2 and Nkx6.1 from cells that do not express one of those markers (e.g. negative cells) in the cell population. A second FAC sorting, e.g. sorting the positive cells again using FACS to isolate cells that are positive for a different marker than the first sort (e.g. selecting for cells which are positive for at least one of: Cdcp1, Ptf1a, Fox2A, Pdx1, Sox9, FoxA2, Ngn3, Nkx2.2 and Nkx6. where the selected marker is different to the first sort) enriches the cell population for reprogrammed cells.

In an alternative embodiment, FACS sorting is used to separate cells by negatively sorting for a marker that is present on most definitive endoderm cells but is not present on Pdx1-positive pancreatic progenitor cells. For example, one can negatively select for cells which express at least one of Gata4, SPARC, APF or DAB, or Zic, Pax6, Flk1 or CD31 and discard these cells which express Sox17, Afp and collect the cells which have negative expression of at least one of Sox17, Afp or other negative Pdx1-positive pancreatic progenitor cells.

In some embodiments of the processes described herein, Pdx1-positive pancreatic progenitor cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above. For example, in some embodiments, at least one copy of a nucleic acid encoding GFP or a biologically active fragment thereof is introduced into a pluripotent stem cell which is first chemically induced into a definitive endoderm cell and then into a Pdx1-positive pancreatic progenitor, where a downstream of a promoter expressed in a Pdx1-positive pancreatic progenitor cell, such as the Pdx1 promoter, such that the expression of the GFP gene product or biologically active fragment thereof is under control of the Pdx1 promoter.

In addition to the procedures just described, chemically induced Pdx1-positive pancreatic progenitor cells may also be isolated by other techniques for cell isolation. Additionally, Pdx1-positive pancreatic progenitor cells may also be enriched or isolated by methods of serial subculture in growth conditions which promote the selective survival or selective expansion of the Pdx1-positive pancreatic progenitor cells. Such methods are known by persons of ordinary skill in the art.

Using the methods described herein, enriched, isolated and/or purified populations of Pdx1-positive pancreatic progenitor can be produced in vitro from definitive endoderm cells (which were differentiated from pluripotent stem cells by the methods described herein). In some embodiments, preferred enrichment, isolation and/or purification methods relate to the in vitro production of human Pdx1-positive pancreatic progenitor from human definitive endoderm cells, which were differentiated from human pluripotent stem cells, or from human induced pluripotent stem (iPS) cells. In such an embodiment, where Pdx1-positive pancreatic progenitor are differentiated from definitive endoderm cells which were previously derived from iPS cells, the Pdx1-positive pancreatic progenitor cell can be autologous to the subject from whom the cells were obtained to generate the iPS cells.

Using the methods described herein, isolated cell populations of Pdx1-positive pancreatic progenitor cells are enriched in Pdx1-positive pancreatic progenitor content by at least about 2- to about 1000-fold as compared to a population of cells before the chemical induction of the definitive endoderm cell population. In some embodiments, Pdx1-positive pancreatic progenitor cells can be enriched by at least about 5- to about 500-fold as compared to a population before the chemical induction of a definitive endoderm cell population. In other embodiments, Pdx1-positive pancreatic progenitors can be enriched from at least about 10- to about 200-fold as compared to a population before the chemical induction of a definitive endoderm cell population. In still other embodiments, Pdx1-positive pancreatic progenitors can be enriched from at least about 20- to about 100-fold as compared to a population before the chemical induction of a definitive endoderm cell population. In yet other embodiments, Pdx1-positive pancreatic progenitors can be enriched from at least about 40- to about 80-fold as compared to a population before the chemical induction of a definitive endoderm stem cell population. In certain embodiments, Pdx1-positive pancreatic progenitors can be enriched from at least about 2- to about 20-fold as compared to a population before the chemical induction of a definitive endoderm stem cell population.

Compositions Comprising Pdx1-Positive Pancreatic Progenitor Cells

Some embodiments of the present invention relate to cell compositions, such as cell cultures or cell populations, comprising Pdx1-positive pancreatic progenitor cells, wherein the Pdx1-positive pancreatic progenitor cells have been derived from definitive endoderm cells e.g. human definitive endoderm stem cells. In accordance with certain embodiments, the chemically induced Pdx1-positive pancreatic progenitors are mammalian cells, and in a preferred embodiment, such Pdx1-positive pancreatic progenitors are human d Pdx1-positive pancreatic progenitors.

Other embodiments of the present invention relate to compositions, such as an isolated cell population or cell culture, comprising Pdx1-positive pancreatic progenitor cells produced by the methods as disclosed herein. In some embodiments of the present invention relate to compositions, such as isolated cell populations or cell cultures, comprising chemically-induced Pdx1-positive pancreatic progenitor cells produced by the methods as disclosed herein. In such embodiments, the Pdx1-positive pancreatic progenitor cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the Pdx1-positive pancreatic progenitor population. In some embodiments, the composition comprises a population of Pdx1-positive pancreatic progenitor cells which make up more than about 90% of the total cells in the cell population, for example about at least 95%, or at least 96%, or at least 97%, or at least 98% or at least 99%, or about at least 100% of the total cells in the cell population are Pdx1-positive pancreatic progenitors.

Certain other embodiments of the present invention relate to compositions, such as an isolated cell population or cell cultures, comprise a combination of Pdx1-positive pancreatic progenitors and definitive endoderm cells from which the Pdx1-positive pancreatic progenitor were derived. In some embodiments, the definitive endoderm cells from which the Pdx1-positive pancreatic progenitor are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present invention relate to compositions, such as isolated cell populations or cell cultures, produced by the processes described herein and which comprise chemically induced Pdx1-positive pancreatic progenitor as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% Pdx1-positive pancreatic progenitor cells.

In another embodiment, isolated cell populations or compositions of cells (or cell cultures) comprise human Pdx1-positive pancreatic progenitor cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about 11%, at least about 10%, at least about 9%, at least about 8%, at least about 7%, at least about 6%, at least about 5%, at least about 4%, at least about 3%, at least about 2% or at least about 1% Pdx1-positive pancreatic progenitor cells. In preferred embodiments, isolated cell populations can comprise human Pdx1-positive pancreatic progenitor cells. In some embodiments, the percentage of Pdx1-positive pancreatic progenitor cells in the cell cultures or populations is calculated without regard to the feeder cells remaining in the culture.

Still other embodiments of the present invention relate to compositions, such as isolated cell populations or cell cultures, comprising mixtures of Pdx1-positive pancreatic progenitor and definitive endoderm cells from which they were differentiated from. For example, cell cultures or cell populations comprising at least about 5 Pdx1-positive pancreatic progenitor cells for about every 95 definitive endoderm cell can be produced. In other embodiments, cell cultures or cell populations comprising at least about 95 Pdx1-positive pancreatic progenitor cells for about every 5 definitive endoderm cell can be produced. Additionally, cell cultures or cell populations comprising other ratios of Pdx1-positive pancreatic progenitor cells to definitive endoderm cells are contemplated. For example, compositions comprising at least about 1 Pdx1-positive pancreatic progenitors for about every 1,000,000, or at least 100,000 cells, or a least 10,000 cells, or at least 1000 cells or 500, or at least 250 or at least 100 or at least 10 definitive endoderm cell can be produced.

Further embodiments of the present invention relate to compositions, such as cell cultures or cell populations, comprising human cells, including human Pdx1-positive pancreatic progenitor which express Pdx1 and HNF6.

In preferred embodiments of the present invention, cell cultures and/or cell populations of Pdx1-positive pancreatic progenitor cells comprise human Pdx1-positive pancreatic progenitor cells, that are non-recombinant cells. In such embodiments, the cell cultures and/or cell populations are devoid of or substantially free of recombinant human Pdx1-positive pancreatic progenitor cells.

Admixture Compositions.

Another aspect of the present invention relates to an admixture of definitive endoderm cells and at least one compound of Formula (I), for example, compounds IDE1 and/or IDE2 for inducing the differentiation of pluripotent stem cells to become definitive endoderm cells.

In another aspect of the present invention relates to composition, such as a reaction admixture comprising a pluripotent stem cell, (e.g. a population of pluripotent stem cells for differentiating into definitive endoderm cells for) and at least one compound of Formula (I). Alternatively, the present invention relates to a reaction admixture comprising (i) a population of definitive endoderm cells produced by chemical induction of differentiation of a pluripotent stem cell to a definitive endoderm cell, and (ii) at least one compound of Formula (I), for example but not limited to IDE1 or IDE2.

In some embodiments, the concentrations of a compound of Formula (I) added to the reaction mixture is a sufficient dose for inducing a pluripotent stem cell to differentiate into a definitive endoderm cell, as described herein.

In some embodiments, the composition comprises a concentration of a compound of Formula (I) of about between 25 nM to 10 µM, or between about 25 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 5 µm, or about 5 µM to 10 µM.

In some embodiments, a composition or admixture comprises a concentration of a compound of Formula (I) of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM. In some embodiments, a composition or admixture comprises a concentration of a compound of Formula (I) of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM.

In some embodiments, a composition or admixture comprises a concentration of a compound of IDE1 of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-100 nM, or any integer between 50-150 nM, or any integer between 100 nM-200 nM or any integer between 200 nM-500 nM. In some embodiments, the composition or admixture comprises a concentration of IDE1 at about 100 nM.

In some embodiments, a composition or admixture comprises a concentration of a compound of IDE2 of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-200 nM, or any integer between 100-300 nM, or any integer between 100 nM-500 nM or any integer between about 200 nM-500 nM. In some embodiments, the composition or admixture comprises a concentration of IDE2 at about 200 nM.

Another aspect of the present invention relates to an admixture of pdx1-positive pancreatic progenitor cells and at least one compound of Formula (II), for example, compounds of indolatam-V (ILV) for inducing the differentiation of a definitive endoderm cells to become a pdx1-positive pancreatic progenitor cell.

In another aspect of the present invention relates to composition, such as a reaction admixture comprising a definitive endoderm cells (e.g. produced by differentiation of a pluripotent stem cell by the methods as disclosed herein) and at least one compound of Formula (II), such as but not limited to Indolatam-V (ILV).

In some embodiments, the concentrations of a compound of Formula (I) added to the reaction mixture is a sufficient dose for inducing a definitive endoderm cell to differentiate into a Pdx1 progenitor as described herein.

In some embodiments, the composition comprises a concentration of a compound of Formula (II) of about between 20 nM to 5 µM, or between about 20 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 4 µm, or about 2 µM to 5 µM.

In some embodiments, a composition or admixture comprises a concentration of a compound of Formula (II), wherein the compound of formula (II) is indolactam-V (ILV) of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM. In some embodiments, a composition or admixture comprises a concentration of ILV of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM. In some embodiments, the composition or admixture comprises a concentration of ILV at about 300 nM.

Compositions and Kits

Described herein are compositions which comprise a cell described herein (e.g., a definitive endoderm cell or a pdx1-positive progenitor cell). In some embodiments, the composition also includes a compound described herein (e.g., a small molecule such as a compound of formula (I), e.g., IDE1 and/or IDE2 or an HDAC inhibitor) and/or cell culture media. Described herein are also compositions comprising the compounds described herein (e.g. cell culture media comprising one or more of the compounds described herein).Described herein are kits.

Another aspect of the present invention relates to kits for practicing methods disclosed herein and for making definitive endoderm cells disclosed herein. In one aspect, a kit includes a pluripotent stem cell and a compound of Formula (I), e.g. but not limited to IDE1 and/or IDE2 as described herein, and optionally, the kit can further comprise instructions for converting a population of pluripotent stem cells to a population of definitive endoderm cell using a method described herein. In some embodiments, the kit can further comprise a compound of Formula (II), e.g., but not limited to Indolatam-V (ILV).

In one embodiment, the kit can comprise a pluripotent stem cell for the purposes of being used as a positive control, for example to assess or monitor the effectiveness or ability of a compound of formula (I) to chemically induce the pluripotent stem cell to differentiate into a definitive endoderm cell. Accordingly, the kit can comprise sufficient amount of a compound of Formula (I) for inducing the differentiation of a control pluripotent stem cell population (positive control) as well as inducing the differentiation of a population of pluripotent stem cells of interest (e.g. the users preferred pluripotent stem cell e.g. an iPS cell) into a population of definitive endoderm cell.

Similarly, the kit can comprise sufficient amount of a compound of Formula (II) for inducing the differentiation of a control definitive endoderm cell population (positive control) as well as inducing the differentiation of a population of definitive endoderm cells of interest (e.g. the users preferred definitive endoderm cells) into a population of pdx1-positive pancreatic progenitor cells.

Exemplary components of the kit include the compounds of Formula (I) are described herein, e.g., IDE1 and/or IDE2, and optionally, compound of Formula (II), e.g. Indolatam-V (ILV).

In some embodiment, the compound in the kit can be provided in a watertight or gas tight container which in some embodiments is substantially free of other components of the kit. The compound can be supplied in more than one container, e.g., it can be supplied in a container having sufficient reagent for a predetermined number of reactions e.g., 1, 2, 3 or greater number of separate reactions to induce pluripotent stem cells to definitive endoderm cells, and subsequently into pdx1-positive endoderm cells. A compound(s) described herein (e.g., compounds of Formula I or II, such as compounds of Formula (I), including IDE1 and IDE1) or compounds of Formula (II) e.g. Indolactam-V (ILV) can be provided in any form, e.g., liquid, dried or lyophilized form. It is preferred that a compound(s) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

In some embodiments, the kit further optionally comprises information material. The informational material can be descriptive, instructional, marketing or other material that relates to the methods described herein and/or the use of a compound(s) described herein for the methods described herein.

The informational material of the kits is not limited in its instruction or informative material. In one embodiment, the informational material can include information about production of the compound, molecular weight of the compound, concentration, date of expiration, batch or production site information, and so forth. In one embodiment, the informational material relates to methods for administering the compound. Additionally, the informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In one embodiment, the informational material can include instructions to administer a compound(s) (e.g., small molecules of Formulas (I) or (II) (e.g., a IDE1 or IDE2 for Formula (I) or ILV for Formula (II)) as described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or an additional agent, e.g., for inducing pluripotent stem cells (e.g., in vitro) or for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

A compound of Formula (I), e.g. IDE1 or IDE2, or Formula (II), e.g. ILV as described herein can be provided in any form, e.g., liquid, dried or lyophilized form. It is preferred that a compound(s) described herein be substantially pure and/or sterile. When a compound(s) d described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

The kit can include one or more containers for the composition containing at least one compound of Formula (I) and/or Formula (II) as described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The kit can also include a component for the detection of a marker for definitive endoderm cell, e.g., for a marker described herein, e.g., a reagent for the detection of positive definitive endoderm markers, e.g. Sox17 or Fox2A (HNF3β) or Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, and Rbm35. Or in some embodiments, the kit can also comprise reagents for the detection of negative markers of definitive endoderm cells, e.g. Gata4, SPARC, APF, DAB, Zic, Pax6, Flk1 or CD31 for the purposes of negative selection of non-definitive endoderm cells or for identification of cells which do not express these negative markers (e.g. definitive endoderm cells). The reagents can be, for example, an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

It may be desirable to perform an analysis of the karyotype of the definitive endoderm cell or pdx1-positive pancreatic progenitor cell. Accordingly, the kit can include a component for karyotyping, e.g., a probe, a dye, a substrate, an enzyme, an antibody or other useful reagents for preparing a karyotype from a cell.

The kit can include definitive endoderm cell, e.g., an definitive endoderm derived from the same type of pluripotent stem cell, for example for the use as a positive cell type control. The kit can include Pdx1-positive pancreatic progenitor, e.g., a Pdx1-positive pancreatic progenitor derived from a definitive endoderm produced by contacting a pluripotent stem cell with a compound of Formula (I), e.g. IDE1 or IDE1, for example for use as a positive cell type control.

The kit can also include informational materials, e.g., instructions, for use of two or more of the components included in the kit.

The informational material can be descriptive, instructional, marketing or other material that relates to the methods described herein and/or the use of a compound(s) described herein for differentiating a pluripotent stem cell according to the methods described herein. In one embodiment, the informational material can include information about production of the compound, molecular weight of the compound, concentration, date of expiration, batch or production site information, and so forth. In one embodiment, the informational material relates to methods for culturing a population of pluripotent stem cells in the presence of a compound of Formula (I), and optionally, informational material relating to methods for culturing a population of definitive endoderm cells in the presence of a compound of Formula (II).

Methods of Administering a Cell

In one embodiment, the cells described herein, e.g. a population of definitive endoderm cells and/or a population of Pdx1-positive pancreatic progenitor cells are transplantable, e.g., a population of definitive endoderm cells and/or a population of Pdx1-positive pancreatic progenitor cells can be administered to a subject. In some embodiment, the subject who is administered a population of definitive endoderm cells and/or a population of Pdx1-positive pancreatic progenitor cells is the same subject from whom a pluripotent stem cell used to differentiate into a definitive endoderm cell was obtained (e.g. for autologous cell therapy). In some embodiments, the subject is a different subject. In some embodiments, a subject suffering from diabetes such as type I diabetes, or is a normal subject. For example, the cells for transplantation (e.g. a composition comprising a population of definitive endoderm cells and/or a population of Pdx1-positive pancreatic progenitor cells) can be a form suitable for transplantation, e.g., organ transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A composition comprising a population of definitive endoderm cells and/or a population of Pdx1-positive pancreatic progenitor cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Pharmaceutical Compositions Comprising a Population of Definitive Endoderm Cells and/or a Population of Pdx1-Positive Pancreatic Progenitor Cells For administration to a subject, a cell populations produced by the methods as disclosed herein, e.g. a population of definitive endoderm cells (produced by contacting a population of pluripotent stem cell with a compound of Formula (I) (e.g. IDE1 and/or IDE2)), or a population of pdx1-positive progenitor cells (e.g. produced by contacting a population of definitive endoderm cells with a compound of Formula (II) (e.g. Indolactam-V (ILV))) can be administered to a subject, for example in a pharmaceutically acceptable compositions. These pharmaceutically acceptable compositions comprise a therapeutically-effective amount of a population of definitive endoderm cells or a population of Pdx1-positive pancreatic progenitor cells as described above, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein in respect to a population of cells means that amount of relevant cells in a population of cells, e.g., definitive endoderm cells and/or Pdx1-positive pancreatic progenitor cells, or composition comprising a definitive endoderm cells and/or Pdx1-positive pancreatic progenitor cells of the present invention which is effective for producing some desired therapeutic effect in at least a sub-population of cells in an animal at a reasonable benefit/risk ratio applicable to any medical treatment. For example, an amount of a population of definitive endoderm cells and/or Pdx1-positive pancreatic progenitor cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

As used herein, the phrase "subject in need of Pdx1-positive pancreatic progenitor cells" refers to a subject who is diagnosed with or identified as suffering from, having or at risk for developing diabetes (e.g., Type 1, Type 1.5 or Type 2), one or more complications related to diabetes, or a pre-diabetic condition.

A subject in need of Pdx1-positive pancreatic progenitor cells can be identified using any method used for diagnosis of diabetes. For example, Type 1 diabetes can be diagnosed using a glycosylated hemoglobin (A1C) test, a random blood glucose test and/or a fasting blood glucose test. Parameters for diagnosis of diabetes are known in the art and available to skilled artisan without much effort.

In some embodiments, the methods of the invention further comprise selecting a subject identified as being in need of additional Pdx1-positive pancreatic progenitor cells. A subject in need of Pdx1-positive pancreatic progenitor cells can be selected based on the symptoms presented, such as symptoms of type 1, type 1.5 or type 2 diabetes. Exemplary symptoms of diabetes include, but are not limited to, excessive thirst (polydipsia), frequent urination (polyuria), extreme hunger (polyphagia), extreme fatigue, weight loss, hyperglycemia, low levels of insulin, high blood sugar (e.g., sugar levels over 250 mg, over 300 mg), presence of ketones present in urine, fatigue, dry and/or itchy skin, blurred vision, slow healing cuts or sores, more infections than usual, numbness and tingling in feet, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, and combinations thereof.

In some embodiments, a composition comprising a population of definitive endoderm cells or pdx1-positive progenitors for administration to a subject can further comprise a pharmaceutically active agent, such as those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyclopyramide, and Glimepiride), meglitinides ("glinides") (e.g., Nateglinide, Repaglinide and Mitiglinide), glucagon-like peptide-1 (GLP-1) and analogs (e.g., Exendin-4, Exenatide, Liraglutide, Albiglutide), insulin and insulin analogs (e.g., Insulin lispro, Insulin aspart, Insluin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapgliflozin, Remogliflozin and Sergliflozin) and others (e.g. Benfluorex and Tolrestat).

In type 1 diabetes, β-cells are undesirably destroyed by continued autoimmune response. This autoimmune response may also destroy definitive endoderm cells or pdx1-positive pancreatic progenitor cells implanted into a subject. Thus, this autoimmune response can be attenuated by use of compounds that inhibit or block such an autoimmune response. In some embodiments, a composition comprising a population of definitive endoderm cells or pdx1-positive progenitors for administration to a subject can further comprise a pharmaceutically active agent which is a immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, bbut are not limited to, members of the group consisting of Lisofylline (LSF) and the LSF analogs and derivatives described in U.S. Pat. No. 6,774,130, contents of which are herein incorporated by reference in their entirety.

A composition comprising a definitive endoderm cell can be administrated to the subject in the same time, of different times as the administration of a composition comprising pdx1-positive pancreatic progenitors. When administrated at different times, the compositions comprising a population of definitive endoderm cells and/or pdx1-positive progenitors for administration to a subject can be administered within 5 minutes, 10 minutes, 20 minutes, 60 minutes, 2 hours, 3 hours, 4, hours, 8 hours, 12 hours, 24 hours of administration of the other. When a compositions comprising a population of definitive endoderm cells and a composition comprising a population of pdx1-positive progenitors are administered in different pharmaceutical compositions, routes of administration can be different. In some embodiments, a subject is administered a composition comprising definitive endoderm cells. In other embodiments, a subject is administered a composition comprising pdx1-positive pancreatic progenitors. In another embodiment, a subject is administered a compositions comprising a population of definitive endoderm cells mixed with a population of pdx1-positive progenitors. In another embodiment, a subject is administered a composition comprising a population of definitive endoderm cells and a composition comprising a population of pdxl-positive progenitors, where administration is substantially at the same time, or subsequent to each other.

Toxicity and therapeutic efficacy of administration of a compositions comprising a population of definitive endoderm cells and/or pdx1-positive progenitors can be determined by standard pharmaceutical procedures in cell cultures or experimental animals, e.g., for determining the LD50 (the dose lethal to 50% of the population) and the ED50 (the dose therapeutically effective in 50% of the population). Compositions comprising a population of definitive endoderm cells and/or pdx1-positive progenitors that exhibit large therapeutic indices, are preferred.

The amount of a composition comprising a population of definitive endoderm cells and/or pdx1-positive progenitors can be tested using several well-established animal models.

The non-obese diabetic (NOD) mouse carries a genetic defect that results in insulitis showing at several weeks of age (Yoshida et al., Rev. Immunogenet. 2:140, 2000). 60-90% of the females develop overt diabetes by 20-30 weeks. The immune-related pathology appears to be similar to that in human Type I diabetes. Other models of Type I diabetes are mice with transgene and knockout mutations (Wong et al., Immunol. Rev. 169:93, 1999). A rat model for spontaneous Type I diabetes was recently reported by Lenzen et al. (Diabetologia 44:1189, 2001). Hyperglycemia can also be induced in mice (>500 mg glucose/dL) by way of a single intraperitoneal injection of streptozotocin (Soria et al., Diabetes 49:157, 2000), or by sequential low doses of streptozotocin (Ito et al., Environ. Toxicol. Pharmacol. 9:71, 2001). To test the efficacy of implanted islet cells, the mice are monitored for return of glucose to normal levels (<200 mg/dL).

Larger animals provide a good model for following the sequelae of chronic hyperglycemia. Dogs can be rendered insulin-dependent by removing the pancreas (J. Endocrinol. 158:49, 2001), or by feeding galactose (Kador et al., Arch. Opthalmol. 113:352, 1995). There is also an inherited model for Type I diabetes in keeshond dogs (Am. J. Pathol. 105:194, 1981). Early work with a dog model (Banting et al., Can. Med. Assoc. J. 22:141, 1922) resulted in a couple of Canadians making a long ocean journey to Stockholm in February of 1925.

By way of illustration, a pilot study can be conducted by implanting a population of definitive endoderm cells or a population of pdx1-pancreatic progenitors (or both) into the following animals: a) non-diabetic nude (T-cell deficient) mice; b) nude mice rendered diabetic by streptozotocin treatment; and c) nude mice in the process of regenerating islets following partial pancreatectomy. The number of cells transplanted is equivalent to ~1000-2000 normal human β-cells implanted under the kidney capsule, in the liver, or in the pancreas. For non-diabetic mice, the endpoints of can be assessment of graft survival (histological examination) and determination of insulin production by biochemical analysis, RIA, ELISA, and immunohistochemistry. Streptozotocin treated and partially pancreatectomized animals can also be evaluated for survival, metabolic control (blood glucose) and weight gain.

In some embodiments, data obtained from the cell culture assays and in animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising a population of definitive endoderm cells and/or pdx1-positive progenitors can also be estimated initially from cell culture assays. A dose may be formulated in animal models in vivo to achieve a secretion of insulin at a concentration which is appropriate in response to circulating glucose in the plasma. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of the definitive endoderm cells or pdx1-positive pancreatic progenitor cells as disclosed herein. In one embodiment of the invention, an isolated population of definitive endoderm cells and/or pdx1-positive pancreatic progenitors as disclosed herein may be used for the production of a pharmaceutical composition, for the use in transplantation into subjects in need of treatment, e.g. a subject that has, or is at risk of developing diabetes, for example but not limited to subjects with congenital and acquired diabetes. In one embodiment, an isolated population of the definitive endoderm cells and/or pdx1-positive pancreatic progenitors may be genetically modified. In another aspect, the subject may have or be at risk of diabetes and/or metabolic disorder. In some embodiments, an isolated population of the definitive endoderm cells and/or pdx1-positive pancreatic progenitors as disclosed herein may be autologous and/or allogenic. In some embodiments, the subject is a mammal, and in other embodiments the mammal is a human.

The use of an isolated population of definitive endoderm cells and/or pdx1-positive pancreatic progenitors as disclosed herein provides advantages over existing methods because the definitive endoderm cells and/or pdx1-positive pancreatic progenitors can be differentiated from stem cells, e.g. iPS cells obtained or harvested from the subject administered an isolated population of definitive endoderm cells and/or pdx1-positive pancreatic progenitors. This is highly advantageous as it provides a renewable source of definitive endoderm cells and/or pdx1-positive pancreatic progenitors with can be differentiated in vitro or in vivo to insulin producing cells (e.g.

pancreatic β-like cells or cells with pancreatic β-cell characteristics) by methods commonly known by one of ordinary skill in the art, for transplantation into a subject, in particular a substantially pure population of definitive endoderm cells and/or pdx1-positive pancreatic progenitors that do not have the risks and limitations of cells derived from other systems.

In another embodiment, an isolated population of definitive endoderm cells and/or pdx1-positive pancreatic progenitors can be used as models for studying properties for the differentiation into insulin-producing cells, e.g. to pancreatic β-cells or pancreatic β-like cells, or pathways of development of cells of endoderm origin into pancreatic β-cells.

In some embodiments, the definitive endoderm cells and/or pdx1-positive pancreatic progenitors may be genetically engineered to comprise markers operatively linked to promoters that are expressed when a marker is expressed or secreted, for example, a marker can be operatively linked to an insulin promoter, so that the marker is expressed when the definitive endoderm cells and/or pdx1-positive pancreatic progenitors are differentiated into insulin-producing cells which express and secrete insulin. In some embodiments, a population of definitive endoderm cells and/or pdx1-positive pancreatic progenitors can be used as a model for studying the differentiation pathway of cells which differentiate into islet β-cells or pancreatic β-like cells.

In other embodiments, the definitive endoderm cells and/or pdx1-positive pancreatic progenitors can be used as models for studying the role of islet β-cells in the pancreas and in the development of diabetes and metabolic disorders. In some embodiments, the definitive endoderm cells and/or pdx1-positive pancreatic progenitors can be from a normal subject, or from a subject which carries a mutation and/or polymorphism (e.g. in the gene Pdx1 which leads to early-onset insulin-dependent diabetes mellitus (NIDDM), as well as maturity onset diabetes of the young type 4 (MODY4), which can be use to identify small molecules and other therapeutic agents that can be used to treat subjects with diabetes with a mutation or polymorphism in Pdx1. In some embodiments, the definitive endoderm cells and/or pdx1-positive pancreatic progenitors may be genetically engineered to correct the polymorphism in the Pdx1 gene prior to being administered to a subject in the therapeutic treatment of a subject with diabetes. In some embodiments, the definitive endoderm cells and/or pdx1-positive pancreatic progenitors may be genetically engineered to carry a mutation and/or polymorphism.

In one embodiment of the invention relates to a method of treating diabetes or a metabolic disorder in a subject comprising administering an effective amount of a composition comprising a population of definitive endoderm cells and/or pdx1-positive pancreatic progenitors as disclosed herein to a subject with diabetes and/or a metabolic disorder. In a further embodiment, the invention provides a method for treating diabetes, comprising administering a composition comprising a population of definitive endoderm cells and/or pdx1-positive pancreatic progenitors as disclosed herein to a subject that has, or has increased risk of developing diabetes in an effective amount sufficient to produce insulin in response to increased blood glucose levels.

In one embodiment of the above methods, the subject is a human and a population of definitive endoderm cells and/or pdx1-positive pancreatic progenitors as disclosed herein are human cells. In some embodiments, the invention contemplates that a population of definitive endoderm cells and/or pdx1-positive pancreatic progenitors as disclosed herein are administered directly to the pancreas of a subject, or is administered systemically. In some embodiments, a population of definitive endoderm cells and/or pdx1-positive pancreatic progenitors as disclosed herein can be administered to any suitable location in the subject, for example in a capsule in the blood vessel or the liver or any suitable site where administered population of definitive endoderm cells and/or pdx1-positive pancreatic progenitors can differentiate into insulin producing cells and can secrete insulin in response to increased glucose levels in the subject.

The present invention is also directed to a method of treating a subject with diabetes or a metabolic disorder which occurs as a consequence of genetic defect, physical injury, environmental insult or conditioning, bad health, obesity and other diabetes risk factors commonly known by a person of ordinary skill in the art. Efficacy of treatment of a subject administered a composition comprising a population of definitive endoderm cells and/or pdx1-positive pancreatic progenitors can be monitored by clinically accepted criteria and tests, which include for example, (i) Glycated hemoglobin (A1C) test, which indicates a subjects average blood sugar level for the past two to three months, by measuring the percentage of blood sugar attached to hemoglobin, the oxygen-carrying protein in red blood cells. The higher your blood sugar levels, the more hemoglobin has sugar attached. An A1C level of 6.5 percent or higher on two separate tests indicates the subject has diabetes. A test value of 6-6.5% suggest the subject has prediabetes. (ii) Random blood sugar test. A blood sample will be taken from the subject at a random time, and a random blood sugar level of 200 milligrams per deciliter (mg/dL)-11.1 millimoles per liter (mmol/L), or higher indicated the subject has diabetes. (iii) Fasting blood sugar test. A blood sample is taken from the subject after an overnight fast. A fasting blood sugar level between 70 and 99 mg/dL (3.9 and 5.5 mmol/L) is normal. If the subjects fasting blood sugar levels is 126 mg/dL (7 mmol/L) or higher on two separate tests, the subject has diabetes. A blood sugar level from 100 to 125 mg/dL (5.6 to 6.9 mmol/L) indicates the subject has prediabetes. (iv) Oral glucose tolerance test. A blood sample will be taken after the subject has fasted for at least eight hours or overnight and then ingested a sugary solution, and the blood sugar level will be measured two hours later. A blood sugar level less than 140 mg/dL (7.8 mmol/L) is normal. A blood sugar level from 140 to 199 mg/dL (7.8 to 11 mmol/L) is considered prediabetes. This is sometimes referred to as impaired glucose tolerance (IGT). A blood sugar level of 200 mg/dL (11.1 mmol/L) or higher may indicate diabetes.

In some embodiments, the effects of administration of a population of definitive endoderm cells and/or pdx1-positive pancreatic progenitors as disclosed herein to a subject in need thereof is associated with improved exercise tolerance or other quality of life measures, and decreased mortality. The effects of cellular therapy with definitive endoderm cells and/or pdx1-positive pancreatic progenitors can be evident over the course of days to weeks after the procedure. However, beneficial effects may be observed as early as several hours after the procedure, and may persist for several years.

In some embodiments, a population of definitive endoderm cells and/or pdx1-positive pancreatic progenitors as disclosed herein may be used for tissue reconstitution or regeneration in a human patient or other subject in need of such treatment. In some embodiments compositions of populations of definitive endoderm cells and/or pdx1-positive pancreatic progenitors can be administered in a manner that permits them to graft or migrate to the intended tissue site and reconstitute or regenerate the functionally deficient area. Special devices are available that are adapted for administering cells capable of reconstituting a population of β-cells in the pancreas or at an alternative desired location. Accordingly, the definitive endoderm cells and/or pdx1-positive pancreatic progenitors may be administered to a recipient subject's pancreas by injection, or administered by intramuscular injection.

In some embodiments, compositions comprising a population of definitive endoderm cells and/or pdx1-positive pancreatic progenitors as disclosed herein have a variety of uses in clinical therapy, research, development, and commercial purposes. For therapeutic purposes, for example, a population of definitive endoderm cells and/or pdx1-positive pancreatic progenitors as disclosed herein may be administered to enhance insulin production in response to increase in blood glucose level for any perceived need, such as an inborn error in metabolic function, the effect of a disease condition (e.g. diabetes), or the result of significant trauma (i.e. damage to the pancreas or loss or damage to islet β-cells). In some embodiments, a population of definitive endoderm cells and/or pdx1-positive pancreatic progenitors as disclosed herein are administered to the subject not only help restore function to damaged or otherwise unhealthy tissues, but also facilitate remodeling of the damaged tissues.

To determine the suitability of cell compositions for therapeutic administration, the definitive endoderm cells and/or pdx1-positive pancreatic progenitor cells can first be tested in a suitable animal model. At one level, cells are assessed for their ability to survive and maintain their phenotype in vivo. Cell compositions comprising definitive endoderm cells and/or pdx1-positive pancreatic progenitors can be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or beta-galactosidase); that have been prelabeled (for example, with BrdU or [3H] thymidine), or by subsequent detection of a constitutive cell marker (for example, using human-specific antibody). The presence and phenotype of the administered population of definitive endoderm cells and/or pdx1-positive pancreatic progenitors can be assessed by immunohistochemistry or ELISA using human-specific antibody, or by RT-PCR analysis using primers and hybridization conditions that cause amplification to be specific for human polynucleotides, according to published sequence data.

A number of animal models for testing diabetes are available for such testing, and are commonly known in the art, for example as disclosed in U.S. Pat. No. 6,187,991 which is incorporated herein by reference, as well as rodent models; NOD (non-obese mouse), BB_DB mice, KDP rat and TCR mice, and other animal models of diabetes as described in Rees et al, Diabet Med. 2005 April; 22(4):359-70; Srinivasan K, et al., Indian J Med. Res. 2007 March; 125(3):451-7; Chatzigeorgiou A, et al., In Vivo. 2009 March-April; 23(2): 245-58, which are incorporated herein by reference.

In some embodiments, a population of definitive endoderm cells and/or pdx1-positive pancreatic progenitors as disclosed herein may be administered in any physiologically acceptable excipient, where the definitive endoderm cells and/or pdx1-positive pancreatic progenitors may find an appropriate site for regeneration and differentiation. In some embodiments, a population of definitive endoderm cells and/or pdx1-positive pancreatic progenitors as disclosed herein can be introduced by injection, catheter, or the like. In some embodiments, a population of definitive endoderm cells and/or pdx1-positive pancreatic progenitors as disclosed herein can be frozen at liquid nitrogen temperatures and stored for long periods of time, being capable of use on thawing. If frozen, a population of definitive endoderm cells and/or pdx1-positive pancreatic progenitors will usually be stored in a 10% DMSO, 50% FCS, 40% RPMI 1640 medium. Once thawed, the cells may be expanded by use of growth factors and/or feeder cells associated with culturing 13 definitive endoderm cells and/or pdx1-positive pancreatic progenitors as disclosed herein.

In some embodiments, a population of definitive endoderm cells and/or pdx1-positive pancreatic progenitors as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of definitive endoderm cells and/or pdx1-positive pancreatic progenitors as disclosed herein will be adapted in accordance with the route and device used for administration. In some embodiments, a composition comprising a population of definitive endoderm cells and/or pdx1-positive pancreatic progenitors can also comprise or be accompanied with one or more other ingredients that facilitate the engraftment or functional mobilization of the definitive endoderm cells and/or pdx1-positive pancreatic progenitors. Suitable ingredients include matrix proteins that support or promote adhesion of the definitive endoderm cells and/or pdx1-positive pancreatic progenitors, or complementary cell types, especially endothelial cells. In another embodiment, the composition may comprise resorbable or biodegradable matrix scaffolds.

In some embodiments, a population of definitive endoderm cells and/or pdx1-positive pancreatic progenitors as disclosed herein may be genetically altered in order to introduce genes useful in differentiated progeny, e.g. genes useful in insulin producing cells such as pancreatic β-cells, e.g. repair of a genetic defect in an individual, selectable marker, etc., or genes useful in selection against non-insulin producing cells differentiated from a definitive endoderm cell and/or pdx1-positive pancreatic progenitor cell or for the selective suicide of implanted definitive endoderm cells and/or pdx1-positive pancreatic progenitors. In some embodiments, a population of definitive endoderm cells and/or pdx1-positive pancreatic progenitors can also be genetically modified to enhance survival, control proliferation, and the like. In some embodiments, a population of definitive endoderm cells and/or pdx1-positive pancreatic progenitors as disclosed herein can be genetically altering by transfection or transduction with a suitable vector, homologous recombination, or other appropriate technique, so that they express a gene of interest. In one embodiment, a definitive endoderm cell and/or pdx1-positive pancreatic progenitor is transfected with genes encoding a telomerase catalytic component (TERT), typically under a heterologous promoter that increases telomerase expression beyond what occurs under the endogenous promoter, (see International Patent Application WO 98/14592, which is incorporated herein by reference). In other embodiments, a selectable marker is introduced, to provide for greater purity of the population of definitive endoderm cells and/or pdx1-positive pancreatic progenitors. In some embodiments, a population of definitive endoderm cells and/or pdx1-positive pancreatic progenitors may be genetically altered using vector containing supernatants over a 8-16 h period, and then exchanged into growth medium for 1-2 days. Genetically altered definitive endoderm cells and/or pdx1-positive pancreatic progenitors can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, a population of definitive endoderm cells and/or pdx1-positive pancreatic progenitors as disclosed herein can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, such as somatostatin, glucagon, and other factors.

Many vectors useful for transferring exogenous genes into target definitive endoderm cells and/or pdx1-positive pancreatic progenitors as disclosed herein are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. In some embodiments, combinations of retroviruses and an appropriate packaging cell line may also find use, where the capsid proteins will be functional for infecting the definitive endoderm cells and/or pdx1-positive pancreatic progenitors as disclosed herein. Usually, definitive endoderm cells and/or pdx1-positive pancreatic progenitors and virus will be incubated for at least about 24 hours in the culture medium. In some embodiments, the definitive endoderm cells and/or pdx1-positive pancreatic progenitors are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, a population of definitive endoderm cells and/or pdx1-positive pancreatic progenitors as disclosed herein are suitable for administering systemically or to a target anatomical site. A population of definitive endoderm cells and/or pdx1-positive pancreatic progenitors can be grafted into or nearby a subject's pancreas, for example, or may be administered systemically, such as, but not limited to, intra-arterial or intravenous administration. In alternative embodiments, a population of definitive endoderm cells and/or pdx1-positive pancreatic progenitors of the present invention can be administered in various ways as would be appropriate to implant in the pancreatic or secretory system, including but not limited to parenteral, including intravenous and intraarterial administration, intrathecal administration, intraventricular administration, intraparenchymal, intracranial, intracisternal, intrastriatal, and intranigral administration. Optionally, a population of definitive endoderm cells and/or pdx1-positive pancreatic progenitors are administered in conjunction with an immunosuppressive agent.

In some embodiments, a population of definitive endoderm cells and/or pdx1-positive pancreatic progenitors can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of definitive endoderm cells and/or pdxl-positive pancreatic progenitors can be administered to a subject the following locations: clinic, clinical office, emergency department, hospital ward, intensive care unit, operating room, catheterization suites, and radiologic suites.

In other embodiments, a population of definitive endoderm cells and/or pdx1-positive pancreatic progenitors is stored for later implantation/infusion. A population of definitive endoderm cells and/or pdx1-positive pancreatic progenitors may be divided into more than one aliquot or unit such that part of a population of definitive endoderm cells and/or pdx1-positive pancreatic progenitors is retained for later application while part is applied immediately to the subject. Moderate to long-term storage of all or part of the cells in a cell bank is also within the scope of this invention, as disclosed in U.S. Patent Application Serial No. 20030054331 and Patent Application No. WO03024215, and is incorporated by reference in their entireties. At the end of processing, the concentrated cells may be loaded into a delivery device, such as a syringe, for placement into the recipient by any means known to one of ordinary skill in the art.

In some embodiments, a population of definitive endoderm cells and/or pdx1-positive pancreatic progenitors can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of definitive endoderm cells and/or pdx1-positive pancreatic progenitors may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of definitive endoderm cells and/or pdx1-positive pancreatic progenitors could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 2002/0182211, which is incorporated herein by reference. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

Pharmaceutical compositions comprising effective amounts of a population of definitive endoderm cells and/or pdx1-positive pancreatic progenitors are also contemplated by the present invention. These compositions comprise an effective number of definitive endoderm cells and/or pdx1-positive pancreatic progenitors, optionally, in combination with a pharmaceutically acceptable carrier, additive or excipient. In certain aspects of the present invention, a population of definitive endoderm cells and/or pdx1-positive pancreatic progenitors are administered to the subject in need of a transplant in sterile saline. In other aspects of the present invention, a population of definitive endoderm cells and/or pdx1-positive pancreatic progenitors are administered in Hanks Balanced Salt Solution (HBSS) or Isolyte S, pH 7.4. Other approaches may also be used, including the use of serum free cellular media. In one embodiment, a population of definitive endoderm cells and/or pdx1-positive pancreatic progenitors are administered in plasma or fetal bovine serum, and DMSO. Systemic administration of a population of definitive endoderm cells and/or pdx1-positive pancreatic progenitors cells to the subject may be preferred in certain indications, whereas direct administration at the site of or in proximity to the diseased and/or damaged tissue may be preferred in other indications.

In some embodiments, a population of definitive endoderm cells and/or pdx1-positive pancreatic progenitors can optionally be packaged in a suitable container with written instructions for a desired purpose, such as the reconstitution or thawing (if frozen) of a population of definitive endoderm cells and/or pdx1-positive pancreatic progenitors prior to administration to a subject.

In one embodiment, an isolated population of definitive endoderm cells and/or pdx1-positive pancreatic progenitors as disclosed herein are administered with a differentiation agent. In one embodiment, the definitive endoderm cells and/or pdx1-positive pancreatic progenitors are combined with the differentiation agent to administration into the subject. In another embodiment, the cells are administered separately to the subject from the differentiation agent. Optionally, if the cells are administered separately from the differentiation agent, there is a temporal separation in the administration of the cells and the differentiation agent. The temporal separation may range from about less than a minute in time, to about hours or days in time. The determination of the optimal timing and order of administration is readily and routinely determined by one of ordinary skill in the art.

Diagnosis of Diabetes

Type 1 diabetes is an autoimmune disease that results in destruction of insulin-producing beta cells of the pancreas. Lack of insulin causes an increase of fasting blood glucose (around 70-120 mg/dL in nondiabetic people) that begins to appear in the urine above the renal threshold (about 190-200 mg/dl in most people). The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level of 11.1 mmol/L or higher (200 mg/dL or higher).

Type 1 diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycosylated). An A1C level of 6.5 percent or higher on two separate tests is indicative of diabetes. A result between 6 and 6.5 percent is considered prediabetic, which indicates a high risk of developing diabetes.

The Random Blood Glucose Test comprises obtaining a blood sample at a random time point from a subject suspected of having diabetes. Blood glucose values can be expressed in milligrams per deciliter (mg/dL) or millimoles per liter (mmol/L). A random blood glucose level of 200 mg/dL (11.1 mmol/L) or higher indicates the subject likely has diabetes, especially when coupled with any of the signs and symptoms of diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of diabetes.

Type 1 diabetes can also be distinguished from type 2 diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 diabetes as it appears that the immune system is involved in Type 1 diabetes etiology.

In some embodiments, the present invention provides compositions for the use of populations of definitive endoderm cells or populations of pdx1-positive pancreatic progenitor cells produced by the methods as disclosed herein or their differentiated progeny to restore islet function in a subject in need of such therapy. Any condition relating to inadequate production of a pancreatic endocrine (insulin, glucagon, or somatostatin), or the inability to properly regulate secretion may be considered for treatment with cells (e.g. populations of definitive endoderm cells or populations of pdx1-positive pancreatic progenitor cells) prepared according to this invention, as appropriate. Of especial interest is the treatment of Type I (insulin-dependent) diabetes mellitus.

Subjects in need thereof can be selected for treatment based on confirmed long-term dependence on administration of exogenous insulin, and acceptable risk profile. The subject receives approximately 10,000 definitive endoderm cells or pdx1-positive pancreatic progenitor cells equivalents per kg body weight. If the cells are not autologouse, in order to overcome an allotype mismatch, the subject can be treated before surgery with an immunosuppressive agent such as FK506 and rapamycin (orally) and daclizumab (intravenously). A composition comprising a populations of definitive endoderm cells and/or population of pdx1-positive pancreatic progenitor cells can be infused through a catheter in the portal vein. The subject can then be subjected to abdominal ultrasound and blood tests to determine liver function. Daily insulin requirement is tracked, and the subject is given a second transplant if required. Follow-up monitoring includes frequent blood tests for drug levels, immune function, general health status, and whether the patient remains insulin independent.

General approaches to the management of the diabetic patient are provided in standard textbooks, such as the Textbook of Internal Medicine, 3rd Edition, by W. N. Kelley ed., Lippincott-Raven, 1997; and in specialized references such as Diabetes Mellitus: A Fundamental and Clinical Text 2nd Edition, by D. Leroith ed., Lippincott Williams & Wilkins 2000; Diabetes (Atlas of Clinical Endocrinology Vol. 2) by C. R. Kahn et al. eds., Blackwell Science 1999; and Medical Management of Type 1 Diabetes 3rd Edition, McGraw Hill 1998. Use of islet cells for the treatment of Type I diabetes is discussed at length in Cellular Inter-Relationships in the Pancreas: Implications for Islet Transplantation, by L. Rosenberg et al., Chapman & Hall 1999; and Fetal Islet Transplantation, by C. M. Peterson et al. eds., Kluwer 1995.

As always, the ultimate responsibility for subject selection, the mode of administration, and dosage of a population of definitive endoderm cells or a population of pdx1-positive pancreatic progenitor cells is the responsibility of the managing clinician. For purposes of commercial distribution, populations of definitive endoderm cells or populations of pdx1-positive pancreatic progenitor cells as disclosed herein are typically supplied in the form of a pharmaceutical composition, comprising an isotonic excipient prepared under sufficiently sterile conditions for human administration. This invention also includes sets of population of definitive endoderm cells or populations of pdx1-positive pancreatic progenitor cells that exist at any time during their manufacture, distribution, or use. The sets of populations of definitive endoderm cells or populations of pdx1-positive pancreatic progenitor cells comprise any combination of two or more cell populations described in this disclosure, exemplified but not limited to the differentiation of definitive endoderm cells to become pdx1-positive pancreatic progenitor cells, and their subsequent differentiation e.g. into insulin-producing cells such as pancreatic β-cells or pancreatic β-like cells as the term is defined herein. In some embodiments, the cell compositions comprising populations of definitive endoderm cells or populations of pdx1-positive pancreatic progenitor cells can be administered (e.g. implanted into a subject) in combination with other cell types e.g. other differentiated cell types, sometimes sharing the same genome. Each cell type in the set may be packaged together, or in separate containers in the same facility, or at different locations, under control of the same entity or different entities sharing a business relationship.

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996. The composition is optionally packaged in a suitable container with written instructions for a desired purpose, such as the treatment of diabetes.

In some embodiments, compositions comprising populations of definitive endoderm cells or populations of pdx1-positive pancreatic progenitor cells can also be used as the functional component in a mechanical device designed to produce one or more of the endocrine polypeptides of pancreatic islet cells. In its simplest form, the device contains a population of definitive endoderm cells or populations of pdx1-positive pancreatic progenitor cells behind a semipermeable membrane that prevents passage of the cell population, retaining them in the device, but permits passage of insulin, glucagon, or somatostatin secreted by the cell population. This includes populations of definitive endoderm cells or populations of pdx1-positive pancreatic progenitor cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers>3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated for use to comprise a population of definitive endoderm cells or a population of pdx1-positive pancreatic progenitor cells, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

Methods of Identifying Compounds that Increase the Production of Endoderm

Described herein is a method of identifying a compound that increases the production of endoderm. In certain examples, a high content and/or high throughput screening method is provided. The method includes exposing a stem cell (e.g., an ES cell) to at least one compound (e.g., a library compound or a compound described herein) and determining if the compound increases the production of endoderm, e.g., definitive endoderm from the stem cells. A cell can be identified as an endoderm (e.g., a definitive endoderm) using one or more of the markers described herein. In some examples, the stem cells may be differentiated prior to exposure to the library. In other examples, two or more compounds may be used, either individually or together, in the screening assay. In additional examples, the stem cells may be placed in a multi-well plate, and a library of compounds may be screened by placing the various members of the library in different wells of the multi-well plate. Such screening of libraries can rapidly identify compounds that are capable of endoderm, e.g., definitive endoderm, from the stem cells.

In one aspect, the invention features a method of producing an endodermal cell, e.g., a definitive endoderm cell, the method comprising exposing a stem cell, e.g., an embryonic stem (ES) cell to an effective amount of at least one compound described herein, e.g., a compound of formula (I) e.g., IDE1 and/or IDE2, or an HDAC inhibitor(s), to differentiate the stem cell into the endodermal cell, e.g., the definitive endodermal cell. In some embodiments, the stem cell is from a mammal. In some embodiments, the stem cell is from mouse or human. In some embodiments, the stem cell is an embryonic stem cell (e.g., a mammalian embryonic stem cell such as a mouse or human embryonic stem cell). In some embodiments, a plurality of stem cells are differentiated into a plurality of endodermal cells, e.g., definitive endodermal cells.

In some embodiments, the method further comprises isolating a population of the endodermal cells, e.g., definitive endodermal cells (e.g., wherein at least 5%, 10%, 15%, 20%, 25%, 30%, 35%, 50%, 75% or greater of the subject cell type). In some embodiments, the compound is an HDAC inhibitor. In some embodiments, the compound is a compound of formula (I)

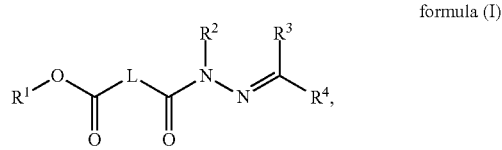

formula (I)

wherein
each $R^1$ and $R^2$ is independently H, alkyl, or arylalkyl;
each $R^3$ and $R^4$ is independently H or optionally substituted cycyl, heterocycyll, aryl, or heteroaryl; or $R^3$ and $R^4$ taken together with the carbon to which they are attached, form a ring; and
L is $C_{2-10}$ alkylenyl, $C_{2-10}$ heteroalkylenyl, $C_{2-10}$ alkenylenyl, or $C_{2-10}$ alkynylenyl.

In some embodiments, the compound is IDE1 or IDE2. In some embodiments, the stem cell is exposed to the compound, e.g., an HDAC inhibitor(s) or a compound of formula (I) e.g., IDE1 and/or IDE2, for about 1, 2, 4, 6, 8, 10, 12, 14, 16, or more days. In some embodiments, the stem cell is exposed to the compound, e.g., an HDAC inhibitor(s) or a compound of formula (I), e.g., IDE1 and/or IDE2, for 6 days. In some embodiments, the stem cell is exposed to the compound, e.g., an HDAC inhibitor(s) or a compound of formula (I), e.g., IDE1 and/or IDE2, at a concentration of about 25 nM, 50 nM, 100 nM, 150 nM, 200 nM, 250 nM, 400 nM, 500 nM, 600 nM, 700 nM, 800 nM, 1 µM, 21 µM, 3 µM, 4 µM, 5 µM or 10 µM. In some embodiments, the stem cell is exposed to the compound, e.g., an HDAC inhibitor(s) or a compound of formula (I), e.g., IDE1 and/or IDE2, at a concentration of about 250 nM, 400 nM, 500 nM, 600 nM, 700 nM, or 800 nM. In some embodiments, greater than about 20%, 30%, 40%, 50%, 60%, 70%, 80%, or 90% of the stems cells are differentiated into the endodermal cells, e.g., definitive endodermal cells.

In some embodiments, the method further comprises exposing the stem cells to at least one additional agent. In some embodiments, the additional agent is Nodal, Activin A or Wnt3a. In some embodiments, the endodermal cell, e.g., the definitive endodermal cell is a Sox17+ cell. In some embodiments, the expression of a marker selected from the group consisting of: Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Sox17, and Rbm35a is upregulated to by a statistically significant amount in the endodermal cell, e.g., the definitive endodermal cell relative to the stem cell. In some embodiments, the expression of a marker selected from the group consisting of: Gata4, SPARC, AFP and Dab2 is not upregulated to by a statistically significant amount in the endodermal cell, e.g., the definitive endodermal cell relative to the stem cell. In some embodiments, the expression of a marker selected from the group consisting of: Zic1, Pax6, Flk1 and CD31 is not upregulated to by a statistically significant amount in the endodermal cell, e.g., the definitive endodermal cell relative to the stem cell. In some embodiments, the phosphorylation of Smad2 is upregulated to by a statistically significant amount in the endodermal cell, e.g., the definitive endodermal cell relative to the stem cell. In some embodiments, at least one of the components in the TGFβ signaling pathway is activated by a statistically significant level in the endodermal cell, e.g., the definitive endodermal cell relative to the stem cell. In some embodiments, the endodermal cell, e.g., the definitive endodermal cell has the capacity to integrate into the developing gut tube in vivo. In some embodiments, the endodermal cell, e.g., the definitive endodermal cell can differentiate into a cell having the characteristic morphology of a gut cell and expressing markers of gut tube, e.g., FoxA2 and/or Claudin6, in vivo.

In some embodiments, the method further comprises differentiating the endodermal cell, e.g., the definitive endodermal cell into a cell of a second cell type. In some embodiments, the cell of the second cell type is a cell of gastrointestinal tract; a cell of respiratory tract; or a cell of endocrine gland, e.g., a liver cell, a pancreatic cell, or a pancreatic cell precursor. In some embodiments, the cell of the second cell type is a pancreatic cell or a pancreatic cell precursor, e.g. a Pdx1-positive pancreatic progenitor. In some embodiments, the pancreatic cell or pancreatic precursor cell, e.g. a Pdx1-positive pancreatic progenitor is a Pdx1+ cell or an HNF6+ cell. In some embodiments, the method further comprises exposing the endoderm cell, e.g., the definitive endoderm cell to FGF10 and a Hedgehog signaling inhibitor, e.g., KAAD-cyclopamine. In some embodiments, the method further comprises exposing the endoderm cell, e.g., the definitive endoderm cell to a posteriorizing factor, e.g., retinoic acid. In some embodiments, the method further comprises exposing the endoderm cell, e.g., the definitive endoderm cell to an effective amount of Indolactam V. In some embodiments, a plurality of endodermal cells, e.g., definitive endodermal cells, are differentiated into a plurality of cells of a second cell type, e.g. a cell of endoderm origin such as, but not limited to a pdx1-positive pancreatic progenitor. In some embodiments, the method further comprises isolating a population of the cells of the second cell type (e.g. a cell of endoderm origin, for example, a pdx1-positive pancreatic progenitors), wherein at least 5%, 10%, 15%, 20%, 25%, 30%, 35%, 50%, 75% or greater of the subject cell type (e.g. the second cell type or pdx1-positive pancreatic progenitors) are isolated.

In some embodiments, the method further comprises implanting the cells of definitive endoderm produced by the methods as disclosed herein, or implanting the second cell type e.g. a cell of endoderm origin, for example, a pdx1-positive pancreatic progenitors into a subject (e.g., a subject having diabetes, e.g., type I, type II or Type 1.5 diabetes). In some embodiments, the stem cell is from a subject. In some embodiments, the stem cell is from a donor different than the subject, e.g., a relative of the subject.

In one aspect, the invention features an endoderm cell, e.g. a definative endoderm cell made by a method described herein. In another aspect, the invention features a composition comprising an endoderm cell made by a method described herein. In yet another aspect, the invention features a second cell type (e.g. a pdx1-positive pancreatic progenitor) made by a method described herein. In one aspect, the invention features a composition comprising a second cell type (e.g. a pdx1-positive pancreatic progenitor) made by a method described herein.

In another aspect, the invention features a kit comprising: a stem cells, e.g., an ES cell; at least one compound described herein, e.g., an HDAC inhibitor(s) or a compound of formula (I), e.g., IDE1 and/or IDE2; and instructions for using the stem cells and the at least one compound to produce an endodermal cell, e.g., a definitive endoderm cell. In some embodiments, the kit further comprises: a component for the detection of a marker for an endodermal cell, e.g., for a marker described herein, e.g., a reagent for the detection of Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Sox17, and Rbm35a, e.g., an antibody against the marker; and an endodermal cell, e.g., a definitive endodermal cell, e.g., for use as a control. In some embodiments, the kit further comprises: a component to differentiate an endodermal cell, e.g., a definitive endodermal cell to a cell of a second cell type, e.g., a pancreatic cell or pancreatic cell precursors; and instructions for using the endodermal cell (e.g., the definitive endodermal cell) described herein and the component to produce the cell of a second type, e.g., pancreatic cell or pancreatic cell precursors. In some embodiments, the kit further comprises: a component for the detection of a marker for the cell of the second cell type, e.g., for a marker described herein, e.g., a reagent for the detection of Pdx1, e.g., an antibody against the marker; and a cell or the second cell type, e.g., a pancreatic cell or a pancreatic cell precursor, e.g., for use as a control.

In one aspect, the invention features a method of facilitating differentiation of a stem cell, e.g., an ES cell, to an endodermal cell, e.g., definitive endoderm comprising providing a stem cell, and providing at least one compound described herein, e.g., an HDAC inhibitor(s) or a compound of formula (I), e.g., IDE1 and/or IDE2, to differentiate the stem cell to provide the endodermal cell, e.g., definitive endodermal cell, upon exposure of the stem cell to the at least one compound. In some embodiments, the stem cell is from a mammal. In some embodiments, the stem cell is from mouse or human. In some embodiments, the stem cell is an embryonic stem cell (e.g., a mammalian embryonic stem cell such as a mouse or human embryonic stem cell).

In some embodiments, a plurality of stem cells are differentiated into a plurality of endoderm cells, e.g., definitive endodermal cells. In some embodiments, the compound is IDE1 or IDE2. In some embodiments, the stem cell is exposed to the compound, e.g., an HDAC inhibitor(s) or a compound of formula (I) e.g., IDE1 and/or IDE2, for about 1, 2, 4, 6, 8, 10, 12, 14, 16, or more days. In some embodiments, the stem cell is exposed to the compound, e.g., an HDAC inhibitor(s) or a compound of formula (I), e.g., IDE1 and/or IDE2, for 6 days. In some embodiments, the stem cell is exposed to the compound, e.g., an HDAC inhibitor(s) or a compound of formula (I), e.g., IDE1 and/or IDE2, at a concentration of about 25 nM, 50 nM, 100 nM, 150 nM, 200 nM, 250 nM, 400 nM, 500 nM, 600 nM, 700 nM, 800 nM, 1 µM, 2 µM, 3 µM, 4 µM, 5 µM or 10 µM. In some embodiments, the stem cell is exposed to the compound, e.g., an HDAC inhibitor(s) or a compound of formula (I), e.g., IDE1 and/or IDE2, at a concentration of about 250 nM, 400 nM, 500 nM, 600 nM, 700 nM, or 800 nM. In some embodiments, greater than about 20%, 30%, 40%, 50%, 60%, 70%, 80%, or 90% of the stems cells are differentiated into the endodermal cells, e.g., definitive endodermal cells. In some embodiments, the method further comprises exposing the stem cells to at least one additional agent. In some embodiments, the additional agent is Nodal, Activin A or Wnt3a.

The present invention may be as defined in any one of the following numbered paragraphs.

1. A method of producing a definitive endoderm cell from a pluripotent stem cell comprising contacting a population of pluripotent stem cells with at least one compound of Formula (I) to induce the differentiation of at least one pluripotent stem cell into a definitive endoderm cell, wherein the definitive endoderm cell expresses Sox17, or HNF3B (FoxA2), or Sox17 and HNF3B (FoxA2) and wherein the compound of formula (I) is:

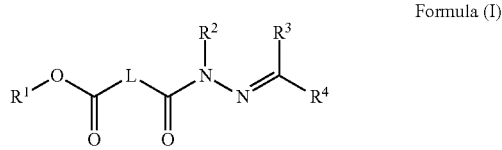

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

2. The method of paragraph 1, wherein the pluripotent stem cell is an embryonic stem (ES) cell.

3. The method of paragraphs 1 or 2, wherein the pluripotent stem cell is an induced pluripotent stem (iPS) cell.

4. The method of any of paragraphs 1 to 3, wherein the stem cell is from a mammal.

5. The method of any of paragraphs 1 to 4, wherein the stem cell is a human stem cell.

6. The method of any of paragraphs 1 to 5, wherein the method further comprising isolating a population of definitive endoderm cells, wherein at least 5%, 10%, 15%, 20%, 25%, 30%, 35%, 50%, 75% or greater of the total cells in the isolated population are definitive endoderm cells.

7. The method of any of paragraphs 1 to 6, wherein the compound of formula (I) is IDE1 having the structure:

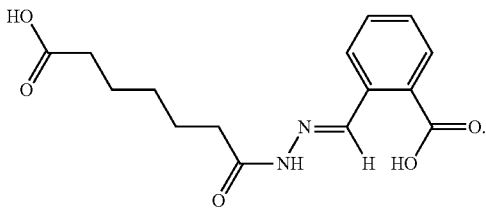 [SMILES: O=C(O)CCCCCC(=O)N/N=C/c1ccccc1C(=O)O]

8. The method of any of paragraphs 1 to 6, wherein the compound of formula (I) is IDE2 having the structure:

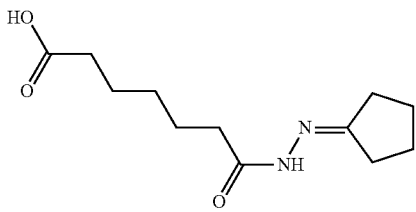 [SMILES: O=C(O)CCCCCC(=O)NN=C1CCCC1]

9. The method of any of paragraphs 1 to 8, wherein the compound of Formula (I) is an HDAC inhibitor.

10. The method of any of paragraphs 1 to 9, wherein the pluripotent stem cell is contacted with the compound of Formula (I) for at least 1 day.

11. The method of any of paragraphs 1 to 10, wherein the pluripotent stem cell is contacted with a compound of Formula (I) for at least 6 days.

12. The method of any of paragraphs 1 to 11, wherein the pluripotent stem cell is contacted with a compound of Formula (I) at a concentration of between 25 nM-10 µM.

13. The method of any of paragraphs 1 to 12, wherein the pluripotent stem cell is contacted with a compound of Formula (I) which is IDE1 at a concentration of between 50 nM-5 µM.

14. The method of any of paragraphs 1 to 13, wherein the pluripotent stem cell is contacted with a compound of Formula (I) which is IDE1 at a concentration of at least 50 nM.

15. The method of any of paragraphs 1 to 14, wherein the pluripotent stem cell is contacted with a compound of Formula (I) which is IDE1 at a concentration of at least 100 nM.

16. The method of any of paragraphs 1 to 15, wherein the pluripotent stem cell is contacted with a compound of Formula (I) which is IDE2 at a concentration of between 50 nM-5 µM.

17. The method of any of paragraphs 1 to 16, wherein the pluripotent stem cell is contacted with a compound of Formula (I) which is IDE2 at a concentration of at least 100 nM.

18. The method of any of paragraphs 1 to 17, wherein the pluripotent stem cell is contacted with a compound of Formula (I) which is IDE2 at a concentration of at least 200 nM.

19. The method of any of paragraphs 1 to 18, wherein at least 20% of the pluripotent stem cells in the population of pluripotent stem cells are induced to differentiate a definitive endoderm cell.

20. The method of any of paragraphs 1 to 19, wherein at least 40% of the pluripotent stem cells in the population of pluripotent stem cells are induced to differentiate a definitive endoderm cell.

21. The method of any of paragraphs 1 to 20, wherein at between 80-90% of the pluripotent stem cells in the population of pluripotent stem cells are induced to differentiate a definitive endoderm cell.

22. The method of any of paragraphs 1 to 21, the method further comprising exposing the stem cells to at least one additional agent.

23. The method of any of paragraphs 1 to 22, wherein the additional agent is selected from the group consisting of: Nodal, Activin A or Wnt3a.

24. The method of any of paragraphs 1 to 23, wherein the definitive endoderm cell expresses at least one marker selected from the group consisting of: Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Sox17, and Rbm35a, wherein the expression of at least one marker is upregulated to by a statistically significant amount in the definitive endoderm cell relative to the pluripotent stem cell from which it was derived.

25. The method of any of paragraphs 1 to 24, wherein the definitive endoderm cell does not express by a statistically significant amount at least one marker selected the group consisting of: Gata4, SPARC, AFP and Dab2 relative to the pluripotent stem cell from which it was derived.

26. The method of any of paragraphs 1 to 25, wherein the definitive endoderm cell does not express by a statistically significant amount at least one marker selected the group consisting of: Zic1, Pax6, Flk1 and CD31 relative to the pluripotent stem cell from which it was derived.

27. The method of any of paragraphs 1 to 26, wherein the definitive endoderm cell has a higher level of phosphorylation of Smad2 by a statistically significant amount relative to the pluripotent stem cell from which it was derived.

28. The method of any of paragraphs 1 to 27, wherein the definitive endoderm cell has the capacity to form gut tube in vivo.

29. The method of any of paragraphs 1 to 28, wherein the definitive endoderm cell can differentiate into a cell with morphology characteristic of a gut cell, and wherein a cell with morphology characteristic of a gut cell expresses FoxA2 and/or Claudin6.

30. The method of any of paragraphs 1 to 29, further comprising differentiating the definitive endoderm cell into a cell of endoderm origin.

31. The method of any of paragraphs 1 to 29, further comprising differentiating the definitive endoderm cell into a Pdx1-positive pancreatic progenitor cell, wherein the Pdx1-positive pancreatic progenitor cell expresses Pdx1.

32. The method of paragraph 31, wherein a Pdx1-positive pancreatic progenitor cell also expresses HNF6.

33. The method of paragraphs 31 or 32, comprising contacting a population of definitive endoderm cells with at least one compound of Formula (II) to induce the differentiation of at least one definitive endoderm cell into a Pdx1-positive pancreatic progenitor cell, wherein the compound of formula (II) is:

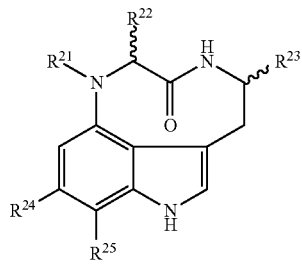

Formula (II)

$R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they are attached form an optionally substituted cyclyl.

34. The method of any of paragraphs 31 to 33, wherein the compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

35. The method of any of paragraphs 31 to 34, further comprising isolating the population of Pdx1-positive pancreatic progenitor cells.

36. The method of any of paragraphs 31 to 35, further comprising differentiating the population of Pdx1-positive pancreatic progenitor cells into a population of insulin producing cells.

37. The method of any of paragraphs 31 to 37, further comprising differentiating the population of Pdx1-positive pancreatic progenitor cells into a population of cells having at least one characteristic of endogenous pancreatic β-cells.

38. The method of any of paragraphs 31 to 37, wherein a cell with at least one characteristic of an endogenous pancreatic β-cell is secretion of insulin in response to glucose.

39. The method of any of paragraphs 31 to 38, further comprising implanting a population of Pdx1-positive pancreatic progenitor cells or their differentiated progeny of insulin producing cells or cells having at least one characteristic of endogenous pancreatic β-cells into a subject in need thereof.

40. The method of any of paragraphs 31 to 39, wherein the subject in need thereof has diabetes, or is at risk of developing diabetes.

41. The method of any of paragraphs 3 to 40, wherein the induced pluripotent stem (iPS) cell is from a subject with diabetes or at risk of developing diabetes.

42. An isolated population of definitive endoderm cells obtained from a population of pluripotent stem cells by a process comprising contacting the population of pluripotent stem cells with at least one compound of Formula (I), wherein the compound of Formula (I) is:

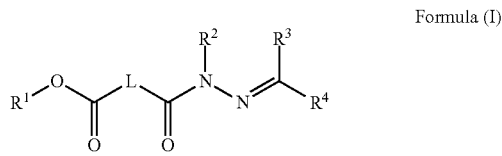

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

43. An isolated population of definitive endoderm cells obtained from a population of pluripotent stem cells by a process comprising contacting the population of pluripotent stem cells with at least one compound of IDE1 or IDE2, wherein the compound of IDE1 having the structure:

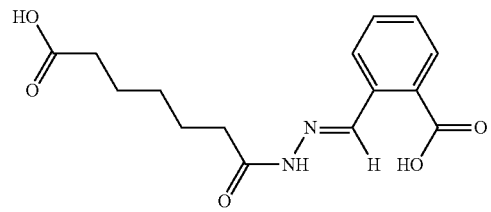 [SMILES: O=C(O)CCCCCC(=O)N/N=C/c1ccccc1C(=O)O]

and the compound of IDE2 having the structure:

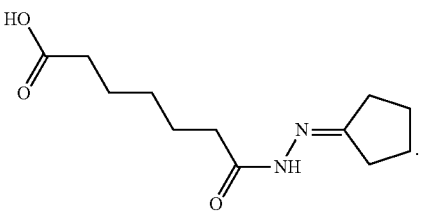 [SMILES: O=C(O)CCCCCC(=O)NN=C1CCCC1]

44. An isolated population of Pdx1-positive pancreatic progenitors obtained from a population of pluripotent stem cells by a process comprising: (i) contacting the population of pluripotent stem cells with at least one compound of Formula (I) to induce the differentiation of at least one pluripotent stem cell into definitive endoderm cell, and; (ii) contacting at least one definitive endoderm cell with at least one compound of Formula (II) to induce the differentiation of at least one definitive endoderm cell into a Pdx1-positive progenitor cell.

45. The isolated population of Pdx1-positive pancreatic progenitors of paragraph 44, wherein the compound of Formula (I) is:

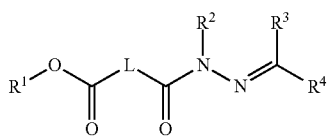

Formula (I)

wherein:

R¹ and R² are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

R³ and R⁴ are independently H, halogen, alkyl, alkenyl, alkynyl, alkoxy, aryl, heteroaryl, cyclyl, or cyclyl, each of which can be optionally substituted, or R³ and R⁴ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

46. The isolated population of Pdx1-positive pancreatic progenitors of paragraph 44 or 45, wherein the compound of Formula (I) is selected from IDE1 or IDE2, wherein the compound of IDE1 having the structure:

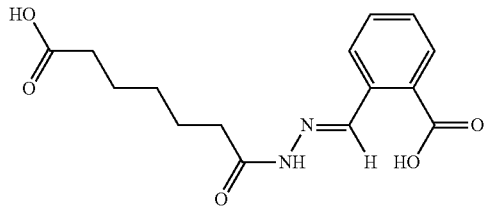 [SMILES: O=C(O)CCCCCC(=O)N/N=C/c1ccccc1C(=O)O]

and the compound of IDE2 having the structure:

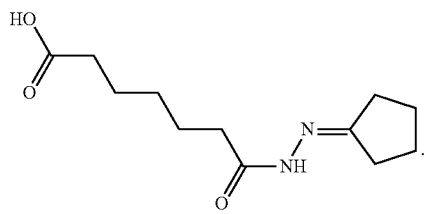

47. The isolated population of Pdx1-positive pancreatic progenitors of any of paragraphs 44 to 46, wherein the compound of Formula (II) is:

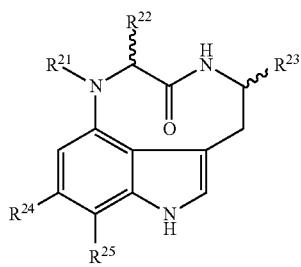

Formula (II)

$R^{21}$ is H, alkyl, alkenyl, alkynyl, aryl, heteroaryl, cyclyl, or cyclyl, each of which can be optionally substituted;

$R^{22}$ and $R^{23}$ independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they are attached form an optionally substituted cyclyl.

48. The isolated population of Pdx1-positive pancreatic progenitors of any of paragraphs 44 to 47, wherein the compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

49. A composition comprising a population of definitive endoderm cells produced according to the methods of any of paragraphs 1-30.

50. A composition comprising a population of Pdx1-positive pancreatic progenitor cells produced according to the methods of any of paragraphs 1 to 41 or 44 to 49.

51. A method for the treatment of a subject with diabetes, the method comprising administering to a subject a composition comprising an isolated population of Pdx1-positive pancreatic progenitor cells of any of paragraphs 44 to 49, or progeny thereof.

52. The method of paragraph 51, wherein the Pdx1-positive pancreatic progenitor cells are produced from a population of pluripotent stem cells obtained from the same subject as the Pdx1-positive pancreatic progenitor cells are administered to.

53. The method of paragraph 51 or 52, wherein the Pdx1-positive pancreatic progenitor cells are produced from an population of iPS cell, wherein the iPS cell is derived from a cell obtained from the same subject as the Pdx1-positive pancreatic progenitor cells are administered to.

54. The method of any of paragraphs 51 to 53, wherein the subject has, or has an increased risk of developing diabetes.

55. The method of any of paragraphs 51 to 54, wherein the diabetes is selected from the group of Type I diabetes, Type II diabetes, Type 1.5 diabetes and pre-diabetes.

56. The method of any of paragraphs 51 to 55, wherein the subject has, or has increased risk of developing a metabolic disorder.

57. Use of an isolated population of definitive endoderm cells produced by the methods according to paragraphs 1 to 30 or 42 to 43 for differentiating into Pdx1-positive pancreatic progenitors.

58. Use of an isolated population of definitive endoderm cells produced by the methods according to paragraphs 1 to 30 or 42 to 43 for differentiating into a cell of endoderm origin.

59. The use of paragraph 58, wherein the cell of endoderm origin is a cell selected from the group consisting of: a liver cell, a epithelial cell, a pancreatic cell, a pancreatic endoderm (PE) cell, a tymus cell, an intestine cell, a stomach cell, a thyroid cell and a lung cell.

60. Use of an isolated population of Pdx1-positive progenitors produced by the methods according to paragraphs 1 to 41 or 44 to 48 for administering to a subject in need thereof.

61. The use of paragraph 60, wherein the subject has, or has an increased risk of developing diabetes.

62. The use of paragraphs 60 or 61, wherein the diabetes is selected from the group of Type I diabetes, Type II diabetes, Type 1.5 and pre-diabetes.

63. The use of any of paragraphs 60 to 62, wherein the subject has, or has increased risk of developing a metabolic disorder.

64. A kit comprising at least one compound of Formula (I), wherein the compound of Formula (I) is:

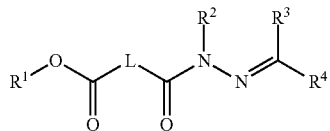

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

65. The kit of paragraph 64, wherein the compound of Formula (I) is selected from IDE1 or IDE2, wherein the compound of IDE1 having the structure:

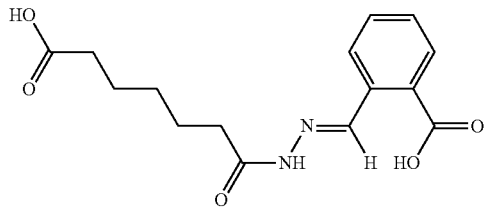 [SMILES: O=C(O)CCCCCC(=O)N/N=C/c1ccccc1C(=O)O]

and the compound of IDE2 having the structure:

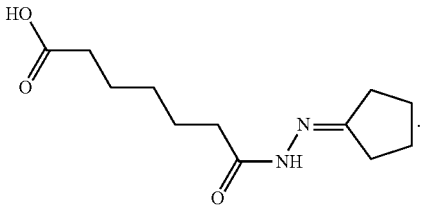

66. The kit of paragraph 64 or 65, further comprising at least one compound of Formula (II), wherein the compound of Formula (II) is:

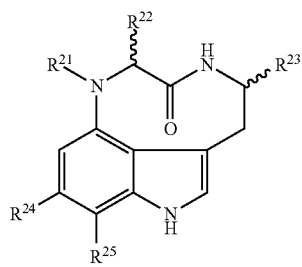

Formula (II)

$R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they are attached form an optionally substituted cyclyl.

67. The kit of any of paragraphs 64 to 66, wherein the compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

68. The kit of any of paragraphs 64 to 67, wherein the kit further comprises an isolated population of pluripotent stem cells.

69. The kit of any of paragraphs 64 to 68, wherein the isolated population of pluripotent stem cells is a control population of pluripotent stem cells.

70. The kit of any of paragraphs 64 to 69, further comprising a control cell population selected from the group of; an endoderm cell population, a definitive endoderm cell population, a pluripotent cell population, a Pdx1-positive pancreatic progenitor cell population.

71. The kit of any of paragraphs 64 to 70, further comprising at least one agent for the detection of a marker for a definitive endoderm cell, wherein the marker can be selected from any of the group consisting of; Nodal, Tmprss2, Tmem30b, St14, Spink3, Sh3gl2, Ripk4, Rab15, Npnt, Clic6, Cldn8, Cacna1b, Bnip1, Anxa4, Emb, FoxA1, Sox17, and Rbm35a.

72. The kit of any of paragraphs 64 to 71, further comprising at least one agent for the detection of a marker for a Pdx1-positive pancreatic progenitor, wherein the marker can be selected from any of the group consisting of; Pdx1 and HNF6.

73. A reaction admixture comprising a definitive endoderm cell and at least one compound of Formula (I), wherein the compound of Formula (I) is:

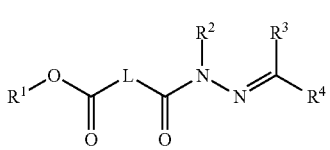

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

74. The reaction admixture of paragraph 73, wherein the compound of Formula (I) is selected from IDE1 or IDE2, wherein the compound of IDE1 having the structure:

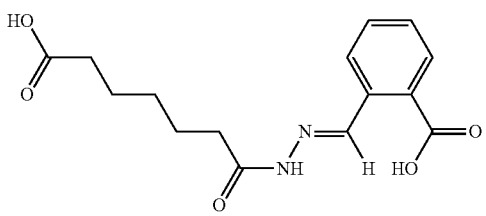 [SMILES: O=C(O)CCCCCC(=O)N/N=C/c1ccccc1C(=O)O]

and the compound of IDE2 having the structure:

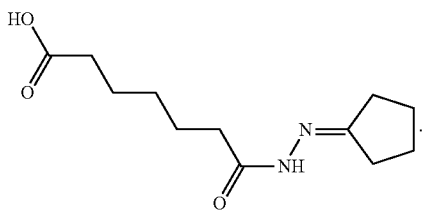

75. The reaction admixture of paragraphs 73 or 74, wherein the definitive endoderm cell is a human definitive endoderm cell.

76. A reaction admixture comprising a Pdx1-positive progenitor cell and at least one compound of Formula (II), wherein the compound of Formula (II) is:

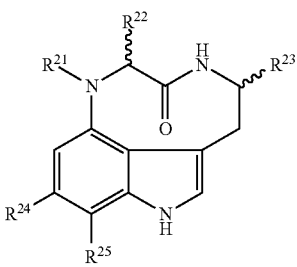

Formula (II)

$R^{21}$ is H, alkyl, alkenyl, alkynyl, aryl, heteroaryl, cyclyl, or cyclyl, each of which can be optionally substituted;

$R^{22}$ and $R^{23}$ are independently H, halogen, OH, alkyl, alkenyl, alkynyl, alkoxy, aryl, heteroaryl, cyclyl, or cyclyl, each of which can be optionally substituted; and $R^{24}$ and $R^{25}$ are each independently H, halogen, OH, SH, alkyl, alkenyl, alkynyl, alkoxy, thioalkoxy, aryl, heteroaryl, cyclyl, or cyclyl, each of which can be optionally substituted, or $R^{24}$ and $R^{25}$ together with the carbons to which they are attached form an optionally substituted cyclyl.

77. The reaction admixture of paragraph 76, wherein the compound of Formula (II) is (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one ((−)-indolactam V).

78. The reaction admixture of paragraph 76 or 77, wherein the Pdx1-positive progenitor cell is a human Pdx1-positive progenitor cell.

79. The reaction admixture of any of paragraphs 76 to 78, wherein the Pdx1-positive progenitor cell has been differentiated from a definitive endoderm cell, wherein the definitive endoderm cell has differentiated from a pluripotent stem cell by contacting the pluripotent stem cell with a compound of Formula (I).

80. The reaction admixture of any of paragraph 76 to 79, wherein the admixture further comprises at least one compound of Formula (I), wherein the compound of Formula (I) is:

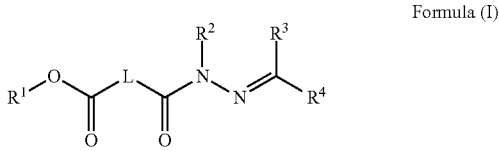

Formula (I)

wherein:

$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);

$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached from an optionally substituted cyclyl of heterocycyl; and L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

81. The reaction admixture of any of paragraphs 76 to 80, wherein the compound of Formula (I) is selected from IDE1 or IDE2, wherein the compound of IDE1 having the structure:

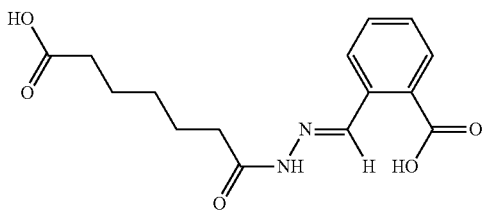

and the compound of IDE2 having the structure:

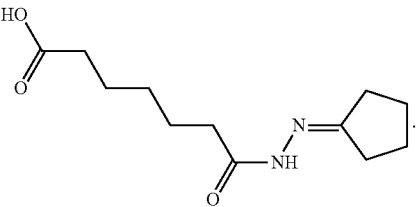 [SMILES: O=C(O)CCCCCC(=O)NN=C1CCCC1]

82. The reaction admixture of any of paragraphs 76 to 81, wherein the definitive endoderm cell is a human definitive endoderm cell.

In some embodiments, the methods described herein have one or more of the following advantages over other methods of making endoderm known in the art: the ability to produce endoderm, e.g., reduced cost of producing endoderm; easier and/or simplified production of endoderm, e.g., definitive endoderm, using a small molecule such as a compound described herein (for example, as opposed to a protein or other biological molecule); or increased efficiency in generating endoderm, e.g., definitive endoderm from stem cells. In some embodiments, a method described herein results in the production of Sox17+ endoderm, e.g., Sox17+ definitive endoderm by exposure to a small molecule compound such as a compound described herein.

In some embodiments, the methods described herein have one or more of the following advantages over other methods of the generation of pancreatic lineage cells by differentiation of endoderm (e.g., definitive endoderm) relative to other methods known in the art. Exemplary advantages include the ability to produce pancreatic cells and pancreatic precursor cells at low cost, easier and simplified production of pancreatic cells and pancreatic precursor cells, and increased efficiency in generating pancreatic cells and pancreatic precursor cells. In some embodiments, the methods described herein result in the production of Pdx1+ pancreatic cells and pancreatic precursor cells from endoderm (e.g., definitive endoderm) produced by the methods described herein.

In some examples, statistically significant means there is statistical evidence that there is a difference; it does not mean the difference is necessarily large, important, or significant in the common meaning of the word. The significance level of a test is a traditional frequentist statistical hypothesis testing concept. It can be defined as the probability of making a decision to reject the null hypothesis when the null hypothesis is actually true (a decision known as a Type I error, or "false positive determination"). The decision is often made using the p-value: if the p-value is less than the significance level, then the null hypothesis is rejected. The significance level of a test can also mean a probability such that the probability of making a decision to reject the null hypothesis when the null hypothesis is actually true is no more than the stated probability. This allows for those applications where the probability of deciding to reject may be much smaller than the significance level for some sets of assumptions encompassed within the null hypothesis.

EXAMPLES

Many modifications and variations of this invention can be made without departing from its spirit and scope, as will be apparent to those skilled in the art. The specific embodiments described herein are offered by way of example only, and the invention is to be limited only in terms of the appended claims, along with the full scope of equivalents to which such claims are entitled.

Experimental Procedures

Mouse ES cells culture and differentiation. Mouse ES cells were routinely cultured on irradiated CF-1 MEF feeder cells in DMEM (Gibco) media supplemented with 15% Fetal Bovine Serum (HyClone FBS, Invitrogen), 2 mM L-glutamine (L-Glu, Gibco), 1.1 mM 2-mercaptoethanol (Gibco), 1 mM nonessential amino acids (Gibco), 1×penicillin/streptomycin (P/S, Gibco) and $5×10^5$ units LIF (Chemicon). Cells were passaged at the ratio of 1:6-1:12 every 2-3 days using 0.25% trypsin. To generate the starting population, mouse ES cells was cultured on MEF feeder cells until they reached 80-90% confluence. Prior to differentiation, ES cells were passaged onto gelatin coated plates for 30 min to remove MEFs. MEF depleted ES cells were seeded at 2500 cells per $cm^2$ on gelatinized plates. After overnight culture, cells were exposed to 25 ng/ml Wnt3a (R&D Systems)+50 ng/ml recombinant Activin A (R&D Systems) or 500 ng/ml Nodal (R&D Systems) in DMEM (Gibco) supplemented with 1×L-Glu and 0.2% FBS (Gibco) for 1 day, then Activin A or Nodal in the same media and cultured for 4-6 days to induce endoderm differentiation. For the chemical inductions, compounds IDE1 and IDE2 (provided by Stuart L. Schreiber) were added at 5 μM concentration in the differentiation media. For pancreatic progenitors induction, the cells were transferred to 50 ng/ml FGF10 (R&D Systems), 0.75 μM KAAD-cyclopamine (Calbiochem) and 21.1M RA (Sigma) or Indolactam V 330 nM (Axxora) in DMEM supplemented with 1×L-Glu, 1×PS, 1×B27 (Invitrogen) for 4 days. SB431542 was purchased from Sigma. All stock compounds were made with either DMSO or PBS High throughput screen. To carry out the screen, mouse Sox17/dsRed ES cells (passage 16-20) were trypsinized, MEF depleted, and plated on gelatin-coated 384-well plates at density 800 cells/well using Biotek μFill. After overnight incubation in regular mouse ES media, the media was changed to low serum containing differentiating media (2% FBS) and compounds were added by pin transfer at final concentration 5 μM, in a volume 50 μl per well containing 1% DMSO (v/v). After an additional 6 days of culture, cells were washed twice with PBS, trypsinized for 3 min, suspended in FACS buffer (PBS, 5% FBS) and dsRed expression was detected by high throughput FACS analysis (Aria, Becton Dickinson).

Chemical libraries. The compound libraries used for this study included: the MicroSource library consisting of 2,000 bioactive compounds and known drugs, 1,000 synthetic compounds biased for HDAC inhibition (obtained from Stuart L. Schreiber laboratory) and a selection of hand-picked known modulators of stem cell fate (20 compounds), small molecule microarray consisting of approximately 400 compounds, including bioactives, natural products, and 400 compounds that are known modulators of development or signaling pathways (both prepared by Stuart L. Schreiber laboratory).

HUESC culture and differentiation. Human embryonic stem cell lines were cultured essentially as described {Cowan, 2004 #6}. Briefly, HUES4, HUES8 and HUES9 cells are routinely cultured on irradiated CF-1 MEF feeder cells in KnockOut DMEM (Gibco) supplemented with 10% KnockOut Serum Replacement (Gibco), 10% human plasma (Invitrogen), 2 mM L-glutamine (L-Glu, Gibco), 1.1 mM 2-mercaptoethanol (Gibco), 1 mM nonessential amino acids (Gibco), 1×penicillin/streptomycin (PS, Gibco) and 10 ng/ml bFGF (Invitrogen). Cells are split at the ratio of 1:10-1:12 every 4-5 days by using 1 mg/ml collagenase type IV. To induce endoderm formation, HUES cells was cultured on MEF feeder cells till 80-90% confluent, then treated with 100 ng/ml Activin A in advanced RPMI (Gibco) supplemented with 1×L-Glu and 0.2% FBS (Gibco), or with combination of 25 ng/ml Wnt3a (R&D systems)+100 ng/ml Activin A (R&D systems) or were exposed to compounds in the same media. At days 4 and 6 of culture cells were analysed for endodermal marker expression, Sox17.

Immunocytochemistry. Cells were fixed in 4% paraformaldehyde (Sigma) in PBS for 20 min at 4° C. followed by a wash with PBS. Cells were blocked with 10% donkey serum (Jackson Immunoresearch) in PBS/0.1% Triton X and incubated with primary antibodies overnight at 4° C. Secondary antibodies were incubated for 1 h at room temperature. The following antibodies and dilutions were used: goat anti-SOX17, (1:500 R&D systems); rabbit anti-PDX1 (1:200, Chemicon), rabbit anti-FoxA2 (1:500; Upstate), rabbit anti-Dab2 (1:200, Santa Cruz), rabbit anti-SPARC (1:200, Santa Cruz), mouse anti-AFP (1:100, Sigma), anti-Gata6 (1:50, Santa Cruz Biotech), goat anti-HNF6 (1:200, Santa Cruz Biotech), rabbit anti-RFP/DsRed (1:300, MBL), rabbit anti-GFP (1:200, Molecular Probes). Secondary antibodies were: rhodamine Red-X-conjugated donkey anti-goat antibody, 1:200 (JIRL), Alexa-488-conjugated goat anti-mouse and Alexa-594-conjugated goat anti-rabbit antibodies (1:300, Molecular Probes). Nuclei were visualized by Hoechst 33342 (1:1000, Molecular Probes). Images were taken using an Olympus IX70 Microscope. For quantification images were analyzed for the frequency of SOX17+, FoxA2+ or Pdx1+ cells using Metamorph image analysis software (Molecular Devices) and at least 6 images per well were collected. Data were confirmed in four independent experiments.

Flow cytometry. Cells were dissociated using 0.25% trypsin for 3 min followed by quenching of trypsin and further dissociation in PBS with 5% FBS. Suspension was filtered through nylon and cells were analysed and sorted out by MoFlo (Dako Cytomation, Ft. Collins, Colo.).

Quantification of endoderm formation. Endoderm formation was monitored by Sox17 expression by either flow cytometry detection of Sox17/DsRed or immunofluorescence using anti-Sox17 antibodies. Cells labeled by antibody staining were quantified using Metamorph software ad percentage of total cell number (based on Hoechst 33342 nuclei staining). All conditions were tested in either tri- or quadruplicates.

Global gene expression analysis. Sox17/DsRed+ cells were sorted out by FACS from mouse cell cultures treated either with growth factors or compounds. Total RNA was isolated using Qiashredder and RNAeasy Mini Kit (both from Qiagen). Biotinylated cRNA was prepared from ≧100 ng of isolated RNA using Illumina TotalPrep RNA Amplification Kit (Ambion) and hybridized to the Illumina mouse genome Bead Chips (MouseRef8). All samples were prepared as three biological replicates. Data were acquired with Illumina Beadstation 500 and were evaluated using BeadStudio Data Analysis Software (Illumina)

Western Blot analysis. Cells were lysed in 1×RIPA lysis buffer in the presence of protease inhibitor mixture (Roche)/ 1% phosphatase inhibitor mixture (Roche). Proteins were separated by 10% Tris-Glycine SDS/PAGE (Bio-rad) under denaturing conditions and transferred to a nitrocellulose membrane. After blocking with 5% skim milk in PBS/0.1% Triton X, the membrane was incubated with primary antibodies against phospho-Smad2 (1:1000, Cell Signaling) overnight at 4° C. The membrane was then washed, incubated with anti-mouse/rabbit peroxidase-conjugated affinity-purified secondary antibody (1:1000, Cell Signaling) at room temperature for 1 h, and developed by SuperSignal chemiluminescence (Pierce).

Injections into gut tube and embryo culture. Mouse E8.5 ICR embryos were dissected in Hanks Balanced Salt Solution and cultured in the DMEM/F12 (Invitrogen) media supplemented with 50% rat serum (Valley Biomedical), penicillin, streptomycin, glutamine at 37° C. for 20-24 hrs. The YFP mouse ES cells were cultured in the presence of hit compounds for 6 days to induce endoderm formation and then cells were dissociated with trypsin and approx. 100 000 cells were injected into gut tube of E8.75 embryos. Following injections, embryos were transferred to rotating bottle culture unit and were then cultured in media (1.5-2 ml per embryo) as above under humidified conditions at 40% $O_2$, 5% $CO_2$, 55% $N_2$, and 37° C. After 30 hrs culture, embryos were fixed in 4% paraformaldehyde in PBS, embedded in tissue-tek and cryosections were stained with antibodies against Cld6, FoxA2 an YFP.

Example 1

Screening with ES Cells for Endoderm Formation

A screen of 4000 compounds was performed to search for cell permeable small molecules that direct differentiation of ES cells into the endodermal lineage. Two compounds were found to induce nearly 80% of ES cells to form definitive endoderm, an efficiency higher than that achieved with Activin A or Nodal, the two most commonly used protein inducers of endoderm. Chemically induced endoderm expresses multiple endodermal markers, can participate in normal development when injected into the embryonic gut tube and can also be differentiated into pancreatic progenitors in vitro. This protocol to differentiate mouse and human ES cells into definitive endoderm and pancreatic progenitors with small molecules represents a step toward achieving a reproducible and efficient production of desired ES cell derivatives.

Specifically, describe herein are two small molecules, IDE1 and IDE2 (shown herein in FIG. 2A) that can efficiently induce definitive endoderm (IDE) from mouse ES cells. Treatment of mouse ES cell monolayer cultures with either compound yields high quantities of endoderm expressing multiple endodermal marker genes. Chemically derived endoderm develops into pancreatic progenitors in vitro in response to the growth factor FGF10, retinoic acid and hedgehog inhibitors, a commonly used combination to induce pancreatic progenitors in vitro. Moreover, the a recently identified small molecule, Indolactam V, was applied that induces pancreatic progenitors in human ES cell culture, to either IDE1 or IDE2 derived endoderm, and induce higher yields of pancreatic progenitors as compared to a growth factor based approach. Finally, it is demonstrated that compound induced endoderm can contribute to gut tube formation in vivo when the cells are injected into the developing gut tube of mouse embryos. Two small molecules are introduced, which induce a robust differentiation of mouse ES cells into endoderm that has the same or a very similar developmental potential to its in vivo counterpart. The induction of endoderm from ES cells by IDE1 and IDE2 is conserved between mouse and human species.

Figure 8:
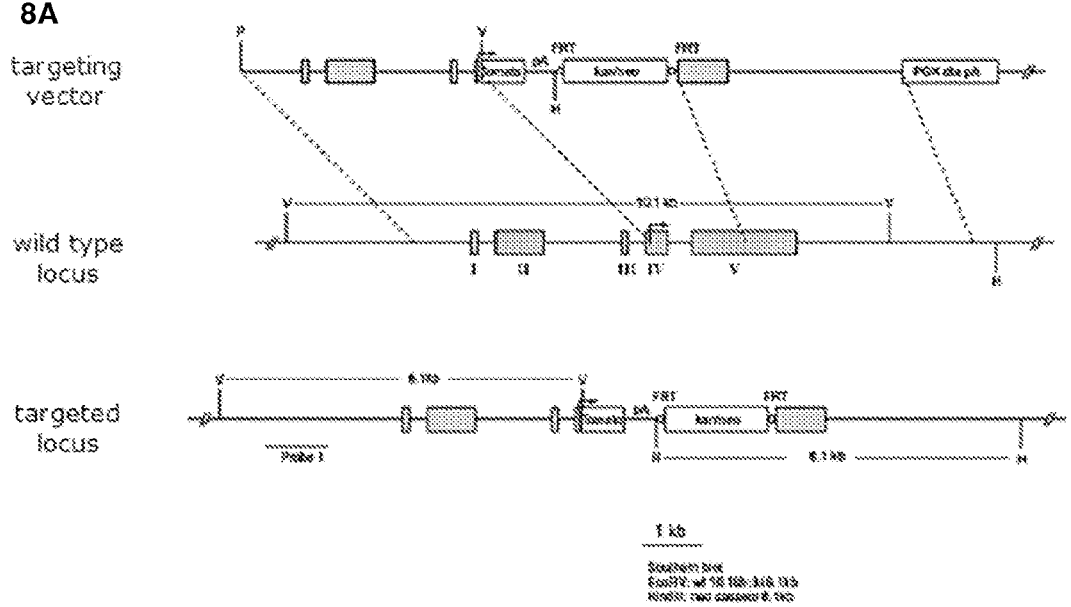
FIG. 8A-8B show the generation of Sox17-dsRed reporter mouse ES line.
Figure 8:
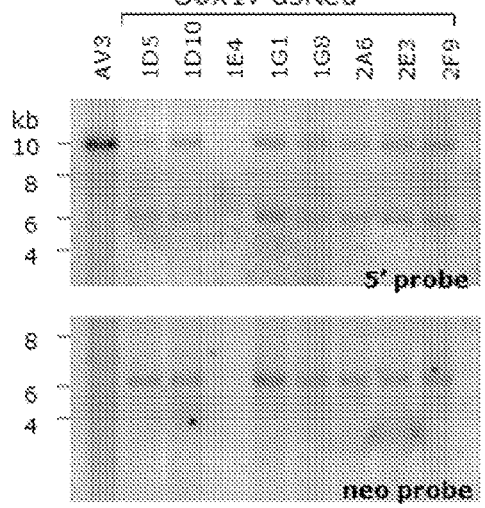

To obtain a reporter for endoderm formation the inventors generated a mouse ES cell line with the red-fluorescent protein dTomato, a variant of DsRed (Shaner et al., 2004) coding sequence under control of the Sox17 promoter (FIG. 8A). Several lines of evidence show that Sox17 is an endodermal marker, both definitive and extra-embryonic. A null mutation in mice is devoid of foregut endoderm and mid- and hindgut endoderm fails to expand (Kanai-Azuma et al., 2002). Gene expression analysis of isolated endoderm confirms that Sox17 is a marker of endoderm, both definitive and extra-embryonic (Sherwood et al., 2007). However, Sox17 expression is not restricted exclusively to endoderm; genetic lineage tracing shows that Sox17 is expressed in the endodermal lineage as early as E7.5 and but later on marks the gut tube as well as other organs (Park et al. 2006; Kim et al., 2007; Liu et al., 2007; R. Maehr, unpublished data).

In vitro, application of TGF-β family of growth factors, including Activin A or Nodal, to both mouse and human ES cell cultures, leads to the preferential differentiation into endodermal lineages (Kubo et al., 2004; Yasunaga et al., 2005; D'Amour et al., 2005). Consistent with those previous studies, endoderm induction is observed when Sox17-dsRed mouse ES cells are treated with Activin A for 6 days in low serum conditions (see Methods). At 6 days, 45% of cells stain positively for Sox17 and express dsRed (data not shown). All dsRed+ cells also express Sox17 protein as judged by Sox 17 antibody staining, which shows that the reporter line accurately reflects endogenous Sox17 expression. The co-expression of the fluorescent marker and endogenous Sox17 was also confirmed at all time points in vitro as well as in E6.5 and E7.5 embryos (data not shown). There is a minor population of cells (10±3.6%) that stained for Sox17, but did not express dsRed; however, no false positive expression of the transgene (DsRed positive but Sox17 antibody negative) was observed.

The endoderm differentiation protocol used in this screen is based on previously published protocols (Kubo et al., 2004; Yasunaga et al., 2005; D'Amour et al., 2005) with several modifications to allow endoderm lineage induction in a high throughput format. Specifically, the inventors culture the mouse ES cells as a monolayer (in contrast to embryoid bodies) in gelatin-coated 384 well plates without any feeder cell layer. The inventors also adjusted the cell density and media composition to promote better survival of mouse ES cells (see Methods for details).

Twelve hours after plating, Sox17-dsRed mouse ES cells were supplied with differentiation media (low serum content) and a single chemical compound was added by pin transfer. At this time point, (x=0) no dsRed+ and/or Sox17 antibody reactive cells were detected. In contrast, nearly all cells expressed Oct4, a pluripotency marker (data not shown). After day 6 of culture in the presence of compounds, the inventors evaluated Sox17/DsRed expression and total cell number by flow cytometry.

Over 4,000 compounds were tested from a small molecule collection consisting of known compounds that influence stem cell fate (such as retinoic acid and 5-azacytidine), bioactive compounds, compounds with known activity in signaling pathways, US Food and Drug Administration approved drugs, and a histone deacetylase (HDAC) inhibitors biased small molecule library resulting from diversity oriented synthesis.

Positive hits were defined as compounds that induce expression of Sox17/dsRed at three standard deviations above the DMSO (vehicle) control and were not auto-fluorescent or cytotoxic (FIG. 1B). Effects on cell viability or toxicity were set by requiring that the number of cells after 6 days of culture doubled i.e. reaching at least 1600 cells/well. Activin A treatment was used as a positive control. The effects of various treatments on differentiation were first evaluated by flow cytometric analysis for dsRed expressing cells and later confirmed by Sox17 and FoxA2 immunofluorescence and quantative-RT-PCR (Q-RT-PCR) analysis of endodermal markers including Sox/7, FoxA2, Gata4, Gata6, alpha-fetoprotein (Afp) and Sox7. Twenty seven compounds, ~1.5% of total screened compounds, were selected as primary hits and further characterized. The inventors also tested for the expression of ectodermal genes including Sox1, Pax6, Zic1 and mesodermal markers Pdgfr-α; Pdgfr-β and Meox1 by Q-RT-PCR (data not shown) to ensure specificity. Finally, since propensity to form different germ layer cell types varies between different mouse and human ES cell lines (Burridge et al., 2007; Osafune et al., 2008), the inventors tested primary hits using three mouse ES cell lines of two different genetic backgrounds (129 and 129/C57BL6 hybrid). Considering all these criteria, two small molecules, IDE1 and IDE2, were identified, out of the 27 primary hits, as inducers of endoderm and selected for further studies (FIG. 1B).

Example 2

Induction of Definitive and Extra-Embryonic Endoderm.

Figure 2:
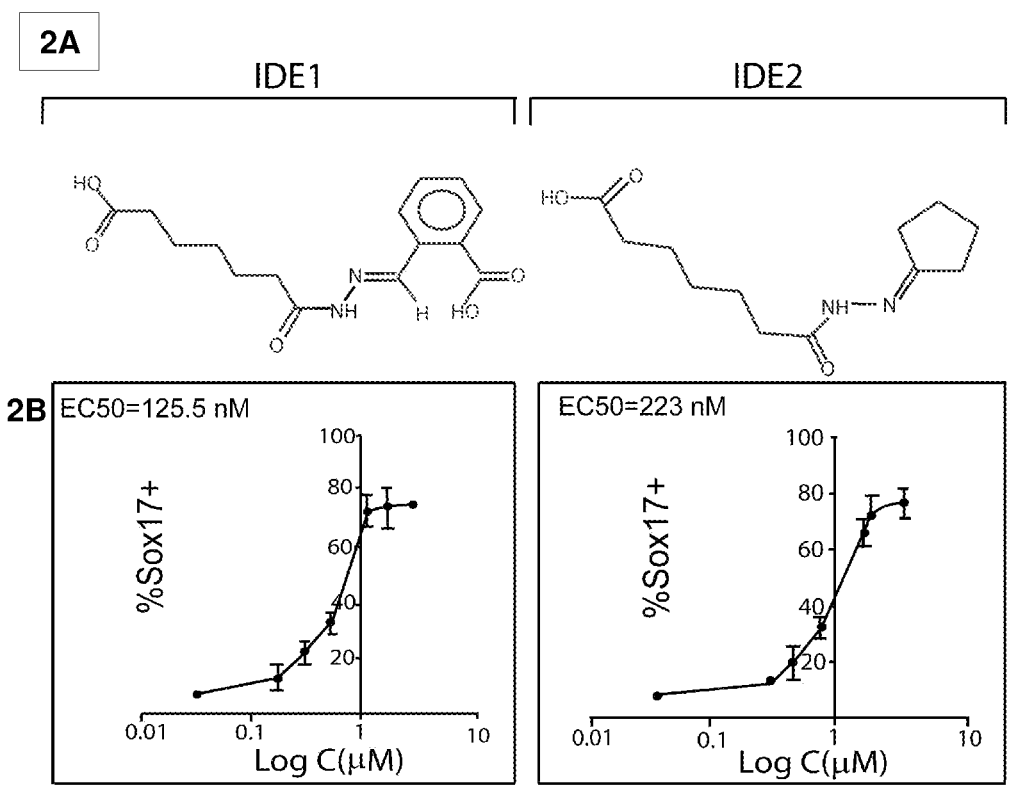
FIG. 2A-2B shows two small molecule inducers of endoderm (IDE).

During evaluation of primary hit compounds, the inventors observed that small molecules induced Sox17+ cells with two distinct morphologies. One class, including IDE1 and IDE2, induced clustered populations of Sox17+ cells, whereas other compounds led to the formation of a dispersed population of Sox17+ cells. In particular, the Sox17+ cells induced by IDE2 or IDE1 form a compact, epithelial sheet as identified by immunostaining with α-Sox17 antibody, whereas cells are more dispersed following treatment with a different small molecule (XE09), one that also induces Sox17 expression (data not shown). A third class of compounds induced cells with a mixed morphology. Sox17 is expressed in definitive endoderm, but also in extra-embryonic endoderm, and in other germ layer derivatives at later stages of development including vascular endothelium (Kanai-Azuma et al., 2002; Matsui et al., 2006). Since the positive identification of definitive endoderm is hindered by the lack of unique markers that are expressed exclusively there, and not present in other types of endoderm, the inventors performed a negative selection and tested for markers of extra-embryonic endoderm. It was found, that the vast majority (>95%) of the dispersed Sox17+ cells (class II) also expressed extra-embryonic endoderm markers including Gata4 (Morrisey et al., 1996), SPARC (Mason et al., 1986), AFP (Dziadek, 1979) and Dab2 (Yang et al., 2002) (Suppl. FIG. 2B). In particular, expression of extra-embryonic endoderm markers (EE), such as GATA4, SPARC, AFP and Dab2 are present in the dispersed population of Sox17+ cells but only rarely detected in the compact population of Sox17+ cells induced by the IDE2 compound. Similarly, treatment with IDE1 leads to marginal expression of EE markers (data not shown). Conversely, Sox17+ cells induced by treatment with either IDE2 or IDE1 (data not shown) formed clustered, epithelial like populations and contained no or a negligible number of cells positive for extra-embryonic markers.

Optimization of Definitive Endoderm Induction by Active Compounds

IDE1 and IDE2 are products of de novo chemical synthesis and come from a library of putative HDAC inhibitors (FIG. 2A, 2B). Titration of IDE1 and IDE2 from 50 nM to 5 μM showed that they function in a dose-dependent manner ($EC_{50}$=125 nM for IDE1 and $EC_{50}$=223 nM for IDE2, FIG. 2B) with the highest efficiency, and no toxicity, in the 250-800 nM range. The optimal concentration of IDE1 induces Sox17 expression in 80% and IDE2 in 72% of total ES cells at day 6 of treatment (data not shown), where αSox17 immunofluorescence was used to quantify the percent of total cells expressing Sox17 induction in mouse ES cells by each compound at day 6 of treatment. The majority of Sox17+ cells (≧95%) induced by IDE1 or IDE2 chemical treatment co-express another definitive endoderm marker, FoxA2. The inventors also tested for the expression of FoxA2 (also known as HNF3β), as an essential gene for the development of the definitive endoderm in mouse, (Ang et al., 1993; Monaghan et al., 1993; Sasaki and Hogan, 1993) and observed that over 95% of IDE1 or IDE2 compound induced Sox17+ cells co-express FoxA2 (data not shown).

Time Course and Synergy Between Active Compound and Growth Factors.

Figure 3:
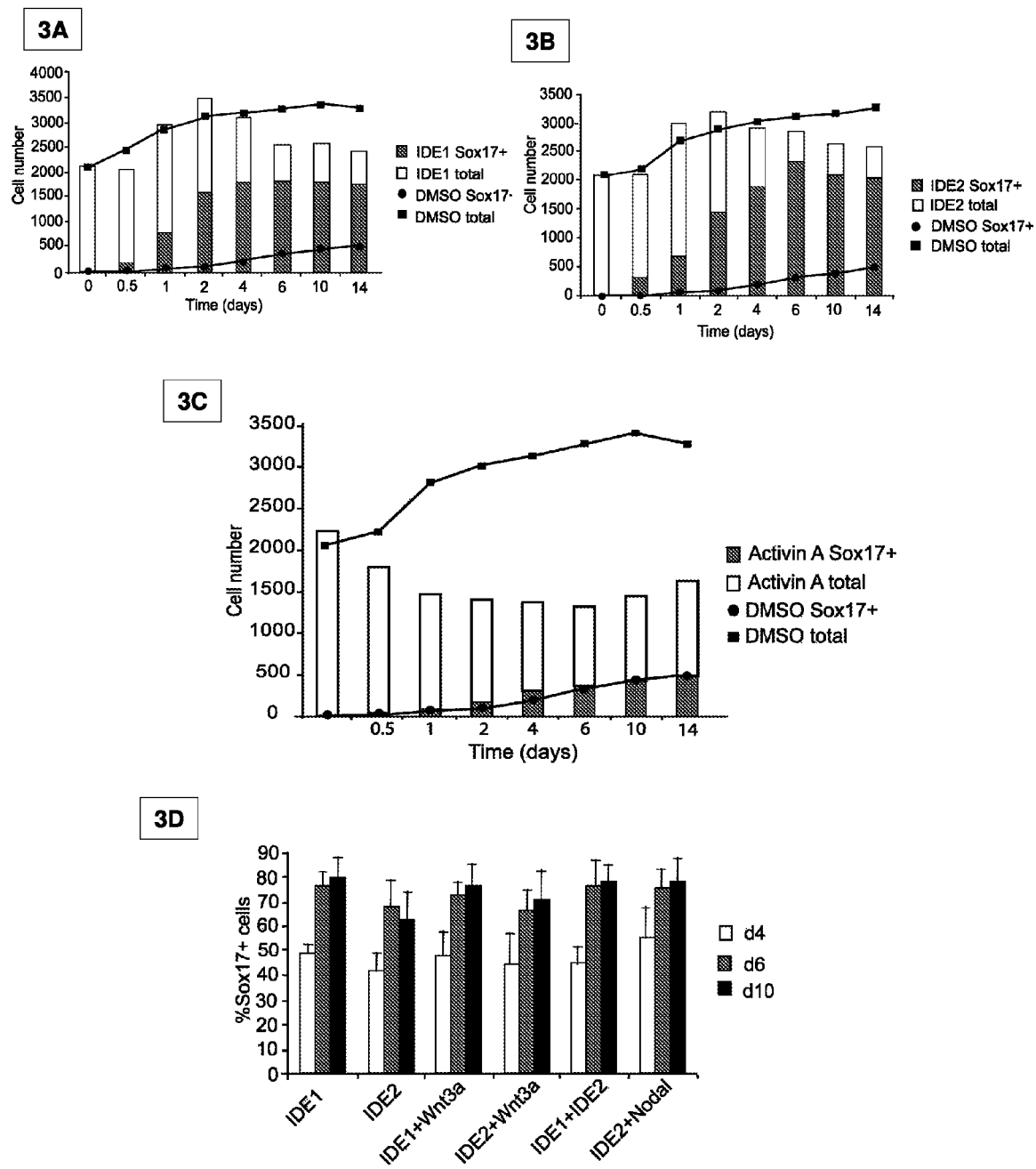
FIG. 3A-3D show time course of endoderm induction and synergy between different compound (IDE1, IDE2, Activin A) and growth factors (Wnt3a, Nodal).

Endoderm induction peaks at day 6 of treatment with small molecules, when 81±14% (for IDE1) treatment and 76±14% (for IDE2) out of total cell number were Sox17+ (FIGS. 3A, 3B and 3C). In the course of the next 8 days, the efficiency of endodermal induction does not significantly change. Compared to Activin A treatment both small molecules, under the conditions reported here, induced more cells to express Sox17, and at earlier time points. The percentage of cells expressing Sox17 at day 2 of treatment is 34% for IDE1 (FIG. 3A) and 32% for IDE2 (FIG. 3B), whereas Activin A yielded 13% Sox17+ cells (FIG. 3C); at day 4, 40-50% of cells treated with either of the compounds are Sox17+, whereas only 28% of Activin A treated cells are Sox17+.

Simultaneous treatment of mouse ES cells with both IDE1 and IDE2 did not produce any synergistic effect on Sox17+ induction (FIG. 3D). Co-treatment with IDE2 and Nodal, significantly (p≦0.001) increases the Sox17 induction at day 4 to 55.8±6.49%, compared to 42±3.83% with the compound alone. Wnt3a has no significant effect on Sox17 expression when combined with compounds.

IDE1 and IDE2 Induce Endoderm from Human Embryonic Stem Cells

The inventors also tested whether the hit compounds, have the ability to direct also human ES cells (HUES) into endodermal fate. Two HUES lines, HUES 4 and 8, treated with IDE1 and IDE2 compounds show propensity to differentiate into endodermal lineage (Osafune, 2008) and judged by Sox17 expression. Both compounds induced Sox17 expression in dose-depended manner. Treatment with IDE1 (100 nM) for 4 days leads to Sox17 expression in 62±8.1% of cells, an efficiency similar to Activin A treatment in these culture condition (64±6.3%). IDE2 (200 nM) induces Sox17 expression in 57±6.7% of total cell number, (data not shown) and the effect of IDE2 is significant different (p=0.00255) compared to the mock treatment (16%±3.6). Human ESC cultures were treated for 6 days with Activin A or vehicle (DMSO) only. Activin A treatment leads to Sox17 expression in 55-65% of total cells, which is 4-fold increase as compared to the vehicle treatment (data not shown). Co-treatment of human ES cells with Activin A and Wnt3a increases the efficiency of endoderm induction only by an additional 3-5%. A similar efficiency of endoderm induction was observed when HUES were culture in presence of MEF layer or on gelatin coated plates.

Example 3

Gene Expression Analysis of Endoderm Induced by Active Compounds

To determine whether other genes that compose part of an endodermal signature are induced in mouse ES cell cultures treated with active compounds, Sox17-DsRed+ cells were isolated by flow cytometry after day 6 of compound stimulation and profiled by gene expression analysis. Of nineteen genes previously defined as a definitive endoderm signature in the mouse (Sherwood et al., 2007), fourteen were induced more than two fold in the compound treated samples compared to mock treatment (FIG. 4A). Also compared was in vitro derived endoderm with its in vivo counterparts sorted-out from Sox17-DsRed E7.5-E8.5 embryos. Of these nineteen endoderm signature genes, only two genes, Spink3 and Tmprss2, were significantly different and were expressed at higher levels in the E7.5 endoderm (FIG. 4A). Furthermore, no significant changes in the expression of markers characteristic for other cell lineages were observed, such as the ectoderm markers Zic1, Pax6, and mesoderm markers Flk1, CD31 (data not shown) after compound treatment. The $r^2$ value (square of linear correlation coefficient) between chemically induced endoderm and Sox17/dsRed+ endoderm isolated from mouse E7.5-E8.0 embryos was 0.94-0.97 in three independent experiments (FIG. 4B). In contrast, the $r^2$ value for non-treated mouse ES cells and naïve endoderm isolated form E.75-8.0 embryos was 0.5-0.56 (FIG. 4B). These data suggest that in vitro derived endoderm by hit compound treatment is essentially equivalent to E7.5-E8.0 endoderm with respect to the expression of key endodermal markers.

Figure 5:
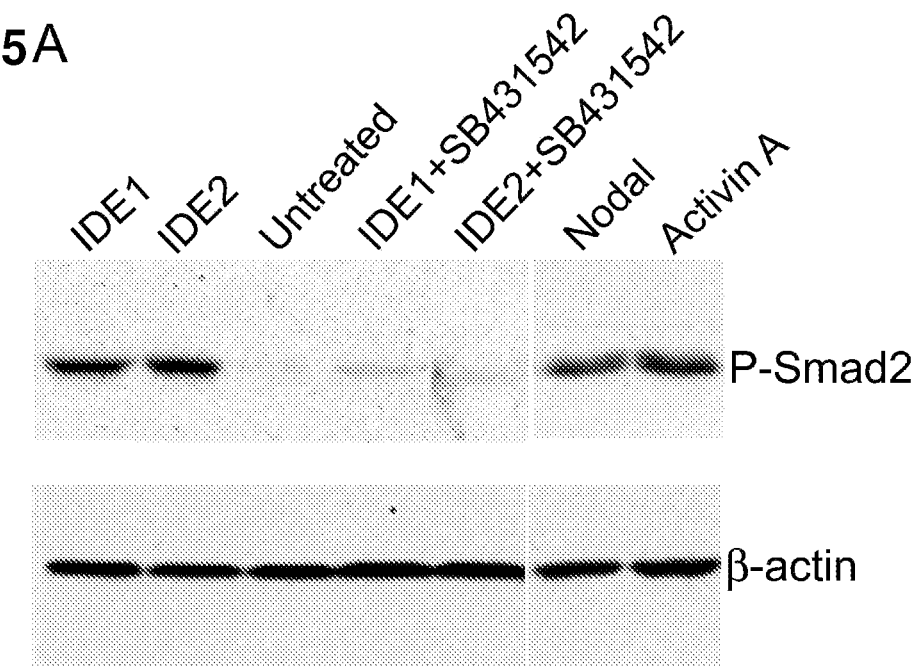
FIG. 5A-5B show the effect of IDE1 and IDE2 small molecule inducers of endoderm activate TGF-β signaling.
Figure 5:
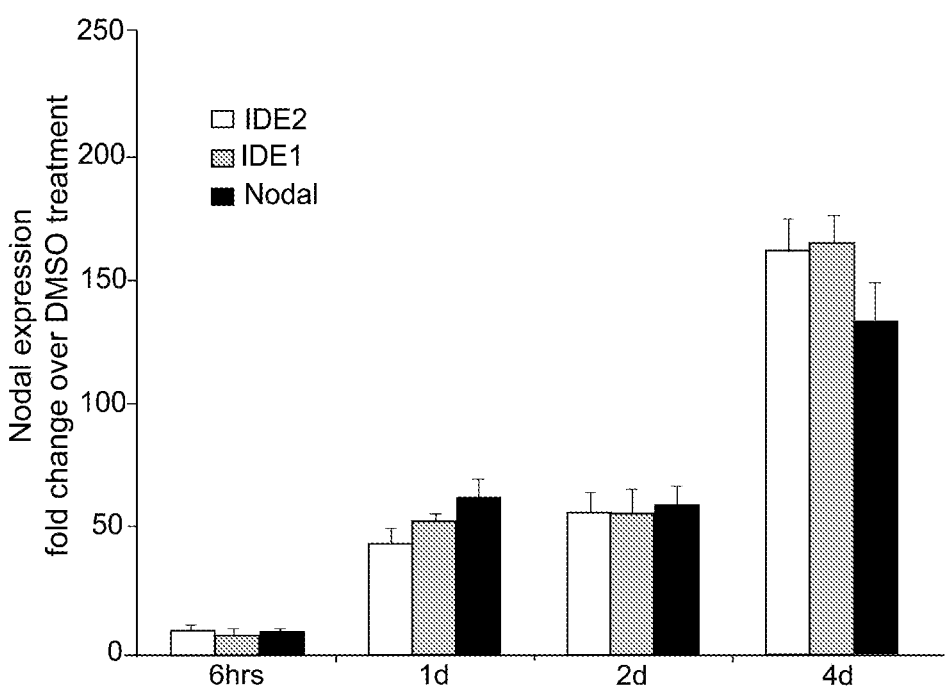

Activation of Nodal/Smad Signaling in Sox17+ Cells Produced by Small Molecules IDE1 and IDE2 Treatment Genetic and biochemical studies point to Smad proteins as the intracellular transducers of TGF-β signaling, including Activin A and Nodal (Whitman, 1998) and a high level of Smad2 phosphorylation is detected in cells lysates of ES cells that have been treated with Activin A or Nodal treatment. Both IDE1 and IDE2 induce phosphorylation of Smad2 after 24 hrs or longer at levels comparable to that induced by Activin A treatment (FIG. 5A). This phosphorylation of Smad2 is strongly attenuated by co-treatment of mouse ES cells with either of IDE1 or IDE2 compounds and the Activin receptor-like kinase 4/5/7 (ALK) inhibitor, SB43125. Under these conditions, induction of Sox17 protein is also reduced to 5.6±1.3% (data not shown). These data indicate that both IDE1 and IDE2 function by activating the TGF□ signaling pathway, however the specific biochemical targets of these small molecules are unknown.

Treatment with either of IDE1 or IDE2 compounds for 6 hrs leads to upregulation of Nodal transcripts by 6-8-fold compared to the control (FIG. 5B) and the levels of Nodal expression increase further with time of compound exposure. Nodal treatment increases its own expression at similar levels and time schedule. This may reflect an autoregulatory mechanism for maintaining and upregulating Nodal expression through a Smad2/FAST-1-dependent autoregulatory loop that feeds on Nodal transcription (Agius et al., 2000; Pogoda et al., 2000).

Example 4

In Vivo Competency of Chemically Derived Endoderm

Figure 6:
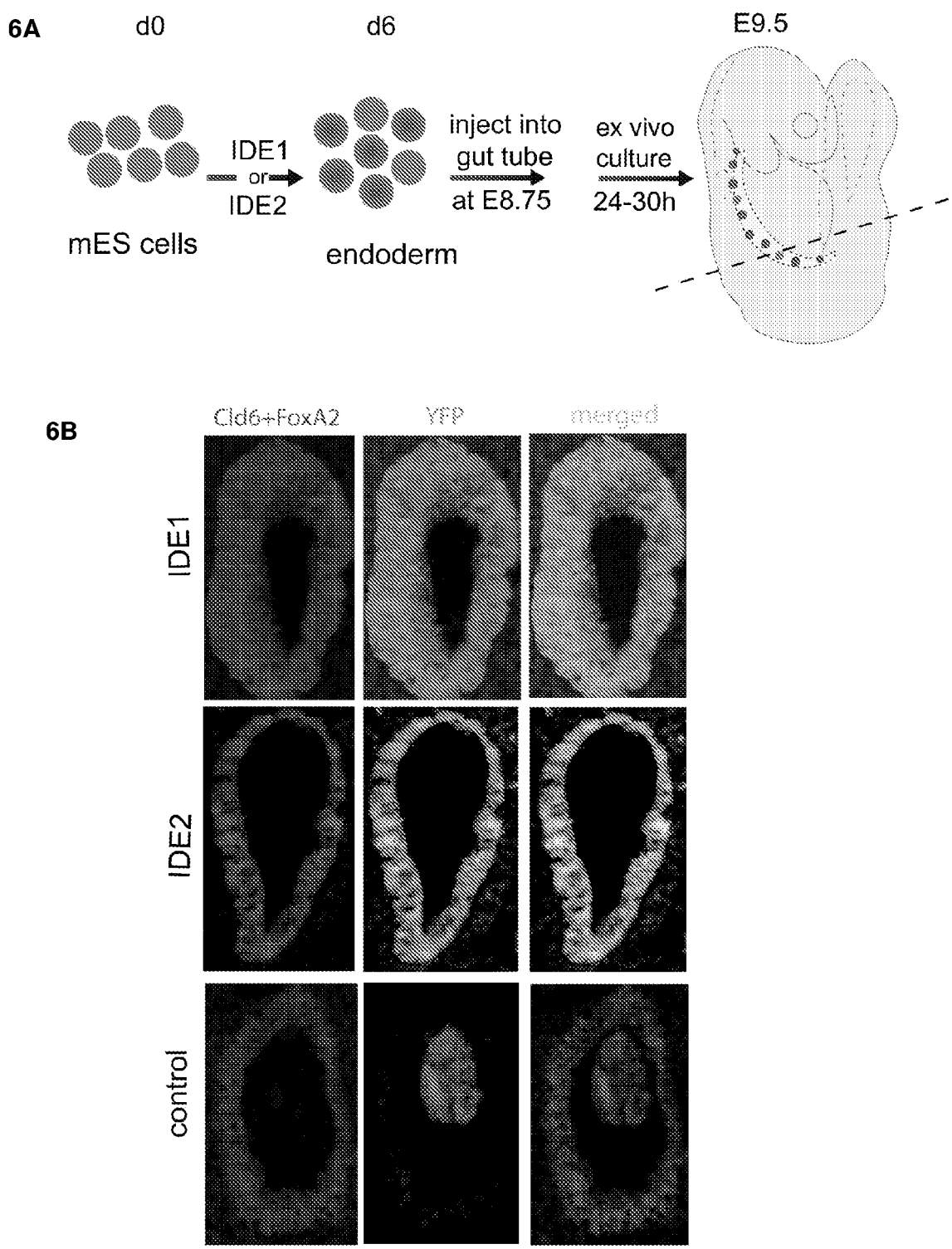
FIG. 6A-6B show functional evaluation of IDE1 and IDE2 chemically derived endoderm.

For chemically derived endoderm to be useful, it is important to determine its developmental potential, beyond the expression of endodermal markers. The ultimate goal is to direct the cells to form functional beta cells. To begin to address this possibility and functional potential of derived populations, mouse ES cells ubiquitously expressing enhanced yellow fluorescent protein (EYFP) (Hadjantonakis et al., 2002) were induced to form endoderm with IDE1, IDE2, or DMSO (control). At day 6 of treatment, the inventors dissociated and injected the cells into the gut tube (a derivative of endoderm) of live E8.75 embryos. The lumen of the gut tube can be accessed prior to the completion of embryonic turning and gut tube closure and therefore provides a developmental window for functional assessment of ES-derived endoderm cells. Chemically derived endoderm was injected into the primitive gut tube at the anterior and posterior intestinal portals. At this time the gut tube is still open and anterior intestinal portal is accessible (FIG. 6A). The embryos were cultured ex vivo for 24-30 hrs during which time the lateral walls of the embryonic gut fold ventrally and the gut tube closes, around E9.5. ES derived endodermal cells induced by small molecules integrated into the developing gut tube, whereas control treated ES cells did not. Moreover, ES cell derived endoderm showed the characteristic morphology of gut cells and expressed markers of gut tube markers including FoxA2 and Claudin6 (Anderson et al., 2008) (FIG. 6B). Cells induced by IDE1 treatment integrated into the gut, in 8 out of 35 cases, and in 7 out of 29 embryos for IDE2. Conversely, DMSO (control) treated cells never integrate into the developing gut tube (0/10 and 0/11, respectively) and instead remain in the lumen (FIG. 6B).

In Vitro Potential of Compound Induced Endoderm

To further evaluate the developmental potential of compound induced endoderm, the inventors tested whether it can differentiate in vitro into pancreatic progenitors. Pancreatic progenitors appear in the pancreatic bud at E9.5 and are marked by the expression of the transcription factor Pdx1. Pdx1 is required for pancreas development and β-cell formation, as a null mutation of Pdx1 in mice results in a failure to form a pancreas (Jonsson et al., 1994; Offield et al., 1996) and lineage tracing studies show that Pdx1 marks progenitors that give rise to all pancreatic cell types (Gu et al., 2003). Using Pdx1-GFP knock-in (Micallef et al., 2005) mouse ES cells the inventors induced definitive endoderm using either of the hit compounds and cultured cells in various conditions for additional six days.

Figure 7:
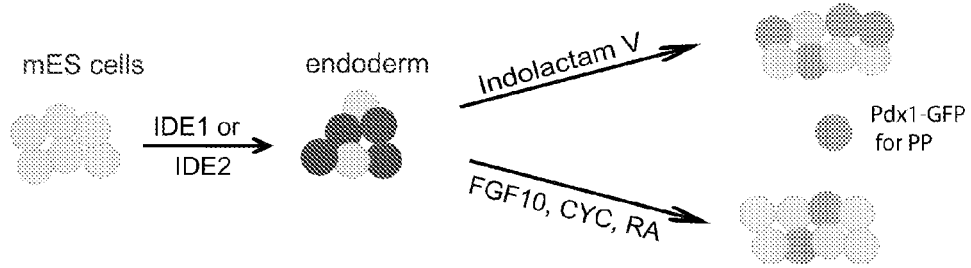
FIG. 7 shows a schematic of the developmental potential of IDE11 and IDE2 chemically derived endoderm, showing that differentiation of mouse ES cells into Pdx1+ pancreatic progenitors by treatment of IDE1 or IDE2. Endoderm cells are first derived through treatment with either IDE1 or IDE2 and then formation of pancreatic progenitors was monitored using a Pdx1-GFP reporter line.

Published protocols for differentiation of ES cells into pancreatic progenitors are based on studies of the factors that modulate signaling during pancreatic organogenesis (Stafford and Prince, 2002; Lau et al., 2006; Bhushan et al., 2001). For example, in one protocol, endoderm is induced with Activin A, followed by treatment with FGF10 and the Hedgehog signaling inhibitor KAAD-cyclopamine for 3 days, and then exposed to a posteriorizing factor, retinoic acid, for an additional 3 days to induce Pdx1 expression (D'Amour et al., 2006). Using this regimen, 12.1±4% of the mouse ES cells differentiate further into pancreatic progenitors, defined by Pdx1+ expression. By comparison, when compound induced endoderm was used as a starting population, instead of Activin A induced endoderm, 25±6% of cells expressed Pdx1. Spontaneous differentiation, in the absence of hit compounds, additional growth factors or signaling modulators, occurs at a lower level, producing GFP expression in 4.6±1.1% of cells (FIG. 7).

Example 5

Indolactam V can Induce Pancreatic Progenitors from Human Endoderm Cells

The inventors also performed a separate chemical screen using human cells to identify a compound, Indolactam V, that can induce pancreatic progenitors from endoderm that has been produced from human ES cells. Indolactam V is also able to efficiently induce pancreatic progenitors (Pdx1+ cells) in endoderm derived by chemical treatment of human or mouse ES.

Treatment of IDE1 or IDE2 induced mouse endoderm yields 51±7.4% Pdx1-GFP expressing pancreatic progenitors at day 6 (FIG. 7). In particular, endoderm enriched cultures were grown for another 6 days in chemically defined media containing: DMSO without any additional growth factors or IDE1 or IDE2 compounds (control), in presence of growth factors (FGF10, CYC, RA) or in the presence of Indolactam V (ILV) to induce the expression of Pdx1. At day 12, in cultures treated initially with IDE1 or IDE2 and followed by ILV, 50% of the total cells were Pdx1+, a 10-fold increase above control treatment (data not shown). When cultures were stained with Pdx1 antibodies similar number (53±6.4%) of positive cells were observed after two-step treatment with small molecules, namely a first step of culturing in the presence of IDE1 and/or IDE2, then a second stem of culturing in the presence of Indolactam V (ILV). Notably, this is a 10-fold increase in Pdx1+ cell number compared to the control DMSO treated and a 4-fold increase compared to known published protocols. The majority of Pdx1+ (92±5%) cells also express other pancreatic progenitor markers, including HNF6. For example, coexpression of pancreatic markers, Pdx1 and HFN6 was detected by immunostaining in cells induced by a two-step small molecule protocol; where the first step comprises contacting the mouse ESCs with IDE2 or IDE1 for about 6 days to induce definitive endoderm and then, in the second step, where the IDE1 or IDE2-induced definitive endoderm cells were treated with Indolactam V for an additional 6 days to allow pancreatic progenitor specification, which were detected using antibodies co-expressing both Pdx1 and HNF6 (data not shown). Together, these compounds provide a two-step protocol for in vitro generation of pancreatic progenitors that utilizes the small molecules at each step, first as inducers of endoderm and later to generate pancreatic progenitors.

Described herein are two potent small molecules, IDE1 and IDE2 that can direct mouse ES cells differentiation such that 70-80% of cells are endoderm cells. Both compounds are products of de novo synthesis and their biological activity has not been previously reported. This efficiency of induction compares favorably with published protocols employing TGF-β family members, e.g. Activin A or Nodal, which produce about 45% endoderm. Both IDEs small molecules induce endoderm formation in human ES cell cultures. In the long term, the potential benefits of finding chemicals like IDE1 or IDE2 include the prospect of minimizing the risk of animal disease infections and a cost reduction for materials and the temporal control that can be achieved using small molecules which can be easily delivered and removed. Application of either of the two small molecules reported here does not eliminate the necessity of serum presence in the differentiation protocols. These results enhance the repertoire of chemical compounds for manipulating ES cell fate and encourage the high throughput screening of small molecules to direct differentiation of ES cells under chemically defined conditions.

With respect to their potential to induce endoderm, IDE1 and IDE2 appear to be interchangeable as substantial differences as far as efficiency, gene expression or functional potential between populations induced by the two compounds was observed. Both compounds are novel and their specific biological targets remain to be identified, but a strong hint comes from the fact that they activate part of a TGF-β pathway as evidenced by Smad2 phosphorylation.

In the experiments reported here, mouse ES were cultured in the absence of feeders or other supportive cell types. However, extrinsic signaling could well improve the efficiency of the differentiation and maturation of cells. Interactions between endoderm and different mesodermal cell types pattern the gut epithelium into progenitor domains and promote local organ outgrowth (Horb and Slack, 2001; Deutsch et al., 2001; Kumar et al., 2003). One source for prospective inductive signals is pancreatic mesenchyme which supports budding of dorsal pancreatic tissue into the stroma (Golosow and Grobstein, 1962; Wells and Melton, 2000). Another important signal comes from vessel endothelium which provides inductive signals for islet development (Lammert et al., 2001). Future studies may identify small molecule substitutes for these developmental signals.

If in vitro differentiation of ES cells is to be used for treating human diseases, including diabetes, it will likely require derivation of large quantities of cells with high purity in chemically defined conditions. This study shows the feasibility of chemical screening to identify molecules that may achieve this effect, in this case direct ES cells into endoderm, which is relevant for liver, lung, stomach, intestine, and thymus as well as the pancreas.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

REFERENCES

All references cited herein are incorporated herein by reference in their entirety as if each individual publication or patent or patent application was specifically and individually indicated to be incorporated by reference in its entirety.

Agius, E., Oelgeschlager, M., Wessely, O., Kemp, C., and De Robertis, E. M. (2000). Endodermal Nodal-related signals and mesoderm induction in *Xenopus*. Development 127, 1173-1183.

Anderson, W. J., Zhou, Q., Alcalde, V., Kaneko, O. F., Blank, L. J., Sherwood, R. I., Guseh, J. S., Rajagopal, J., and Melton, D. A. (2008). Genetic targeting of the endoderm with claudin-6(CreER). Dev Dyn 237, 504-512.

Ang, S. L., Wierda, A., Wong, D., Stevens, K. A., Cascio, S., Rossant, J., and Zaret, K. S. (1993). The formation and maintenance of the definitive endoderm lineage in the mouse: involvement of HNF3/forkhead proteins. Development 119, 1301-1315.

Bhushan, A., Itoh, N., Kato, S., Thiery, J. P., Czernichow, P., Bellusci, S., and Scharfmann, R. (2001). Fgf10 is essential for maintaining the proliferative capacity of epithelial progenitor cells during early pancreatic organogenesis. Development 128, 5109-5117.

Burridge, P. W., Anderson, D., Priddle, H., Barbadillo Munoz, M. D., Chamberlain, S., Allegrucci, C., Young, L. E., and Denning, C. (2007). Improved human embryonic stem cell embryoid body homogeneity and cardiomyocyte differentiation from a novel V-96 plate aggregation system highlights interline variability. Stem Cells 25, 929-938.

Chen, S., Do, J. T., Zhang, Q., Yao, S., Yan, F., Peters, E. C., Scholer, H. R., Schultz, P. G., and Ding, S. (2006). Self-renewal of embryonic stem cells by a small molecule. Proc Natl Acad Sci USA 103, 17266-17271.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

Desbordes, S.C., Placantonakis, D. G., Ciro, A., Socci, N. D., Lee, G., Djaballah, H., and Studer, L. (2008). High-throughput screening assay for the identification of compounds regulating self-renewal and differentiation in human embryonic stem cells. Cell Stem Cell 2, 602-612.

Deutsch, G., Jung, J., Zheng, M., Lora, J., and Zaret, K. S. (2001). A bipotential precursor population for pancreas and liver within the embryonic endoderm. Development 128, 871-881.

Diamandis, P., Wildenhain, J., Clarke, I. D., Sacher, A. G., Graham, J., Bellows, D. S., Ling, E. K., Ward, R. J., Jamieson, L. G., Tyers, M., and Dirks, P. B. (2007). Chemical genetics reveals a complex functional ground state of neural stem cells. Nat Chem Biol 3, 268-273.

Ding, S., and Schultz, P. G. (2004). A role for chemistry in stem cell biology. Nat Biotechnol 22, 833-840.

Dziadek, M. (1979). Cell differentiation in isolated inner cell masses of mouse blastocysts in vitro: onset of specific gene expression. J Embryol Exp Morphol 53, 367-379.

Golosow, N., and Grobstein, C. (1962). Epitheliomesenchymal interaction in pancreatic morphogenesis. Dev Biol 4, 242-255.

Gu, G., Brown, J. R., and Melton, D. A. (2003). Direct lineage tracing reveals the ontogeny of pancreatic cell fates during mouse embryogenesis. Mech Dev 120, 35-43.

Hadjantonakis, A. K., Macmaster, S., and Nagy, A. (2002). Embryonic stem cells and mice expressing different GFP variants for multiple non-invasive reporter usage within a single animal. BMC Biotechnol 2, 11.

Horb, M. E., and Slack, J. M. (2001). Endoderm specification and differentiation in *Xenopus* embryos. Dev Biol 236, 330-343.

Jonsson, J., Carlsson, L., Edlund, T., and Edlund, H. (1994). Insulin-promoter-factor 1 is required for pancreas development in mice. Nature 371, 606-609.

Kanai-Azuma, M., Kanai, Y., Gad, J. M., Tajima, Y., Taya, C., Kurohmaru, M., Sanai, Y., Yonekawa, H., Yazaki, K., Tam, P. P., and Hayashi, Y. (2002). Depletion of definitive gut endoderm in Sox17-null mutant mice. Development 129, 2367-2379.

Kim, I., Saunders, T. L., and Morrison, S. J. (2007). Sox17 dependence distinguishes the transcriptional regulation of fetal from adult hematopoietic stem cells. Cell 130, 470-483.

Kubo, A., Shinozaki, K., Shannon, J. M., Kouskoff, V., Kennedy, M., Woo, S., Fehling, H. J., and Keller, G. (2004). Development of definitive endoderm from embryonic stem cells in culture. Development 131, 1651-1662.

Kumar, M., Jordan, N., Melton, D., and Grapin-Botton, A. (2003). Signals from lateral plate mesoderm instruct endoderm toward a pancreatic fate. Dev Biol 259, 109-122.

Lammert, E., Cleaver, O., and Melton, D. (2001). Induction of pancreatic differentiation by signals from blood vessels. Science 294, 564-567.

Lau, J., Kawahira, H., and Hebrok, M. (2006). Hedgehog signaling in pancreas development and disease. Cell Mol Life Sci 63, 642-652.

Lewis, S. L., and Tam, P. P. (2006). Definitive endoderm of the mouse embryo: formation, cell fates, and morphogenetic function. Dev Dyn 235, 2315-2329.

Liu, Y., Asakura, M., Inoue, H., Nakamura, T., Sano, M., Niu, Z., Chen, M., Schwartz, R. J., and Schneider, M. D. (2007). Sox17 is essential for the specification of cardiac mesoderm in embryonic stem cells. Proc Natl Acad Sci USA 104, 3859-3864.

Mason, I. J., Murphy, D., Munke, M., Francke, U., Elliott, R. W., and Hogan, B. L. (1986). Developmental and transformation-sensitive expression of the Sparc gene on mouse chromosome 11. Embo J 5, 1831-1837.

Matsui, T., Kanai-Azuma, M., Hara, K., Matoba, S., Hiramatsu, R., Kawakami, H., Kurohmaru, M., Koopman, P., and Kanai, Y. (2006). Redundant roles of Sox17 and Sox18 in postnatal angiogenesis in mice. J Cell Sci 119, 3513-3526.

McLean, A. B., D'Amour, K. A., Jones, K. L., Krishnamoorthy, M., Kulik, M. J., Reynolds, D. M., Sheppard, A. M., Liu, H., Xu, Y., Baetge, E. E., and Dalton, S. (2007). Activin a efficiently specifies definitive endoderm from human embryonic stem cells only when phosphatidylinositol 3-kinase signaling is suppressed. Stem Cells 25, 29-38.

Micallef, S. J., Janes, M. E., Knezevic, K., Davis, R. P., Elefanty, A. G., and Stanley, E. G. (2005). Retinoic acid induces Pdx1-positive endoderm in differentiating mouse embryonic stem cells. Diabetes 54, 301-305.

Monaghan, A. P., Kaestner, K. H., Grau, E., and Schutz, G. (1993). Postimplantation expression patterns indicate a role for the mouse forkhead/HNF-3 alpha, beta and gamma genes in determination of the definitive endoderm, chordamesoderm and neuroectoderm. Development 119, 567-578.

Morrisey, E. E., Ip, H. S., Lu, M. M., and Parmacek, M. S. (1996). GATA-6: a zinc finger transcription factor that is expressed in multiple cell lineages derived from lateral mesoderm. Dev Biol 177, 309-322.

Offield, M. F., Jetton, T. L., Labosky, P. A., Ray, M., Stein, R. W., Magnuson, M. A., Hogan, B. L., and Wright, C. V. (1996). PDX1-1 is required for pancreatic outgrowth and differentiation of the rostral duodenum. Development 122, 983-995.

Osafune, K., Caron, L., Borowiak, M., Martinez, R. J., Fitz-Gerald, C. S., Sato, Y., Cowan, C. A., Chien, K. R., and Melton, D. A. (2008). Marked differences in differentiation propensity among human embryonic stem cell lines. Nat Biotechnol 26, 313-315.

Park, K. S., Wells, J. M., Zorn, A. M., Wert, S. E., and Whitsett, J. A. (2006). Sox17 influences the differentiation of respiratory epithelial cells. Dev Biol 294, 192-202.

Pogoda, H. M., Solnica-Krezel, L., Driever, W., and Meyer, D. (2000). The zebrafish forkhead transcription factor FoxH1/Fast1 is a modulator of nodal signaling required for organizer formation. Curr Biol 10, 1041-1049.

Sakamoto, Y., Hara, K., Kanai-Azuma, M., Matsui, T., Miura, Y., Tsunekawa, N., Kurohmaru, M., Saijoh, Y., Koopman, P., and Kanai, Y. (2007). Redundant roles of Sox17 and Sox18 in early cardiovascular development of mouse embryos. Biochem Biophys Res Commun 360, 539-544.

Sasaki, H., and Hogan, B. L. (1993). Differential expression of multiple fork head related genes during gastrulation and axial pattern formation in the mouse embryo. Development 118, 47-59.

Shaner, N. C., Campbell, R. E., Steinbach, P. A., Giepmans, B. N., Palmer, A. E., and Tsien, R. Y. (2004). Improved monomeric red, orange and yellow fluorescent proteins derived from *Discosoma* sp. red fluorescent protein. Nat Biotechnol 22, 1567-1572.

Sherwood, R. I., Jitianu, C., Cleaver, O., Shaywitz, D. A., Lamenzo, J. O., Chen, A. E., Golub, T. R., and Melton, D. A. (2007). Prospective isolation and global gene expression analysis of definitive and visceral endoderm. Dev Biol 304, 541-555.

Stafford, D., and Prince, V. E. (2002). Retinoic acid signaling is required for a critical early step in zebrafish pancreatic development. Curr Biol 12, 1215-1220.

Wells, J. M., and Melton, D. A. (1999). Vertebrate endoderm development. Annu Rev Cell Dev Biol 15, 393-410.

Wells, J. M., and Melton, D. A. (2000). Early mouse endoderm is patterned by soluble factors from adjacent germ layers. Development 127, 1563-1572.

Whitman, M. (1998). Smads and early developmental signaling by the TGFbeta superfamily. Genes Dev 12, 2445-2462.

Wu, X., Ding, S., Ding, Q., Gray, N. S., and Schultz, P. G. (2004). Small molecules that induce cardiomyogenesis in embryonic stem cells. J Am Chem Soc 126, 1590-1591.

Yang, D. H., Smith, E. R., Roland, I. H., Sheng, Z., He, J., Martin, W. D., Hamilton, T. C., Lambeth, J. D., and Xu, X. X. (2002). Disabled-2 is essential for endodermal cell positioning and structure formation during mouse embryogenesis. Dev Biol 251, 27-44.

Yasunaga, M., Tada, S., Torikai-Nishikawa, S., Nakano, Y., Okada, M., Jakt, L. M., Nishikawa, S., Chiba, T., and Era, T. (2005). Induction and monitoring of definitive and visceral endoderm differentiation of mouse ES cells. Nat Biotechnol 23, 1542-1550.

What is claimed is:

1. A method of producing a definitive endoderm cell from a pluripotent stem cell comprising contacting a population of pluripotent stem cells with at least one compound of Formula (I) that activates TGF-β signaling, thereby inducing the differentiation of at least one pluripotent stem cell into a definitive endoderm cell, wherein the definitive endoderm cell expresses Sox17, or HNF3B (FoxA2), or Sox17 and HNF3B (FoxA2) and wherein the compound of formula (I) is:

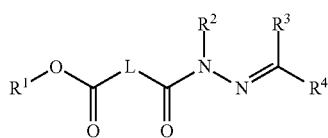

Formula (I)

wherein:
$R^1$ and $R^2$ are independently H, alkyl, alkenyl, alkynyl, aryl, heteroaryl, cyclyl, or cyclyl, each of which can be optionally substituted and/or can be interrupted in the backbone with one or more of O, N, S, S(O), and C(O);
$R^3$ and $R^4$ are independently H, halogen, alkyl, alkenyl, alkynyl, alkoxy, aryl, heteroaryl, cyclyl, or cyclyl, each of which can be optionally substituted, or $R^3$ and $R^4$ together with the carbon to which they are attached form an optionally substituted cyclyl or heterocyclyl; and
L is $C_1$-$C_{10}$ alkylenyl, $C_2$-$C_{10}$ alkenylenyl, or $C_2$-$C_{10}$ alkynylenyl, each of which can be optionally substituted and/or can be interrupted in the backbone with one or more of O, N, S, S(O), and C(O).

2. The method of claim 1, wherein the pluripotent stem cell is an embryonic stem (ES) cell or an induced pluripotent stem (iPS) cell.

3. The method of claim 1, wherein the stem cell is from a mammal.

4. The method of claim 1, wherein the stem cell is a human stem cell.

5. The method of claim 1, wherein the method further comprising isolating a population of definitive endoderm cells, wherein at least 5%, 10%, 15%, 20%, 25%, 30%, 35%, 50%, or 75% of the total cells in the isolated population are definitive endoderm cells.

6. The method of claim 1, wherein the compound of formula (I) is 2-[(6-carboxy-hexanoyl)-hydrazonomethyl]-benzoic acid (IDE1) or 7-(2-cyclopentylidenehydrazino)-7-oxo-heptanoic acid (IDE2).

7. The method of claim 1, wherein the compound of formula (I) has the structure

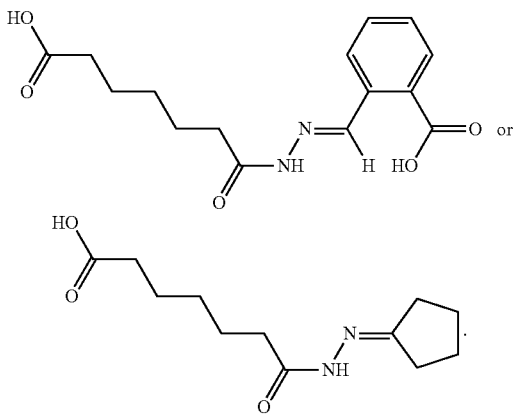

8. The method of claim 1, the method further comprising exposing the stem cells to at least one additional agent.

9. The method of claim 8, wherein the additional agent is selected from the group consisting of: Nodal, Activin A or Wnt3a.

* * * * *